United States Patent [19]
Kohn et al.

[11] Patent Number: 5,654,301
[45] Date of Patent: Aug. 5, 1997

[54] AMINO ACID DERIVATIVE ANTICONVULSANT

[75] Inventors: Harold L. Kohn, Houston; Darrell Watson, Belton, both of Tex.

[73] Assignee: Research Corporation Technologies, Inc., Tucson, Ariz.

[21] Appl. No.: 3,208

[22] Filed: Jan. 12, 1993

Related U.S. Application Data

[63] Continuation-in-part of Ser. No. 710,610, Jun. 4, 1991, Pat. No. 5,378,729, which is a continuation-in-part of Ser. No. 354,057, May 19, 1989, abandoned, and a continuation-in-part of Ser. No. 392,870, Aug. 11, 1989, abandoned, said Ser. No. 354,057, is a continuation-in-part of Ser. No. 80,528, Jul. 31, 1987, abandoned, which is a continuation-in-part of Ser. No. 916,254, Oct. 7, 1986, abandoned, which is a continuation-in-part of Ser. No. 702,195, Feb. 15, 1985, abandoned, said Ser. No. 392,870, is a continuation of Ser. No. 80,528, Jul. 31, 1987, abandoned, which is a continuation-in-part of Ser. No. 916,254, Oct. 7, 1986, abandoned, which is a continuation-in-part of Ser. No. 702,195, Feb. 15, 1985, abandoned.

[30] Foreign Application Priority Data

Jun. 4, 1992 [WO] WIPO .................... US92/04687

[51] Int. Cl.⁶ .................... A61K 31/445; A61K 31/34; C07D 211/72; C07D 261/04
[52] U.S. Cl. .................... 514/231.2; 514/315; 514/397; 514/406; 514/415; 514/424; 514/461; 514/468; 514/486; 514/616; 546/292; 548/125; 548/225; 548/250; 548/347.1; 548/245; 548/371.4; 564/152; 564/154; 564/292
[58] Field of Search .................... 564/148, 155, 564/154, 152; 548/125, 245, 371.4; 514/315, 357, 461, 406, 548, 424, 415, 549, 618, 486, 231.2; 546/252, 152, 154

[56] References Cited

U.S. PATENT DOCUMENTS

| | | | |
|---|---|---|---|
| 2,676,188 | 4/1954 | Bruce et al. | 424/319 |
| 2,721,197 | 10/1955 | Sheehan | 564/155 |
| 3,340,147 | 9/1967 | Martin et al. | 514/616 |
| 3,657,341 | 4/1972 | Thorne et al. | 260/558 A |
| 3,707,559 | 12/1972 | Mazur et al. | 564/158 |
| 4,018,826 | 4/1977 | Gless, Jr. et al. | 564/215 |
| 4,260,684 | 4/1981 | Schult | 564/155 |
| 4,303,673 | 12/1981 | Biedermann et al. | 564/155 |
| 4,372,974 | 2/1983 | Fish et al. | 260/559 |
| 4,513,009 | 4/1985 | Roques et al. | |
| 4,595,700 | 6/1986 | Donald et al. | 514/616 |
| 4,618,708 | 10/1986 | Roques et al. | 564/154 |
| 4,873,241 | 10/1989 | Napier et al. | 564/215 |
| 5,378,729 | 1/1995 | Kohn et al. | 514/231.2 |

FOREIGN PATENT DOCUMENTS

| | | |
|---|---|---|
| 0885303 | 3/1981 | Belgium . |
| 0007441 | 2/1980 | European Pat. Off. . |
| 0194464 | 2/1980 | European Pat. Off. . |
| 0038758 | 10/1981 | European Pat. Off. . |
| 0042626 | 12/1981 | European Pat. Off. . |
| 0046707 | 3/1982 | European Pat. Off. . |
| 0263506 | 10/1987 | European Pat. Off. . |
| 0400400 | 5/1990 | European Pat. Off. . |
| 1927692 | 12/1969 | Germany . |
| 0393355 | 10/1965 | Switzerland . |
| 1051220 | 12/1966 | United Kingdom . |

OTHER PUBLICATIONS

Remington, Pharmaceutical Sciences, Mack Publishing Company, (1980) pp. 400–427.
Chemical Abstracts, vol. 92; No. 7:51712r (Feb. 18, 1990).
Chemical Abstracts, vol. 96; No. 5:35710r (Feb. 1, 1982).
Chemical Abstracts, vol. 101; No. 9; 72124v (Aug. 27, 1984).
Chemical Abstracts, vol. 91; No. 21:175147; (Nov. 19, 1979).
Kohn, et al. (1988) Brain Research 457: 371–375, Marked Stereospecificity in a New Class of Anticonvulsants.
Chemical Abstracts, vol. 97;145266d (1982).
Chemical Abstracts, vol. 89; 129286q; Zafloukal, et al. (1978).
White, et al. (1981) JACS, 103:4231–4239, Active–Site–Directed Inhibition of alpha–Chymotrypsin by Deaminatively Produced Carbonium Ions: An Example of Suicide of Enzyme–Activated–Substrate Inhibition.
Legall, et al. (1988) Int. J. Protein Res., 32:279–291 Synthesis of Functionalized Non–Natural Amino Acid Derivatives via Amidoalkylation Transformations.
Cortes, et al. (1985) J. Med. Chem., 28:601–606, Effect of Structural Modification of the Hydantion Ring on Anticonvulsant Activity.
Ikeda, et al. (1977) Tetrahedron, 33(5):489–495, photochemical Synthesis of 1,2,3, 4–Tetrahydroisoquinolin–3–ones from N–Chloracetylbenzylamines.
Conley, et al. (1987) J. Med. Chem., 30(3): 567–574 Functionalized DL–Amino Acid Derivatives, Potent New Agents for the Treatment of Epilepsy.
Garcia, et al. (1984) Tetrahedron Letters, 25(42) 4841–4844, New Synthetic "Tricks" Triphenylphosphine–Mediated Amide Formation from Carboxylic Acids and Azides.
Rebek, et al. (1979), J. Am. Chem. Soc., 101(3):737, On the Rate of Site–Site Interactions in Functionalized Polystyrenes.
Katritzky, et al. (1990) J. Org. Chem., 55:2206–2214, Benzotrialzole–Assisted Synthesis of Monacyl Animals and Their Peptide Derivatives.
Lipshutz, et al. (1983) J. Am. Chem. Soc., 105:7703–7713, Heterocycles as masked Diamide/Dipeptide Equivalents. Formation and Reactions of Substituted 5–(Acylamino)oxazoles as Intermidiates en route to the Cyclopeptide Alkaloids.

(List continued on next page.)

Primary Examiner—Theodore J. Criares
Attorney, Agent, or Firm—Scully, Scott, Murphy & Presser

[57] ABSTRACT

The present invention relates to compounds of the formula

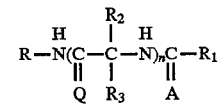

47 Claims, No Drawings

OTHER PUBLICATIONS

Lipshutz, et al. (1993) J. Org. Chem., 48:3745–3750, An Approach to the Cyclo–peptide Alkaloids (Phencycopeptines) via Heterocyclic Diamide/Dipeptide Equivalents. Preparation and N–Alkylation Studies of 2,4(5)–Disubstituted Imidazoles.

Roques, 91987) 193rd ACS National Meeting, Amer. Chem. Soc., Apr. 5–10, 1987 Use of Various Metallopeptides Inhibitors to Study the Physiological Role of Endogenous Neuropetides.

Kohn, et al. (1990) J. Med. Chem., 33:919–926, Preparation and Anticonvulsant Activity of a Series of Functionalized α–Aromatic and α–Heteroaromatic Amino Acids.

Lipshutz, et al. JACS, 106(2):457–459, "Heterocycles in Synthesis . . . Imidazoles" (1984).

Kohn, et al. (1988) Chemistry in Britain, pp. 231–233, New Antiepileptic Agents.

AMINO ACID DERIVATIVE ANTICONVULSANT

RELATED APPLICATIONS

The present application is a continuation-in-part of U.S. patent application Ser. No. 710,610 filed on Jun. 4, 1991, now U.S. Pat. No. 5,378,729 which is a continuation-in-part of U.S. patent application Ser. No. 354,057 filed on May 19, 1989, now abandoned and U.S. patent application Ser. No. 392,870 filed on Aug. 11, 1989, now abandoned. U.S. patent application Ser. No. 354,057 is a continuation-in-part of U.S. patent application having Ser. No. 080,528, filed on Jul. 31, 1987, now abandoned, which is a continuation-in-part of U.S. patent application Ser. No. 916,254, filed Oct. 7, 1986, now abandoned which is a continuation-in-part of U.S. patent application Ser. No. 702,195, filed Feb. 15, 1985, now abandoned. U.S. patent application Ser. No. 392,870 is a continuation application of U.S. patent application having Ser. No. 080,528, filed Jul. 31, 1987, now abandoned, which is a continuation-in-part of U.S. patent application Ser. No. 916,254 filed Oct. 7, 1986, now abandoned which is a continuation-in-part of U.S. patent application Ser. No. 702,195 filed on Feb. 15, 1985, now abandoned.

This invention was made with Government support under NS15604 awarded by the National Institutes of Health. The Government has certain rights to this invention.

BACKGROUND OF THE INVENTION

The present invention relates to compounds and pharmaceutical compositions having central nervous system (CNS) activity which are useful in the treatment of epilepsy and other CNS disorders. More specifically, the compounds of this invention can be characterized as protected amino acid derivatives of the formula:

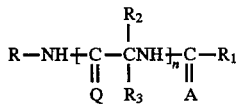

or the N-oxides thereof or pharmaceutically acceptable salts thereof wherein

R is hydrogen, lower alkyl, lower alkenyl, lower alkynyl, aryl, aryl lower alkyl, heterocyclic, heterocyclic lower alkyl, loweralkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, $SO_3^-$ or Z—Y wherein $R_2$ and $R_3$ may be unsubstituted or substituted with at least one electron withdrawing group or electron donating group;

Z is O, S, S(O)$_a$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, cycloalkyl, cycloalkyl lower alkyl and Y may be unsubstituted or substituted with an electron donating group or an electron withdrawing group, provided Z is a chemical bond only, when Y is halo, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$ $PR_4NR_5R_7$,

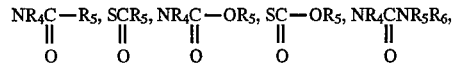

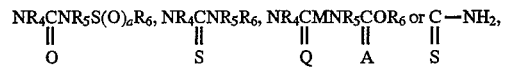

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group and $R_7$ is $R_6$ or $COOR_8$ or $COR_8$ $R_8$ is hydrogen or lower alkyl, or aryl lower alkyl, and the aryl or alkyl group may be unsubstituted or substituted with an electron withdrawing group or an electron donating group and A and Q are independently O or S, M is an alkylene chain containing up to 6 carbon atoms or a chemical bond;

n is 1–4 and a is 1–3.

The predominant application of anticonvulsant drugs is the control and prevention of seizures associated with epilepsy or related central nervous system disorders. Epilepsy refers to many types of recurrent seizures produced by paroxysmal excessive neuronal discharges in the brain; the two main generalized seizures are petit mal, which is associated with myoclonic jerks, akinetic seizures, transient loss of consciousness, but without convulsion; and grand mal which manifests in a continuous series of seizures and convulsions with loss of consciousness.

The mainstay of treatment for such disorders has been the long-term and consistent administration of anticonvulsant drugs. Most drugs in use are weak acids that, presumably, exert their action on neurons, glial cells or both of the central nervous system. The majority of these compounds are characterized by the presence of at least one amide unit and one or more benzene rings that are present as a phenyl group or part of a cyclic system.

Much attention has been focused upon the development of anticonvulsant drugs and today many such drugs are well known. For example, the hydantions, such as phenytoin, are useful in the control of generalized seizures and all forms of partial seizures. The oxazolidinediones, such as trimethadione and paramethadione, are used in the treatment of non-convulsive seizures. Phenacemide, a phenylacetylurea, is one of the most well known anticonvulsants employed today, while much attention has recently been dedicated to the investigation of the diazepines and piperazines. For example, U.S. Pat. Nos. 4,002,764 and 4,178,378 to Allgeier, et al. disclose esterified diazepine derivatives useful in the treatment of epilepsy and other nervous disorders. U.S. Pat. No. 3,887,543 to Nakanishi, et al. describes a thieno[2,3-e][1,4]diazepine compound also having anticonvulsant activity and other depressant activity. U.S. Pat. No. 4,209,516 to Heckendorn, et al. relates to triazole derivatives which exhibit anticonvulsant activity and are useful in the treatment of epilepsy and conditions of tension and agitation. U.S. Pat. No. 4,322,974 to Fish, et al. discloses a pharmaceutical formulation containing an aliphatic amino acid compound in which the carboxylic acid and primary amine are separated by three or four units. Administration of these compounds in an acid pH range are useful in the treatment of convulsion disorders and also possess anxiolytic and sedative properties.

Unfortunately, despite the many available pharmacotherapeutic agents, a significant percentage of the population with epilepsy or related disorders are poorly managed. Moreover, none of the drugs presently available are capable of achieving total seizure control and most have disturbing side-effects. Clearly, current therapy has failed to "seize control" of these debilitating diseases.

It is therefore one object of the present invention to provide novel compounds exhibiting CNS activity, particularly anticonvulsant activity.

Another object of this invention is to provide pharmaceutical compositions useful in the treatment of epilepsy and other CNS disorders.

A further object of this invention is to provide a method of treating epilepsy and related convulsant disorders.

These and other objects are accomplished herein by providing compounds of the following general formula:

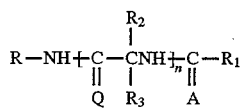

wherein R, $R_1$, $R_2$, $R_3$, $R_4$, $R_5$, $R_6$, n, Z, Y, A and Q are as defined hereinabove.

The present invention contemplates employing the compounds of Formula I in compositions of pharmaceutically acceptable dosage forms. Where the appropriate substituents are employed, the present invention also includes pharmaceutically acceptable addition salts. Moreover, the administration of an effective amount of the present compounds, in their pharmaceutically acceptable forms or the addition salts thereof, can provide an excellent regime for the treatment of epilepsy, nervous anxiety, psychosis, insomnia and other related central nervous disorders.

The alkyl groups when used alone or in combination with other groups, are lower alkyl containing from 1 to 6 carbon atoms and may be straight chain or branched. These groups include methyl, ethyl, propyl, isopropyl, butyl, isobutyl, tertiary butyl, amyl, hexyl, and the like.

The aryl lower alkyl groups include, for example, benzyl, phenethyl, phenpropyl, phenisopropyl, phenbutyl, and the like, diphenylmethyl, 1,1-diphenylethyl, 1,2-diphenylethyl, and the like.

The term aryl, when used along or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. Polynuclear aromatic compound is meant to encompass bicyclic, tricyclic fused aromatic ring system containing from 10–18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl.

Lower alkenyl is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E-)-4-methyl-2-pentenyl, pentadienyl, e.g., 1,3 or 2,4-pentadienyl, and the like.

The term alkynyl include alkyene substituents containing 2 to 6 carbon atoms and may be straight chained as well as branched. It includes such groups as ethynyl, propynyl, 1-butynyl, 2-butynyl, 1-pentynl, 2-pentynyl, 3-methyl-1-pentynyl, 3-pentynyl, 1-hexynyl, 2-hexynyl, 3-hexynyl and the like.

The term cycloalkyl when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Furthermore, the substituents may either be in endo or exo positions in the bridged bicyclic systems.

The term "electron-withdrawing and electron donating" refer to the ability of a substituent to withdraw or donate electrons relative to that of hydrogen if the hydrogen atom occupied the same position in the molecule. These terms are well understood by one skilled in the art and are discussed in *Advanced Organic Chemistry*, by J. March, John Wiley and Sons, New York N.Y., pp. 16–18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl)amino, aryloxy such as phenoxy, mercapto, lower alkylthio, lower alkylmercapto, disulfide (lower alkyldithio) and the like. One skilled in the art will appreciate that the aforesaid substituents may have electron donating or electron withdrawing properties under different chemical conditions. Moreover, the present invention contemplates any combination of substituents selected from the above-identified groups.

The term halo includes fluoro, chloro, bromo, iodo and the like.

The term acyl includes lower alkanoyl.

As employed herein, the heterocyclic substituent contains at least one sulfur, nitrogen or oxygen, but also may include one or several of said atoms. The heterocyclic substituents contemplated by the present invention include heteroaromatics and saturated and partially saturated heterocyclic compounds. These heterocyclics may be monocyclic, bicyclic, tricyclic or polycyclic and are fused rings. They may contain up to 18 ring atoms and up to a total of 17 ring carbon atoms and a total of up to 25 carbon atoms. The heterocyclics are also intended to include the so-called benzoheterocycles. Representative heterocyclics include furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolidinyl, imidazolinyl, imidazolidinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the nitric oxides of pyridyl, pyrazinyl, and pyrimidinyl and the like. The preferred heterocyclic are thienyl, furyl, pyrroly, benzofuryl, benzothienyl, indolyl, methylpyrrolyl, merpholinyl, pyridyl, pyrazinyl, imidazolyl, pyrimidinyl, pyrazolyl or pyridazinyl. The preferred heterocyclic is a 5 or 6-membered heterocyclic compound. The especially preferred heterocyclic is furyl, pyridyl, pyrazinyl, imidazolyl, pyrazolyl, triazolyl, tetrazolyl, oxadiazolyl, epoxy, pyrimidinyl, or pyridazinyl. The most preferred heterocyclics are furyl, pyrazolyl, pyrrolyl and pyridyl.

The preferred compounds are those wherein n is 1, but di, tri and tetrapeptides are also contemplated to be within the scope of the claims.

The preferred values of R is aryl lower alkyl, especially benzyl, and the preferred $R_1$ is H or lower alkyl. The most preferred $R_1$ group is methyl.

The most preferred electron donating substituent and electron withdrawing substituent are halo, nitro, alkanoyl, formyl, arylalkanoyl, aryloyl, carboxyl, carbalkoxy, carboxamide, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl)amino, amine lower alkyl mercapto, mercaptoalkyl, alkylthio; and alkyldithio. The term "sulfide" encompasses mercapto, mercapto alkyl and alkylthio, while the term disulfide encompasses alkyldithio. These preferred substituents may be substituted on any one of $R_1$, $R_2$, $R_3$, $R_4$, $R_5$ or $R_6$, $R_7$ or $R_8$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino, alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NCR$_{18}$)OH wherein R$_{18}$ is lower alkyl], N-lower alkyl-O-lower alkyl hydroxyamino, i.e., [N(R$_{18}$)OR$_{19}$ wherein R$_{18}$ and R$_{19}$ are independently lower alkyl] and o-hydroxylamino (—O—NH$_2$); alkylamido such as acetamido, trifluoroacetamido, lower alkoxyamino, (e.g. NH(OCH$_3$); and heterocyclicamino, such as pyrazoylamino.

Furthermore, in still another embodiment Z may be O, S, NR$_4$ or PR$_4$ and Y may be hydrogen, lower alkyl or aryl and R, R$_1$, R$_2$, R$_3$, R$_4$, R$_5$, R$_6$, R$_7$, R$_8$, n and a are as defined hereinabove.

In a still further embodiment, ZY may be

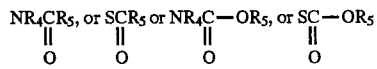

and R, R$_1$, R$_2$, R$_3$, R$_4$, R$_5$, R$_6$, R$_7$, R$_8$, n and a are as defined hereinabove.

When R$_2$ or R$_3$ is heterocyclic, the preferred heterocyclics are furyl, tetrahydrofuryl, pyridyl, pyrazinyl, imidazolyl, pyrazolyl, triazolyl, tetrazolyl, oxadiazolyl or epoxy. The most preferred heterocyclic is furyl, pyridyl, pyrazoyl and pyrrolyl.

The preferred heterocyclic groups representative of R$_2$ and R$_3$ have the formula

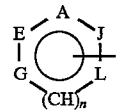

or those corresponding partially or fully saturated form thereof wherein n is 0 or 1

A, Z, L and J are independently CH, or a heteroatom selected from the group consisting of N, O, S, and G is CH, or a heteroatom selected from the group consisting of N, O and S, but when n is O, G is CH, or a heterocyclic selected from the group consisting of NH, O and S with the proviso that at most two of A, E, L, J and G are heteroatoms.

If the ring depicted hereinabove contains a nitrogen ring atom, then the N-oxide forms are also contemplated to be within the scope of the invention.

When R$_2$ or R$_3$ is a heterocyclic of the above formula, it may be bonded to the main chain by a ring carbon atom. When n is O, R$_2$ or R$_3$ may additionally be bonded to the main chain by a nitrogen ring atom.

R$_2$ or R$_3$ may independently also be SO$_3^-$, or SO$_2^-$.

Furthermore, ZY may also be

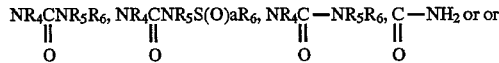

When R$_2$ is alkenyl the alkenyl group is a lower alkenyl group having 1–6 carbon atoms. The alkenyl group may be substituted with an electron donating group and more preferably with an electron withdrawing group, such as COOH.

As indicated hereinabove, Q and A may be O or S; in other words, the main chain may contain only C=O, only —C=S or combinations thereof. All such permutations are contemplated herein. It is preferred that the compounds of the present invention contain no more than 2 C=S moieties, it is even more preferred that the compounds of the present invention contain no more than 1 C=S moiety. The most preferred embodiment are when A and Q are both oxygen.

An embodiment of the present application is one in which the compounds are of Formula I wherein R is lower cycloalkyl or lower cycloalkyl lower alkyl, and R is unsubstituted or is substituted with at least one electron withdrawing group or electron donating group and R$_1$, R$_2$, R$_3$, Z, Y or ZY taken together, R$_4$, R$_5$, R$_6$, R$_7$, R$_8$, n and a are as defined herein.

Another embodiment of the present invention include compounds of Formula I wherein R$_1$ is lower cycloalkyl or lower cycloalkyl lower alkyl and R$_1$ may be unsubstituted or substituted with an electron donating group or electron withdrawing group and R$_1$, R$_2$, R$_3$, Z, Y, or ZY taken together, R$_4$, R$_5$, R$_6$, R$_7$, R$_8$ n and a are as defined hereinabove.

Another embodiment of the present invention includes compounds of Formula I wherein R$_2$ is lower cycloalkyl or lower cycloalkyl lower alkyl and R$_2$ may be unsubstituted or substituted with an electron donating group or electron withdrawing group, and R, R$_1$, R$_3$, R$_4$, R$_5$, R$_6$, R$_7$, R$_8$ and a are as defined hereinabove.

Still another embodiment of the present invention include compounds of Formula I wherein R$_3$ is lower cycloalkyl or lower cycloalkyl lower alkyl and R$_3$ may be unsubstituted or substituted with an electron donating or electron withdrawing group and R, $R_1$, $R_2$, $R_4$, $R_5$, $R_6$, $R_7$, $R_8$, n and a are as defined hereinabove.

A further embodiment of the present invention include compounds of Formula I wherein Z is $S(O)_a$ and R, $R_1$, $R_2$, $R_3$, Y, $R_4$, $R_5$, $R_6$, $R_7$, $R_8$, n and a are as defined herein.

It is preferred that one of $R_2$ and $R_3$ is hydrogen.

In a preferred embodiment, one of $R_2$ and $R_3$ is hydrogen and that the other is heterocyclic. It is preferred that one of $R_2$ and $R_3$ is a heterocyclic having Formula XI. The preferred heterocyclics include furyl, thienyl, benzothienyl, benzofuryl, oxazolyl, thiazolyl, isoxazolyl, indolyl, pyrazolyl, isoxazolidinyl, benzothienyl, benzofuryl, morpholinyl, indolyl, pyrrolyl, furfuryl, and methylpyrrolyl, pyridyl, pyrazinyl, imidazolyl, pyrimidinyl or pyridazinyl, pyrazolyl, or epoxy. In another preferred embodiment, one of $R_2$ and $R_3$ is alkyl (e.g. methylisopropyl), aryl (e.g., phenyl), 2-thiomethylethyl, lower alkoxy (e.g., ethoxy, methoxy), anilino, propenyl, alkylamino (e.g., ethylamino or methylamino). In another preferred embodiment, one of $R_2$ and $R_3$ is hydrogen and the other is heterocyclic lower alkyl, lower alkenyl, amino, lower alkoxy amino, N-lower alkylhydroxyamino, lower alkoxyamino, N-lower alkyl-O-lower alkylhydroxyamino or aralkoxycarbonylhydrazino.

Preferred compounds of the present invention have the following general formula:

$$A_m\text{—}\boxed{\phantom{X}}\text{—}CH_2NHC\underset{\underset{O}{\|}}{\text{—}}\underset{R_3}{\overset{R_2}{\underset{|}{C}}}NHC\underset{\underset{O}{\|}}{\text{—}}R_1$$

wherein $R_1$ is H or lower alkyl, $R_2$ and $R_3$ are as defined above and A is hydrogen or an electron donating group or electron-withdrawing group and m is 0–5. It is preferred that A is hydrogen (i.e., m=0). However, values of m equalling 1, 2 or 3 are also preferred.

Preferred embodiments include compounds of Formula I $$R\text{—}NH\text{—}\underset{\underset{Q}{\|}}{C}\text{—}\underset{R_3}{\overset{R_2}{\underset{|}{C}}}NH\text{—}_n\underset{\underset{A}{\|}}{C}\text{—}R_1 \quad (I)$$

wherein

R and $R_1$, independently, are hydrogen, lower alkyl, lower alkenyl, lower alkynyl, aryl lower alkyl, aryl, heterocyclic, lower alkyl heterocyclic, each unsubstituted or substituted with at least one substituent;

$R_2$ and $R_3$, independently, are hydrogen, lower alkyl, lower alkenyl, lower alkynyl, aryl lower alkyl, aryl, heterocyclic, lower alkyl heterocyclic, each unsubstituted or substituted with at least one substituent; halogen or a heteroatom containing oxygen, nitrogen, sulfur or phosphorous substituted with hydrogen, lower alkyl or aryl, said lower alkyl or aryl groups being substituted or unsubstituted; and n is 1 to 4.

Another preferred embodiment is a compound having Formula I $$R\text{—}NH\text{—}\underset{\underset{Q}{\|}}{C}\text{—}\underset{R_3}{\overset{R_2}{\underset{|}{C}}}NH\text{—}_n\underset{\underset{O}{\|}}{C}\text{—}R_1 \quad (I)$$

wherein

R is aryl, aryl lower alkyl, heterocyclic, lower alkyl heterocyclic, polynuclear aromatic or lower alkyl polynuclear aromatic, each unsubstituted or substituted with at least one electron withdrawing substituent or at least one electron donating substituent;

$R_1$ is H or lower alkyl, unsubstituted or substituted with at least one electron withdrawing substituent or at least one electron donating substituent;

$R_2$ and $R_3$, independently, are hydrogen, lower alkyl, lower alkenyl, lower alkynyl, aryl, aryl lower alkyl, heterocyclic, lower alkyl heterocyclic, polynuclear aromatic, lower alkyl polynuclear aromatic, each unsubstituted or substituted with at least one electron donating substituent, halogen or a heteroatom containing oxygen, nitrogen, sulfur or phosphorous substituted with hydrogen, lower alkyl or aryl, said lower alkyl or aryl groups being substituted or unsubstituted; and n is 1 to 4.

Another preferred embodiment of the present invention is a compound of Formula I $$R\text{—}NH(C\text{—}CNH)_n\text{—}\underset{\underset{O}{\|}}{C}\text{—}R_1$$
(with substituents $R_2$, Q, $R_3$)

wherein

R is aryl lower alkyl, heterocyclic, lower alkyl heterocyclic, polynuclear aromatic or lower alkyl polynuclear aromatic, each of which may be unsubstituted or substituted with at least one halo, nitro, acyl, carboxyl, carboalkoxy, carboxamide, cyano, sulfonyl, sulfoxide (sulfinyl), heterocyclic, guanidine, quaternary ammonium hydroxy, alkoxy, alkyl, amino, phenoxy, mercapto, sulfide or disulfide;

$R_1$ is H or lower alkyl which may be unsubstituted or substituted with at least one halo, nitro, acyl, carboxamide, cyano, sulfonyl, sulfoxide (sulfinyl), heterocyclic, guanidine, quaternary ammonium, hydroxy, lower alkoxy, amino, phenoxy, sulfide, or disulfide;

$R_2$ is hydrogen, lower alkyl, lower alkenyl, lower alkynyl, aryl, heterocyclic, lower alkyl heterocyclic, polynuclear aromatic, lower alkyl polynuclear aromatic, each unsubstituted or substituted with at least one electron withdrawing substituent or at least one electron donating substituent; halogen or a heteroatom consisting of oxygen, nitrogen, sulfur or phosphorous, said heteroatom being substituted with hydrogen, lower alkyl or aryl, said lower alkyl or aryl groups being substituted or unsubstituted;

$R_3$ is hydrogen, lower alkyl, lower alkenyl, lower alkynyl, aryl, heterocyclic, lower alkyl heterocyclic, polynuclear aromatic, lower alkyl polynuclear aromatic, each unsubstituted or substituted with at least one electron withdrawing substituent or at least one electron donating substituent; halogen or a heteroatom consisting of oxygen, nitrogen, sulfur, or phosphorous said heteroatom being substituted with hydrogen, lower alkyl or aryl, said lower alkyl of aryl groups being substituted or unsubstituted;

and n is 1 to 4;

Another preferred embodiment is a compound of Formula I

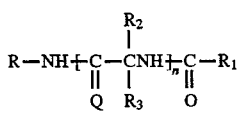

(I)

wherein

R is aryl, aryl lower alkyl, heterocyclic or heterocyclic lower alkyl and R is unsubstituted or is substituted with at least one electron withdrawing group, or electron donating group;

$R_1$ is hydrogen or lower alkyl, unsubstituted or substituted with an electron donating group or an electron withdrawing group and $R_2$ and $R_3$ are independently hydrogen, lower alkyl, lower alkenyl, lower alkynyl, aryl lower alkyl, aryl, heterocyclic, heterocyclic lower alkyl, or Z—Y wherein $R_2$ and $R_3$ may be unsubstituted or substituted with at least one electron withdrawing group or electron donating group;

Z is O, S,S(O)$_a$, NR$_4$, PR$_4$ or a chemical bond;

Y is hydrogen, lower alkyl, aryl, aryl lower alkyl, lower alkenyl, lower alkynyl, heterocyclic, heterocyclic lower alkyl, or halo and Y may be unsubstituted or substituted with an electron donating group or an electron withdrawing group, provided that when Y is halo, Z is a chemical bond, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$ or PR$_4$SR$_7$, NR$_4$PR$_5$R$_6$ or PR$_4$NR$_5$R$_7$,

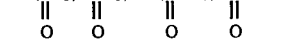

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group and $R_7$ is $R_6$ or COOR$_8$ or COR$_8$, $R_8$ is hydrogen or lower alkyl, or aryl lower alkyl, wherein the aryl or lower alkyl groups may be unsubstituted or substituted with an electron withdrawing or electron donating group, n is 1–4 and a is 1–3.

Another class of preferred compounds of the Formula I have the formula

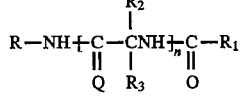

wherein

R is aryl, aryl lower alkyl, heterocyclic or heterocyclic alkyl which is unsubstituted or substituted with at least one electron withdrawing group or at least one electron donating group;

$R_1$ is hydrogen or lower alkyl which is unsubstituted or substituted with at least one electron withdrawing group or one electron donating group, $R_2$ and $R_3$ are independently hydrogen, lower alkenyl, lower alkynyl, aryl, aryl lower alkyl, Z—Y or a heterocyclic group which may be unsubstituted or substituted with at least one electron withdrawing or one electron donating group, with the proviso that $R^2$ and $R^3$ cannot both be hydrogen;

Z is O, S, NR$_4$, PR$_4$ or a chemical bond;

Y is hydrogen, lower alkyl, aryl, aryl lower alkyl, lower alkenyl, lower alkynyl or halo, and Y may be unsubstituted or substituted with an electron donating group or an electron withdrawing group, provided that when Y is halo, Z is a chemical bond; or ZY taken together is NR$_4$NR$_5$R$_6$, NR$_4$OR$_5$, ONR$_4$R$_5$, OPR$_4$R$_5$, PR$_4$OR$_5$, SNR$_4$R$_5$, NR$_4$SR$_5$, SPR$_4$R$_5$, or PR$_4$SR$_5$, NR$_4$PR$_5$R$_6$ or PR$_4$NR$_5$R$_6$, $R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group;

n is 1–4.

Of this preferred group, it is especially preferred that n is 1.

The preferred compounds are those in which R is aryl, aryl lower alkyl, heterocyclic, or heterocyclic lower alkyl, $R_1$ is hydrogen or lower alkyl, $R_2$ and $R_3$ are independently hydrogen, heterocyclic, lower alkyl, aryl, lower alkoxy, lower alkenyl, amino, hydroxylamino, lower alkoxy amino, N-lower alkyl hydroxyamino, N-lower alkyl-o-lower alkyl hydroxyamino, aralkoxy carbonyl hydrazino or alkylmercapto and n is 1.

In another preferred embodiment, n is 1, R and $R_1$ are as defined hereinabove and one of $R_2$ and $R_3$ is hydrogen and the other is heterocyclic, heterocyclic lower alkyl, aryl N-hydroxylamino, lower alkoxyamino, N-lower alkylhydroxylamino, N-lower alkyl-O-lower alkylhydroxyamino.

Another preferred embodiment is wherein n is 1, R and $R_1$ are as defined hereinabove, one of $R_2$ and $R_3$ is as defined hereinabove or the other is heterocyclic, heterocyclic lower alkyl, lower alkyl heterocyclic, aryl, N-hydroxylamino, lower alkoxy amino, N-lower alkyl hydroxylamino, N-lower alkyl-o-lower alkyl hydroxylamino, lower alkoxy, dialkyl lower amino, lower alkylamino, aryl lower alkyloxy hydrazino, or lower alkylmercapto.

The various combination and permutations of the Markush groups of $R_1$, $R_2$, $R_3$ R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$ and R with respect to each value of n.

The compounds of the present invention may contain one (1) or more asymmetric carbons and may exist in racemic and optically active forms. The configuration around each asymmetric carbon can be in either the D or L form. (It is well known in the art that the configuration around a chiral carbon atoms can also be described as R or S in the Cahn-Prelog-Ingold nomenclature system). All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atoms to which the groups $R_2$ and $R_3$ are attached as substituted. When n is 1, the compounds of the present invention is of the formula $$R-NH-\underset{\underset{O}{\|}}{\overset{\overset{R_2}{|}}{C}}-\underset{\underset{R_3}{|}}{\overset{\overset{H}{|}}{C}}-\underset{}{\overset{\overset{O}{\|}}{N}}-C-R_1$$

wherein R, $R_1$, $R_2$, $R_3$, $R_4$, $R_5$, $R_6$, Z and Y are as defined previously. As used herein, the term configuration shall refer to the configuration around the carbon atom to which $R_2$ and $R_3$ are attached, even though other chiral centers may be present in the molecule. Therefore, when referring to a particular configuration, such as D̲ or L̲, it is to be understood to mean the stereoisomer, including all possible enantiomers and diastereomers. The compounds of the present invention are directed to all of the optical isomers, i.e., the compounds of the present invention are either the L̲-stereoisomer or the D̲-stereoisomer. These stereoisomers may be found in mixtures of the L̲ and D̲ stereoisomer, e.g., racemic mixtures. The D̲ stereoisomer is preferred.

Depending upon the substituents, the present compounds may form addition salts as well. All of these forms are contemplated to be within the scope of this invention including mixtures of the stereoisomeric forms.

The following three schemes of preparation are generally exemplary of the process which can be employed for the preparation of the present complex. Although the compounds in the schemes hereinabove contain only the $$\overset{C}{\underset{O}{\|}}$$

moiety, it is just as applicable to compounds of Formula I wherein either A or Q is sulfur or both A or Q are sulfur.

Scheme I $$HOOC-\underset{\underset{R_3}{|}}{\overset{\overset{R_2}{|}}{C}}-NH_2 \xrightarrow[MeOH]{SOCl_2} \xrightarrow[RNH_2]{excess}$$

$$R-NH-\underset{\underset{O}{\|}}{\overset{\overset{R_2}{|}}{C}}-\underset{\underset{R_3}{|}}{\overset{}{C}}-NH_2 \xrightarrow{R_1C-O-C-R_1}$$

$$RNH-\underset{\underset{O}{\|}}{\overset{\overset{R_2}{|}}{C}}-\underset{\underset{R_3}{|}}{\overset{}{C}}-NH-\underset{\underset{O}{\|}}{\overset{}{C}}-R_1$$

Scheme II $$HOOC-\underset{\underset{R_3}{|}}{\overset{\overset{R_2}{|}}{C}}-NH_2 \xrightarrow{R_1COCR_1} HOOC-\underset{\underset{R_3}{|}}{\overset{\overset{R_2}{|}}{C}}-NH-\overset{\overset{O}{\|}}{C}R_1$$

$$\downarrow \underset{tertiary\ amine}{\overset{\overset{O}{\|}}{ClCOR_{17}}}$$

-continued
Scheme II $$RNH-\overset{\overset{O}{\|}}{C}-\underset{\underset{R_3}{|}}{\overset{\overset{R_2}{|}}{C}}-NHCR_1 \xleftarrow{RNH_2} R_{17}OCOC-\underset{\underset{R_3}{|}}{\overset{\overset{R_2}{|}}{C}}-NH-\overset{\overset{O}{\|}}{C}R_1$$

$$+$$

$$CO_2 + R_{17}OH$$

wherein $R_{17}$=lower alkyl, aryl, aryl lower alkyl,

Scheme III $$R_1CNH_2 \xrightarrow{R_2CCOH} R_1CNH-\underset{\underset{R_2}{|}}{\overset{\overset{OH}{|}}{C}}-COH$$

$$\downarrow R_{17}OH/H^+$$

$$R_1CNH-\underset{\underset{R_2}{|}}{\overset{\overset{OR_{17}}{|}}{C}}-CNHR \xleftarrow[\text{with or without catalyst (i. e., M}^+\text{CN}^-)]{RNH_2} R_1CNH-\underset{\underset{R_2}{|}}{\overset{\overset{OR_{17}}{|}}{C}}-COR_{17}$$

$$\downarrow \underset{\text{Lewis acid, such as BF}_3\text{-O(Et)}_2}{R_3H}$$

$$R_1CNH-\underset{\underset{R_2}{|}}{\overset{\overset{R_3}{|}}{C}}-CNHR$$

wherein $R_3$=aryl, heteroaromatic and $R_{17}$ is as defined hereinabove.

More specificically these compounds can be prepared by art-recognized procedures from known compounds or readily preparable intermediates. For instance, compounds of Formula I can be prepared by reacting amines of Formula II with an acylating derivative of a carboxylic acid of Formula III under amide forming conditions:

$$RNH-\left[\overset{\overset{O}{\|}}{C}-\underset{\underset{R_3}{|}}{\overset{\overset{R_2}{|}}{C}}-NH\right]_n-H + R_1-\overset{\overset{O}{\|}}{C}-OH \longrightarrow I$$

II              III wherein R, $R_1$, $R_2$, $R_3$ and are as defined hereinabove and n=1.

The amide forming conditions referred to herein involve the use of known derivatives of the described acids, such as the acyl halides, (e.g., $$R_1-\overset{\overset{O}{\|}}{C}-X,$$

wherein X is Cl, Br and the like), anhydrides (e.g.,

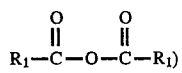

mixed anhydrides, lower alkyl esters, carbodiimides, carbonyldiimidazoles, and the like. It is preferred that the acylating derivative used is the anhydride,

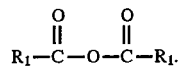

When alkyl esters are employed, amide bond formation can be catalyzed by metal cyanides such as sodium or potassium cyanides.

Another exemplary procedure for preparing compounds wherein at least one of $R_2$ and $R_3$ is aromatic or heteroaromatic is depicted in Scheme IV.

The ester (IV) is reacted with halogen and ultraviolet light in the presence of a catalyst, e.g., AIBN, to form the halo derivative (V). (V) is reacted in the presence of a Lewis acid, such as zinc chloride, with an aromatic or heteroaromatic compound to form the compound (VI). (VI) in turn is hydrolyzed and then reacted with alkylhaloformate, such as alkylchloroformate in the presence of a tertiary amine to generate the mixed N-acyl amino acid carbonic ester anhydride (VIII). This intermediate is reacted with an amine under amide forming conditions to give the compound of Formula I. Alternatively, (VI) can be reacted directly with an amine ($RNH_2$) optionally in the presence of a metal catalyst, such as metal cyanides, e.g., potassium or sodium cyanide, under amide forming conditions to form a compound of Formula I. Alternatively, compound VIII can be prepared by an independent method and converted to VI which is then reacted with an amine, with or without catalyst to form the compound of Formula I.

Scheme IV

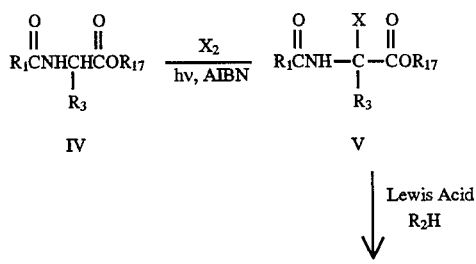

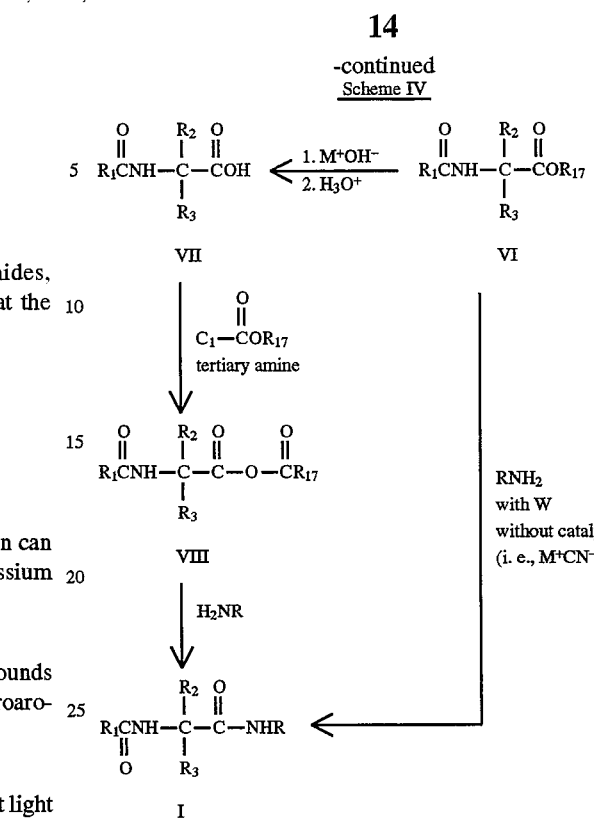

X=halogen (i.e., Cl, Br)
$R_{17}$=lower alkyl, aryl, arly lower alkyl
M+=metal cation (i.e., $Na^+$, $K^+$)

Two additional synthetic routes may be employed for the preparation of compounds wherein $R_2$ or $R_3$ is Z—Y as defined hereinabove. In one scheme, for the preparation of these complexes, a substitution reaction is used:

Scheme V

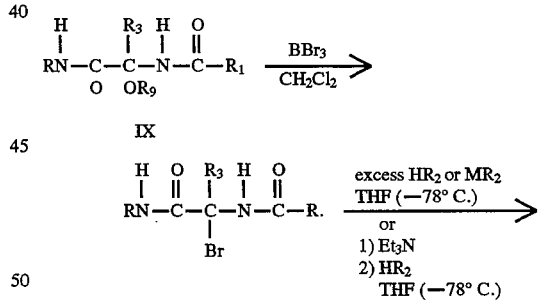

compound of Formula I,

In the above scheme, $R_9$ is lower alkyl, $R_2$ is Z—Y and Z, Y, R, $R_3$ and $R_1$ are as defined hereinabove.

The ether functionality on IX can be cleaved by treatment with Lewis acids, such as $BBr_3$ in an inert solvent such as methylene chloride to form the corresponding halo (bromo) derivative. Addition of either an excess of the H—$R_2$ or M$R_2$ or the sequential addition of triethylamine and H—$R_2$ to a THF mixture containing the halo derivative furnishes the desired product. For example, in the case wherein the compound of Formula IX is 2-acetamido-N-benzyl-2-ethoxy acetamide, its treatment with BBr₃ in CH₂Cl₂ led to the formation of the α-bromo derivative, 2-acetamido-N-benzyl-2-bromoacetamide. Addition of an excess of HR₂ or the sequential addition of HR₂ to a THF mixture containing the bromo adduct furnishes the desired product.

In another procedure, the product wherein R₂ or R₃ is Z—Y can also be prepared by substitution reaction on a quaternary ammonium derivative of the compound of Formula I as outlined below Scheme VI

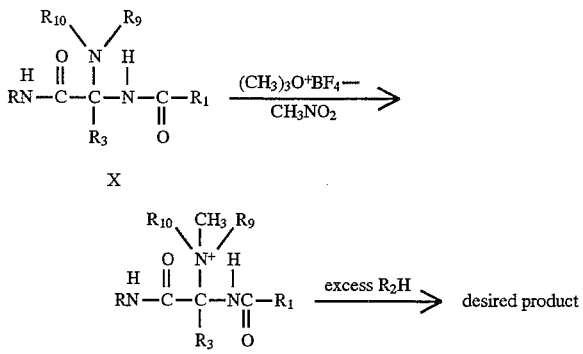

X

In scheme VI, R, R₁, R₃ and R are as defined hereinabove, R₂ is Z—Y and R₉ and R₁₀ are independently lower alkyl. In scheme VI, methylation of compound X with a methylation reagent, such as trimethyloxonium tetrafluoroborate provided the corresponding ammonium derivative. Subsequent treatment of the ammonium salt with HR₂ furnishes the desired product. For example, methylation of 2-acetamido-N-benzyl-2-(N,N-dimethylamino)acetamide with trimethyloxonium tetrafluoroborate in nitromethane furnished the quaternary ammonium derivative, 2-acetamido-N-benzyl-(N,N,N-trimethylammonium) acetamide tetrafluoroborate in high yields. Subsequent treatment of the salt with the HR₂ reagent in the methanol leads to the production of the desired product.

As in any organic reaction, solvents can be employed such as methanol, ethanol, propanol, acetone, tetrahydrofuran, dioxane, dimethylformamide, dichloromethane, chloroform, and the like. The reaction is normally effected at or near room temperature, although temperatures from 0° C. up to the reflux temperature of the reaction mixture can be employed.

As a further convenience, the amide forming reaction can be effected in the presence of a base, such as tertiary organic amine, e.g., triethylamine, pyridine, 4-methylmorpholine, picolines and the like, particularly where hydrogen halide is formed by the amide forming reaction, e.g., the reaction acyl halide and the amine of Formula II. Of course, in those reactions where hydrogen halide is produced, any of the commonly used hydrogen halide acceptors can also be used.

The exact mineral acid or Lewis acid employed in the reaction will vary depending on the given transformation, the temperature required for the conversion and the sensitivity of the reagent toward the acid in the reaction employed.

Compounds of the present invention in which Q or A is S are prepared from the corresponding compounds in which Q or A is O by art recognized techniques. For example, one reagent that can be used is Lawesson's reagent, i.e., [2,4-bis-(4-methoxyphenyl)-1,3-dithia-2,4-diphosphetane-2-,4-disulfide]. This reagent is a known reagent for the thiation of such compounds as ketones, carboxamides, esters, lactones, lactams, imides, enamines, and S-substituted thioesters. Thus, this reagent can be used to transform compounds of Formula I wherein Q or A is O to compounds wherein one or both of Q or A is S. The number of $$\begin{matrix} C \\ \| \\ S \end{matrix}$$

groups in the final product is dependent upon the amount of reagent added and the number of $$\begin{matrix} C \\ \| \\ O \end{matrix}$$

groups present (i.e., the value of n) in the reactants having Formula I. For example, if n is 1, and both Q and A are oxygen, than the compounds of Formula I have two $$\begin{matrix} C \\ \| \\ O \end{matrix}$$

groups. Thus, if it is desired that both $$\begin{matrix} C \\ \| \\ O \end{matrix}$$

groups be transformed to $$\begin{matrix} C \\ \| \\ S \end{matrix}$$

then approximately equimolar amount or a slight excess of is added to compounds of Formula I. On the other hand, if only one $$\begin{matrix} C \\ \| \\ S \end{matrix}$$

group is desired in the final product, then approximately ½ molar equivalent of Lawesson's reagent is used.

Furthermore, it is not necessary to add the reagent at the last step of the synthesis; the reagent can be added at any stage of the syntheses outlined in Schemes I–VI hereinabove. As before, the amount of the reagent added depends upon the number of $$\begin{matrix} C \\ \| \\ S \end{matrix}$$

desired in the product, and the number of $$\begin{matrix} C \\ \| \\ O \end{matrix}$$

groups in the reactant.

Regardless of which step in the synthesis the reagent is added, the reagent and the compound of Formula I having at least one $$\underset{\text{O}}{\overset{\text{C}}{\|}}$$

group or an intermediate thereof is dissolved in an inert solvent, such as THF and heated at a temperature effective to convert the $$\underset{\text{O}}{\overset{\text{C}}{\|}}$$

group to $$\underset{\text{S}}{\overset{\text{C.}}{\|}}$$

Temperatures ranging from room temperature to the reflux temperature of the solvent can be used. In cases when n=1, it is preferred that the reaction is heated to about reflux if both Q and A are converted to S and that about room temperature be used if one of Q or A is converted to S.

The various substituents on the present new compounds, e.g., as defined in R, $R_1$, $R_2$ and $R_3$ can be present in the starting compounds, added to any one of the intermediates or added after formation of the final products by the known methods of substitution or conversion reactions. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can be then transformed to the corresponding alkyl groups by various methods, including the Woff-Kishner reduction and Clemmenson reduction. Amino groups can be alkylated to form mono, dialkylamino and trialkylamino groups; and mercapto and hydroxy groups can be alkylated to form corresponding thioethers or ethers, respectively. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

In the above reactions, if the substituents themselves are reactive, then the substituents can themselves be protected according to the techniques known in the art. A variety of protecting groups known in the art may be employed. Examples of many of these possible groups may be found in "Protective Groups in Organic Synthesis," by T. W. Greene, John Wiley & Sons, 1981.

Resulting mixtures of isomers can be separated in the pure isomers by methods known to one skilled in the art, e.g., by fractional distillation, crystallization and/or chromotagraphy.

The present compounds obviously exist in stereoisomeric forms and the products obtained thus can be mixtures of the isomers, which can be resolved. Optically pure functionalized amino acid derivatives can be prepared directly from the corresponding pure chiral intermediate. Racemic products can likewise be resolved into the optical antipodes, for example, by separation of diastereomeric salts thereof, e.g., by fractional crystallization, by selective enzymatic hydrolysis, e.g., papain digestion, or by use of a chiral stationary phase in chromotagraphy (HPLC). For a discussion of chiral stationary phases for HPLC, See, DeCamp, *Chirality*, 1, 2–6 (1989), which is incorporated herein by reference with the same force and effect as if fully set forth herein.

For example, a racemic mixture of any of the intermediate in any of the schemes, e.g.,

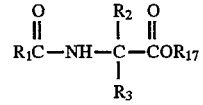

wherein $R_{17}$ is H (which can be prepared according to the procedures of Schemes 1, 2, 3 or 4) is reacted with an optically active amine, $RNH_2$, e.g., $(R)(+)\alpha$-methylbenzylamine to form a pair of diasteroomeric salts. Diastereomers can then be separated by recognized techniques known in the art, such as fractional recrystallization and the like.

In another method, a racemic mixture of final products or intermediates can be resolved by using enzymatic methods. Since enzymes are chiral molecules, it can be used to separate the racemic modification, since it will preferentially act on one of the compounds, without affecting the enantiomer. For example, acylase, such as acylase I, can be used to separate the racemic modification of an intermediate D,L($\pm$)α-acetamido-2-furanacetic acid. It acts on the L ($\pm$)α-acetamido-2-furanacetic acid, but will not act on the D acetamido-2-furanacetic acid. In this way, the D(–)α-acetamido-2-furanacetic acid can be isolated. The intermediate can then react with the amine ($RNH_2$) under amide forming conditions as described hereinabove to form the compound of Formula I.

The active ingredients of the therapeutic compositions and the compounds of the present invention exhibit excellent anticonvulsant activity when administered in amounts ranging from about 10 mg to about 100 mg per kilogram of body weight per day. A preferred dosage regimen for optimum results would be from about 20 mg to about 50 mg per kilogram of body weight per day, and such dosage units are employed that a total of from about 1.0 gram to about 3.0 grams of the active compound for a subject of about 70 kg of body weight are administered in a 24-hour period. This dosage regimen may be adjusted to provide the optimum therapeutic response and is preferably administered one to three times a day in dosages of about 600 mg per administration. For example, several divided doses may be administered daily or the dose may be proportionally reduced as indicated by the exigencies of the therapeutic situation. A decided practical advantage is that the active compound may be administered in an convenient manner such as by the oral, intraveneous (where water soluble), intramuscular or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained.

Preferred compositions or preparations according to the present invention are prepared so that an oral dosage unit form contains between about 5 and 1000 mg of active compound.

The tablets, troches, pills, capsules and the like may also contain the following: A binder such as gum tragacanth, acacia, corn starch or gelatin; excipients such as dicalcium phosphate; a disintergrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoncally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 250 to about 750 mg being preferred. Expressed in proportions, the active compound is generally present in from about 10 to about 750 mg/ml of carrier. In the case of compositions containing supplementary active ingredients, the dosages are determined by reference to the usual dose and manner of administration of the said ingredients.

The compounds of the present invention may be administered in combination with other anti-convulsant agents, such as phenytoin, phenbarbitol, mephenytoin, and phenacemide, and the like. This combination is likely to exhibit synergistic effects.

For a better understanding of the present invention together with other and further objects, reference is made to the following description and examples.

General Methods.

Melting points were determined with a Thomas-Hoover melting point apparatus and are uncorrected. Infrared spectra (IR) were run on a Beckman IR-4250 and Perkin-Elmer 1330 and 283 spectrophotometers and calibrated against the 1601-cm$^{-1}$ band of polysytrene. Absorption values are expressed in wavenumbers (cm$^{-1}$). Proton nuclear magnetic resonance ($^1$H NMR) spectra were recorded on Varian Associates Models T-60 and FT-80A, General Electric QE 300, and Nicolet NT-300 NMR spectrometers. Carbon nuclear magnetic resonance ($^{13}$C NMR) spectra were run on a Varian Associates Models FT-80A General Electric QE 300 and Nicolet NT-300 instrument. Chemical shifts are in parts per million (δ values) relative to Me$_4$Si, and coupling constants (J values) are in hertz. Mass spectral data were obtained at an ionizing voltage of 70 eV on a Hewlett- Packard 5930 gas chromotagraph-mass spectrometer and a Bell-Howell 21–491 spectrometer as well as at the Eli Lilly Laboratories on a Varian MAT-CH-5 spectrometer. High-resolution (EI mode) mass spectra were performed by Drs. James Hudson and John Chinn at the Department of Chemistry, University of Texas at Austin, on a CEC21-110B double-focusing magnetic-sector spectrometer at 70 eV. Elemental analyses were obtained at Spang Microanalytical Laboratories, Eagle Harbor, Mich. and at the Eli Lilly Research Laboratories.

The solvents and reactants were of the best commercial grade available and were used without further purification unless noted. All anhydrous reactions were run under nitrogen, and all glassware was dried before use. In particular, acetonitrile and triethylamine were distilled from $CaH_2$, while dichloromethane was distilled from $P_2O_5$. Acetic anhydride, benzaldehyde and ethyl chloroformate were fractionally distilled.

Preparation of N-Acetyl-D- and L-amino acid-N-benzylamides.

General Procedure.

The D- or L-amino acid amide (11 mmol) was dissolved in dichloromethane (15 mL) and then acetic anhydride (1.23 g, 1.40 mL, 12 mmol) was added dropwise. The solution was stirred at room temperature (18 h) and then concentrated to dryness. The residue was recrystallized from chloroform/hexane. The following examples 1–7 were prepared according to this procedure.

EXAMPLE 1

Preparation of N-Acetyl-D,L-alanine-N'-benzylamide.

Acetic anhydride (2.20 g, 0.022 mol) was slowly added to a methylene chloride solution (30 mL) of D,L-alanine-N-benzylamide (3.80 g, 0.021 mol) and allowed to stir at room temperature (3 h). The mixture was then successively washed with $H_2O$ (15 mL), 1% aqueous NaOH (15 mL) and $H_2O$ (15 mL), dried ($Na_2SO_4$) and concentrated in vacuo. The residue was recrystallized from $CH_2Cl_2$.

Yield: 2.50 g (54%).

mp 139°–141° C.

$^1$H NMR (DMSO-$d_6$): δ 1.22 (d,J=7.1 Hz, 3H), 1.84 (s, 3H), 4.04–4.50 (m, 3H), 7.26 (s, 5H), 8.11 (br d,J=7.3 Hz, 1H), 8.42 (br t,J=6 Hz, 1H).

$^{13}$C NMR (DMSO-$d_6$): 18.2, 22.4, 41.9, 48.2, 126.5, 126.9, 128.1, 139.4, 168.9, 172.4 ppm.

IR (CHCl$_3$) 3440, 3300, 3005, 1660, 1515 cm$^{-1}$.

Mass spectrum (CI mode), m/e: 221 (P+1); mol wt 220.1208 (Calculated for $C_{12}H_{16}N_2O_2$, 220.1212).

EXAMPLE 2

N-Acetyl-D-alanine-N'-benzylamide.

Yield: 1.36 g (56%).

mp 139°–141° C.

$[α]_D^{23}$=+36.2 (c 2.5, MeOH).

$^1$H NMR (80 MHz, DMSO-$d_6$): δ 1.25 (d,J=7.1 Hz, 3H), 1.86 (s, 3H), 4.10–4.50 (m, 1H), 4.30 (d,J=6.0 Hz, 2H), 7.26 (s, 5H), 8.09 (d,J=7.3 Hz, 1H), 8.40 (t,J=6.0 Hz, 1H).

$^{13}$C NMR (80 MHz, DMSO-$d_6$): 18.3, 22.5, 42.0, 48.4, 126.6, 127.0 (2C), 128.2 (2C), 139.4, 169.2, 172.5 ppm.

IR (KBr): 3290, 1635 (br), 1540, 1455, 700, 695 cm$^{-1}$.

Mass spectrum, m/e (relative intensity): 221 (30), 114 (20), 106 (40), 91 (80), 87 (100), 77 (5), 72 (20), 65 (5).

Elemental analysis Calculated for $C_{12}H_{16}N_2O_2$ 65.42% C; 7.34% H; 12.72% N. Found 65.31% C; 7.28% H; 12.63% N.

EXAMPLE 3

N-Acetyl-L-alanine-N'-benzylamide.

Yield: 1.11 g (46%).

mp 139°–142° C.

$[α]_d^{23}$=–35.3 (c 2.5, MeOH).

$^1$H NMR (80 MHz, DMSO-$d_6$): δ 1.23 (d,J=7.2 Hz, 3H), 1.86 (s, 3H), 4.26–4.35 (m, 1H), 4.29 (d,J=5.8 Hz, 2H), 7.22–7.33 (s, 5H), 8.10 (d,J=7.4 Hz, 1H), 8.42 (t,J=5.8 Hz, 1H).

$^{13}$C NMR (80 MHz, DMSO-$d_6$): 18.3, 22.6, 42.0, 48.4, 126.7, 127.0 (2C), 128.3 (2C), 139.5, 169.2, 172.6 ppm.

IR (KBr): 3290, 1635 (br), 1545, 1450, 700, 695 cm$^{-1}$.

Mass spectrum, m/e (relative intensity): 221 (40), 114 (40), 106 (80), 106 (80), 91 (75), 87 (100), 77 (5), 72 (15), 65 (5).

Elemental analysis Calculated for $C_{12}H_{16}N_2O_2$ 65.42% C; 7.34% H; 12.72% N. Found 65.58% C; 7.32% H; 12.43% N.

EXAMPLE 4

Preparation of N-Acetyl-D,L-phenylglycine-N'-methylamide.

Acetic anhydride (2.90 g, 28 mmol) was added dropwise to D,L-phenylglycine-N-methylamide (3.4 g, 20 mmol) and allowed to stir at room temperature (1.5 h). During this time, a copious white precipitate formed. This material was collected by filtration, dried in vacuo and recrystallized from absolute alcohol.

Yield: 2.00 g (49%).

mp 232°–235° C. (dec).

$^1$H NMR (DMSO-$d_6$): δ 1.89 (s, 3H), 2.58 (d,J=4.6 Hz, 3H), 5.42 (d,J=8.1 Hz, 1H), 7.35 (s, 5H), 8.18 (br q,J=4.2 Hz, 1H), 8.47 (d,J=8.1 Hz, 1H).

$^{13}$C NMR (DMSO-$d_6$): 22.4, 25.5, 56.3, 127.1, 127.3, 128.1, 139.0, 168.9, 170.3 ppm.

IR (KBr): 3310, 1645 cm$^{-1}$.

Mass spectrum (CI mode), m/e: 207 (P+1).

Elemental analysis Calculated for $C_{11}H_{14}N_2O_2$ 64.06% C; 6.86% H; 13.58% N. Found 63.79% C; 6.66% H; 13.27% N.

EXAMPLE 5

Preparation of N-Acetylglycine-N-benzylamide.

The D,L-amino acid amide (11 mmol) was dissolved in dichloromethane (15 mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 1.84 g (81%).

mp 140°–142° C.

$^1$H NMR (DMSO-$d_6$): δ 1.88 (s, 3H), 3.74 (d,J=5.3 Hz, 2H), 4.30 (d,J=5.1 Hz, 2H), 7.27 (s, 5H), 8.37 (br s, 1H), 8.75 (br s, 1H).

$^{13}$C NMR (DMSO-$d_6$): 22.5, 42.0, 42.5, 126.6, 127.1 (2C), 128.1 (2C), 139.3, 169.0, 169.6 ppm.

IR (KBr): 3060, 1655, 1640, 1560, 1545, 1450, 1300, 740, 710 cm$^{-1}$.

Mass spectrum, m/e (relative intensity): 206 (3), 147 (12), 106 (100), 91 (75), 73 (50).

Elemental analysis Calculated for $C_{11}H_{14}N_2O_2$ 64.05% C; 6.86% H; 13.58% N. Found 64.03% C; 6.79% H; 13.61% N.

EXAMPLE 6

Preparation of N-Acetyl-D,L-valine-N-benzylamide.

The D,L-amino acid amide (11 mmol) was dissolved in dichloromethane (15 mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 2.35 g (86%).

mp 192°–193° C.

$^1$H NMR (DMSO-$d_6$): δ 0.83 (d,J=6.7 Hz, 6H), 1.87 (s, 3H), 1.73–2.09 (m, 1H), 4.11 (d,J=8.8 Hz, 1H), 4.27 (d,J=5.8 Hz, 2H), 7.26 (s, 5H), 7.89 (d,J=8.8 Hz, 1H), 8.84 (t,J=5.8 Hz, 1H).

$^{13}$C NMR (DMSO-$d_6$): 18.1, 19.2, 22.4, 30.2, 41.9, 57.8, 126.6, 127.1 (2C), 128.1 (2C), 139.4, 169.2, 171.1 ppm.

IR (KBr): 1625, 1540, 1535, 1450, 1380, 1290, 750, 695 cm$^{-1}$.

Mass spectrum, m/e (relative intensity): 142 (16), 114 (43), 106 (29), 91 (57), 72 (100).

Elemental analysis Calculated for $C_{14}H_{20}N_2O_2$ 67.70% C; 8.13% H; 11.28% N. Found 67.58% C; 8.05% H; 11.10% N.

EXAMPLE 7

Preparation of N-Acetyl-D,L-phenylglycine-N-benzylamide.

The D,L-amino acid amide (11 mmol) was dissolved in dichloromethane (15 mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 2.05 g (66%).

mp 202°–203° C.

$^1$H NMR (DMSO-$d_6$): δ 1.91 (s, 3H), 4.27 (d,J=5.6 Hz, 2H), 5.50 (d,J=7.9 Hz, 1H), 7.21 (s, 5H), 7.36 (s, 5H), 8.38–8.86 (m, 2H).

$^{13}$C NMR (DMSO-$d_6$): 22.3, 42.0, 56.3, 126.6 (2C), 127.0, 127.1 (2C), 127.4 (2C), 128.1 (2C), 138.9, 139.0, 168.9, 169.9 ppm.

IR (KBr): 3020, 1635, 1580, 1540, 1450, 1265, 745, 690 cm$^{-1}$.

Mass spectrum, m/e (relative intensity): 283 (20), 264 (21), 149 (100), 131 (20), 118 (34), 106 (92), 91 (70), 79 (56), 77 (54), 65 (45), 51 (37).

Elemental analysis Calculated for $C_{17}H_{18}N_2O_2$ 72.31% C; 6.44% H; 9.92% N. Found 72.49% C; 6.47% H; 9.89% N.

Preparation of N-Acetyl-D- and L-phenylglycine-N-benzylamide.

General Procedure.

The chiral Boc-protected phenylglycine-N-benzylamide was dissolved in trifluoroacetic acid (0.04M) and was stirred at room temperature (30 min), during which time gas evolved. The solution was concentrated in vacuo and the residue was redissolved in enough methanol to form a solution of 0.2M. Methanesulfonic acid (1 equiv) was added dropwise and stirred for 5 min. After concentrating the solution in vacuo, the residue was repeatedly dissolved in methanol and the solvent was removed (3 times). The residue was then dried under vacuum (18 h), leaving a yellow oil.

Without further purification, the phenylglycine-N-benzylamide methanesulfonate was dissolved in tetrahydrofuran (0.2M) and then was cooled in an ice bath. Triethylamine (2 equiv) was added dropwise, followed by acetyl chloride (1 equiv). The ice bath was removed and stirring was continued at room temperature (18 h). The solution was concentrated in vacuo and the residue was recrystallized from 1:1 95% ethanol/water. Examples 8 and 9 were prepared according to this procedure.

EXAMPLE 8

N-Acetyl-D-phenylglycine-N-benzylamide.

The reaction was run on an 11.9 mmol scale.

Yield: 2.97 g (88%).

mp 219°–221° C.

$[\alpha]_D$=–103.0 (c 1%, EtOH).

$^1$H NMR (DMSO-$d_6$): δ 1.91 (s, 3H), 4.27 (d,J=5.5 Hz, 2H), 5.50 (d,J=7.8 Hz, 1H), 7.14–7.44 (m, 10H), 8.56 (d,J=7.8 Hz, 1H), 8.79 (t,J=5.5 Hz, 1H).

$^{13}$C NMR (DMSO-$_6$): 22.4, 42.0, 56.4, 126.7, 127.0 (2C) 127.2 (2C), 127.4, 127.9 (2C), 128.1 (2C), 138.9, 139.0, 168.9, 170.0 ppm.

IR (KBr): 3260, 1620, 1525, 1450, 1370, 720, 690 cm$^{-1}$.

Mass spectrum, m/e (relative intensity): 203 (2), 149 (94), 106 (100), 91 (32), 86 (43), 77 (14).

Elemental analysis Calculated for $C_{17}H_{18}N_2O_2$ 72.32% C; 6.43% H; 9.92% N. Found 72.04% C; 6.22% H; 9.78% N.

EXAMPLE 9

N-Acetyl-L-phenylglycine-N-benzylamide.

Beginning with 16.1 mmol N-t-Boc-L-phenylglycine-N-benzylamide.

Yield: 2.99 g (66%).

mp 221°–222° C.

$[\alpha]_D$=+105.1 (c 1%, EtOH).

$^1$H NMR (DMSO-$d_6$): δ 1.99 (s, 3H), 4.36 (d,J=5.6 Hz, 2H), 5.60 (d,J=8.0 Hz, 1H), 7.23–7.53 (m, 10H), 8.60 (d,J=8.0 Hz, 1H), 8.83 (t,J=5.6 Hz, 1H).

$^{13}$C NMR (DMSO-$d_6$): 22.4, 42.1, 56.5, 126.8, 127.1 (2C), 127.3 (2C), 127.5, 128.2 (4C), 139.0, 139.1, 169.1, 170.1 ppm.

IR (KBr): 3295, 1630, 1530, 1450, 1395, 720, 695 cm$^{-1}$.

Mass spectrum, m/e (relative intensity): 223 (1), 203 (2), 149 (98), 106 (100), 91 (32), 86 (43), 77 (11).

Elemental analysis Calculated for $C_{17}H_{18}N_2O_2$ 72.32% C; 6.43% H; 9.92% N. Found 72.53% C; 6.49% H; 9.67% N.

EXAMPLE 10

Preparation of N-Acetyl-D,L-alanine-N-(3-methoxy)benzylamide.

The D,L-amino acid amide (11 mmol) was dissolved in dichloromethane (15 mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 0.47 g (17%).

mp 112°–115° C.

$^1$H NMR (DMSO-$d_6$): δ 1.23 (d,J=7.1 Hz, 3H), 1.85 (s, 3H), 3.73 (s, 3H), 3.99–4.48 (m, 1H), 4.25 (d,J=6.1 Hz, 2H), 6.58–7.35 (m, 4H), 8.05 (d,J=7.4 Hz, 1H), 8.35 (t,J=6.0 Hz, 1H).

$^{13}$C NMR (DMSO-d$_6$): 18.1, 22.5, 41.8, 48.3, 54.9, 112.2, 112.3, 119.0, 129.2, 141.0, 159.3, 169.0, 172.4 ppm.

IR (KBr): 3270, 3065, 1625, 1580, 1450, 1260, 1150, 1095, 900, 775, 700, 690 cm$^{-1}$.

Elemental analysis Calculated for C$_{13}$H$_{18}$N$_2$O$_3$ 62.37% C; 7.26% H; 11.19% N. Found 62.29% C; 7.13% H; 11.08% N.

EXAMPLE 11

Preparation of N-Trimethylacetyl-D,L-alanine-N-benzylamide.

D,L-Alanine-N-benzylamide (3.56 g, 20 mmol) was dissolved in dichloromethane (25 mL) and trimethylacetic anhydride (4.10 g, 4.46 mL, 22 mmol) was added dropwise. The solution was stirred at room temperature (18 h) and then concentrated to dryness. The solid residue was recrystallized from benzene/petroleum ether (30°–60° C.).

Yield: 2.07 g (40%).

mp 123°–124° C.

$^1$H NMR (DMSO-d$_6$): δ 1.12 (s, 9H), 1.27 (d,J=7.1 Hz, 3H), 4.23–4.42 (m, 1H), 4.31 (d,J=5.4 Hz, 2H), 7.23–7.30 (m, 5H), 7.38 (d,J=7.4 Hz, 1H), 8.26 (t,J=5.4 Hz, 1H).

$^{13}$C NMR (DMSO-d$_6$): 18.1, 27.2 (3C), 37.9, 42.0, 48.4, 126.6, 127.0 (2C), 128.2 (2C), 139.4, 172.5, 177.1 ppm.

IR (KBr): 3300, 1630, 1535 (br), 1455, 745, 695 cm$^{-1}$.

Mass spectrum, m/e (relative intensity): 262 (2), 203 (19), 156 (18), 128 (51), 106 (31), 91 (100), 77 (15), 65 (28).

Elemental analysis Calculated for C$_{15}$H$_{22}$N$_2$O$_2$ 68.66% C; 8.47% H; 10.68% N. Found 68.91% C; 8.14% H; 10.61% N.

EXAMPLE 12

Preparation of N-Acetyl-D,L-methionine-N-benzylamide.

N-Acetyl-D,L-methionine (4.78 g, 25 mmol) was combined with acetonitrile (75 mL) and the mixture was placed into an ice/salt water bath (–5° C.). Triethylamine (2.53 g, 3.48 mL, 25 mmol,) was added dropwise, followed by ethyl chloroformate (2.71 g, 2.39 mL, 25 mmol). All additions were done slowly so that the temperature of the mixture did not rise above 0° C. The mixture was then stirred at –5° C. (20 min). Benzylamine (3.00 g, 3.06 mL, 28 mmol) in acetonitrile (5 mL) was added dropwise and the mixture was stirred at –5° C. (1 h) and then room temperature (18 h).

The mixture was filtered and a white precipitate was collected and dried in vacuo and identified as the desired product ($^1$H NMR and $^{13}$C NMR analyses). The filtrate was concentrated in vacuo and the residue was combined with hot tetrahydrofuran (50 mL) and cooled in the freezer (3 h), resulting in the formation of a white precipitate. The mixture was filtered and the precipitate was collected, dried in vacuo, and identified as triethylammonium hydrochloride.

The latter filtrate containing tetrahydrofuran was concentrated in vacuo and the resulting residue was purified by flash column chromatography (ethyl acetate). A white solid (R$_f$=0.50, ethyl acetate) was isolated and was identified as the desired product ($^1$H NMR and $^{13}$C NMR analyses). The two solids identified as N-acetyl-D,L-methionine-N-benzylamide were combined and recrystallized from benzene/petroleum ether (30°–60° C.).

Yield: 2.98 g (43%).

mp 134°–135° C.

$^1$H NMR (DMSO-d$_6$): δ 1.69–1.94 (m, 2H), 1.87 (s, 3H), 2.02 (s, 3H), 2.29–2.59 (m, 2H), 4.10–4.53 (m, 1H), 4.29 (d,J=6.0 Hz, 2H), 7.26 (s, 5H), 8.12 (d,J=8.5 Hz, 1H), 8.47 (t,J=6.0 Hz, 1H).

$^{13}$C NMR (DMSO-d$_6$): 14.6, 22.5, 29.7, 31.8, 42.0, 52.0, 126.6, 127.0 (2C), 128.2 (2C), 139.4, 169.5, 171.4 ppm.

IR (KBr): 3280, 1630, 1545, 1460, 750, 700 cm$^{-1}$.

Mass spectrum, m/e (relative intensity): 280 (3), 206 (100), 164 (29), 146 (20), 106 (54), 91 (76), 77 (14), 65 (24).

Elemental analysis Calculated for C$_{14}$H$_{20}$N$_2$O$_2$S 59.96% C; 7.20% H; 9.99% N. Found 60.02% C; 7.14% H; 9.91% N.

EXAMPLE 13

Preparation of N-Acetylalanine-N'-(3-fluoro)benzylamide.

N-Acetylalanine (3.28 g, 25 mmol) was combined with acetonitrile (100 mL) and the mixture was placed into an ice/salt bath at –5° C. Triethylamine (2.53 g, 3.5 mL, 25 mmol) was added dropwise followed by the addition of ethyl chloroformate (2.71 g, 2.40 mL, 25 mmol). All additions were done slowly so that the temperature of the mixture did not rise above 0° C. The mixture was then stirred at –5° C. for 20 minutes. 3-Fluorobenzylamine (3.58 g, 28 mmol) and acetonitrile (5 mL) was added dropwise and was stirred at –5° C. for one hour and then at room temperature for 18 hours. The reaction became homogenous during this time interval.

The solution was concentrated in vacuo and the residue was combined with hot tetrahydrofuran (100 mL) and cooled in the freezer for 3 hours resulting in the formation of a white precipitate. The mixture was filtered and the precipitate was collected, dried in vacuo and identified as triethylammonium hydrochloride (3.51 g, mp 253°–257° C.). The filtrate was concentrated in vacuo and the resulting yellow solid was recrystallized from chloroform/diethyl ether.

Yield: 3.22 g (54%).

mp 120°–121° C.

$^1$H NMR (DMSO-d$_6$): δ 1.27 (d,J=7.1 Hz, 3H), 1.90 (s, 3H), 4.23–4.41 (m, 1H), 4.33 (d,J=6.1 Hz, 2H), 7.05–7.37 (m, 4H), 8.19 (d,J=7.1 Hz, 1H), 8.53 (t,J=6.1 Hz, 1H).

$^{13}$C NMR (DMSO-d$_6$): 17.9, 22.4, 41.5, 48.5, 113.3 (d,J=20.4 Hz), 113.5 (d,J=21.7 Hz), 122.8, 130.1 (d,J=7.9 Hz), 142.4 (d,J=7.4 Hz), 162.3 (d,J=243.6 Hz), 169.6, 172.8 ppm.

IR (KBr): 3280, 1645, 1545, 1450, 745, 680 cm$^{-1}$.

Mass spectrum, m/e (relative intensity): 238 (18), 151 (22), 124 (49), 114 (47), 109 (100), 87 (76), 72 (27).

Elemental analysis Calculated 60.48% C; 6.36% H; 11.76% N. Found 60.55% C; 6.32% H; 11.71% N.

EXAMPLE 14

Preparation of D,L-α-Acetamido-N-benzyl-3-thiopheneacetamide.

D,L-α-Acetamido-3-thiopheneacetic acid (2.99 g, 15 mmol) was combined with acetonitrile (60 mL) and the mixture was placed into an ice/salt water bath (–5° C.). Triethylamine (1.51 g, 2.10 mL, 15 mmol) was added dropwise, followed by ethyl chloroformate (1.63 g, 1.43 mL, 15 mmol). All additions were done slowly so that the temperature of the mixture did not rise above 0° C. The mixture was then stirred at –5° C. (20 min). Benzylamine (1.77 g, 1.80 mL, 16.5 mmol) in acetonitrile (10 mL) was added dropwise and the mixture was stirred at –5° C. (1 h) and then room temperature (18 h). The mixture was concentrated in vacuo and the residue was combined with hot tetrahydrofuran (50 mL) and cooled in the freezer (3 h), resulting in the formation of a white precipitate. The mixture was filtered and the precipitate was collected, dried in vacuo, and identified as triethylammonium hydrochloride ($^1$H NMR analysis). The filtrate was concentrated in vacuo and the resulting yellow solid was recrystallized from 1:1 95% ethanol/water.

Yield: 1.91 g (44%).

mp 198°–199° C.

$^1$H NMR (DMSO-$d_6$): δ 1.91 (s, 3H), 4.29 (d,J=5.2 Hz, 2H), 5.61 (d,J=7.9 Hz, 1H), 7.15–7.50 (m, 3H), 8.55 (d,J=7.9 Hz, 1H), 8.74 (t,J=5.2 Hz, 1H).

$^{13}$C NMR (DMSO-$d_6$): 22.3, 42.0, 52.5, 122.4, 126.1, 126.7, 127.0 (3C), 128.2 (2C), 139.0, 139.2, 169.0, 169.8 ppm.

IR (KBr): 3460, 1675, 1570, 1400, 720, 695 cm$^{-1}$.

Mass spectrum, m/e (relative intensity): 288 (2), 245 (3), 155 (88), 112 (100), 91 (31), 85 (17), 65 (7).

Elemental analysis Calculated for $C_{15}H_{16}N_2O_2S$ 62.48% C; 5.59% H; 9.71% N. Found 62.41% C; 5.47% H; 9.55% N.

EXAMPLE 15

Preparation of D,L-α-Acetamido-N-benzyl-2-thiopheneacetamide.

N-Acetyl-D,L-ethoxyglycine-N-benzylamide (6.26 g, 25 mmol) was combined with dry ether (175 mL) and then boron trifluoride etherate (5.68 g, 5.0 mL, 40 mmol) was added dropwise, resulting in a homogeneous solution. After stirring a short time, a small amount of a yellow oil separated from the solution. Thiophene (8.41 g, 8.0 mL, 100 mmol) was then added dropwise via syringe and the reaction was stirred at room temperature (4 d). The mixture was cooled in an ice bath and cold aqueous saturated NaHCO$_3$ (200 mL) was added and the aqueous layer was extracted with ethyl acetate (2×100 mL). The organic washings and the original ether layer were combined, dried (Na$_2$SO$_4$), and concentrated in vacuo. The residue was purified by flash column chromatography, using 94:6 chloroform/methanol as an eluant ($R_f$=0.7 94:6 chloroform/methanol), and then recrystallized from benzene.

Yield: 2.67 g (37%).

mp 167°–16° C.

$^1$H NMR (DSMO-$d_6$): δ 1.91 (s 3H) 4.31 (d,J=6.0 Hz, 2H), 5.74 (d,J=7.9 Hz, 1H), 6.99–7.44 (m, 8H), 8.64 (d,J=7.9 Hz, 1H), 8.85 (t,J=6.0 Hz, 1H).

$^{13}$C NMR (DMSO-$d_6$): 22.4, 42.3, 52.2, 125.6, 125.8, 126.6, 126.9, 127.3 (2C), 128.3 (2C), 139.0, 141.4, 169.2, 169.3 ppm.

Mass spectrum, m/e (relative intensity): 289 (2), 181 (6), 155 (100), 112 (100), 91 (100), 85 (34), 74 (24).

Elemental analysis Calculated for $C_{15}H_{16}N_2O_2S$ 62.48% C; 5.59% H; 9.71% N. Found 62.64% C; 5.73% H; 9.61% N.

EXAMPLE 16

Preparation of D,L-α-Acetamido-N-benzyl-2-furanacetamide.

N-Acetyl-D,L-2-(2-furyl)glycine (0.47 g, 2.56 mmol) was combined with acetonitrile (10 mL) and cooled to −5° C. (ice/salt water bath). Triethylamine (0.26 g, 0.36 mL, 2.56 mmol) was then rapidly added and the mixture stirred at −5° C. (3 min). Ethyl chloroformate (0.28 g, 0.25 mL, 2.56 mmol) was added dropwise between −4° C. and −3° C., and the resulting suspension was stirred at −4° C. (20 min), and then an acetonitrile solution (2 mL) of benzylamine (0.30 g, 0.31 mL, 2.82 mmol) was carefully added. During the addition of benzylamine the temperature of the solution did not go above 0° C. The mixture was stirred at −5° C. (1 h) and at room temperature (18 h), and then concentrated in vacuo. The residue was then triturated with hot tetrahydrofuran (5 mL), cooled at −16° C. (3 h), and the resulting white precipitate was filtered and identified as triethylamine hydrochloride ($^1$H NMR, 60 MHz, δ 1.00 (t,J=7.5 Hz, CH$_3$), 2.82 (q,J=7.5 Hz, CH$_2$), 3.83 (s, NH)). The filtrate was evaporated to dryness in vacuo and the resulting oil purified by flash chromatography (98:2 chloroform/methanol) to give 0.09 g (13%) of the desired product as a white solid: $R_f$ 0.30 (98:2 chloroform/methanol).

mp 178°–179° C.

$^1$H NMR (300 MHz, DMSO-$d_6$): δ 1.90 (s, CH$_3$), 4.31 (d,J=6.0 Hz, CH$_2$), 5.58 (d,J=8.1 Hz, CH), 6.27–6.33 (m, C$_3$'H), 6.40–6.44 (m, C$_4$'H), 7.20–7.36 (m, Ph), 7.60–7.64 (m, C$_5$'H), 8.57 (d,J=8.1 Hz, NH), 8.73 (t,J=6.0 Hz, NH).

$^{13}$C NMR (300 MHz, DMSO-$d_6$): 22.35 (CH$_3$), 42.27 (CH$_2$), 50.95 (CH), 107.60 (C$_3$'), 110.55 (C$_4$'), 126.82 (2C$_2$" or 2C$_3$"), 127.08 (2C$_2$" or 2C$_3$"), 128.27 (C$_4$"), 139.05 (C$_1$"), 142.58 (C$_5$'), 151.16 (C$_2$'), 168.02 (CH$_3$CO), 169.30 (NHCO) ppm.

IR (KBr): 3230, 1625 (br), 1525 (br), 1375 (br), 1230, 1090, 890 cm$^{-1}$.

Mass spectrum, m/e (relative intensity): 273 (1), 139 (100), 96 (94), 91 (51), 65 (9).

Elemental analysis Calculated for $C_{15}H_{16}N_2O_3$ 66.16% C; 5.83% H; 10.29% N. Found 65.92% C; 5.83% H; 10.15% N.

EXAMPLE 17

Preparation of D,L-α-Acetamido-N-benzyl-2-pyrroleacetamide.

2-Acetamido-N-benzyl-2-ethoxyacetamide (2.00 g, 8.0 mmol) was suspended in anhydrous ethyl ether (60 mL), and then boron trifluoride etherate (1.82 g, 1.57 mL, 12.8 mmol) was added in one portion and the resulting solution was stirred (15 min). The pyrrole (2.14 g, 2.22 mL, 32 mmol) was then added in one portion and the solution was stirred at room temperature (48 h) during which time a precipitate formed. Hexanes (80 mL) were then added to the suspension, and the mixture was filtered and the brown semi-solid was triturated with 95:5 chloroform/methanol (30 mL) to furnish a green solid. This material was purified by flash chromatography (95:5 chloroform/methanol) to yield 0.94 g (35%) of the desired product as a white solid: $R_f$ 0.29 (96:4 chloroform/methanol).

mp 174°–175° C.

$^1$H NMR (300 MHz, CD$_3$CN): δ 1.93 (s, CH$_3$), 4.35 (d,J=6.0 Hz, CH$_2$), 5.42 (d,J=6.9 Hz, CH), 6.00–6.18 (m, C$_3$'H, C$_4$'H), 6.68–6.72 (m, C$_5$'H), 7.04 (d,J=6.9 Hz, NH), 7.1.7 (t,J=6.0 Hz, NH), 7.10–7.47 (m, Ph), 9.10–9.80 (br s, NH).

$^{13}$C NMR (300 MHz, CD$_3$CN): 23.02 (CH$_3$), 43.83 (CH$_2$), 52.65 (CH), 107.57 (C$_3$'), 108.85 (C$_4$'), 119.33 (C$_5$'), 127.96 (C$_2$'), 128.01 (2C$_2$" or 2C$_3$"), 128.09 (2C$_2$" or 2C$_3$"), 129.49 (C$_4$"), 140.01 (C$_1$"), 170.94 (COCH$_3$), 171.21 (CONH) ppm.

IR (KBr): 3320, 1570 (br), 1470 (br), 1330, 1230, 950, 890, 860, 760, 710, 690, 655 cm$^{-1}$.

Mass spectrum, m/e (relative intensity): 171 (12), 228 (2), 213 (1), 180 (2), 164 (9), 137 (93), 108 (20), 95 (100), 91 (38), 82 (35), 68 (15).

High resolution mass spectral analysis Calculated for $C_{15}H_{17}N_3O_2$ 271.13208. Found 271.13144.

EXAMPLE 18

Preparation of D,L-2-Acetamido-N-benzyl-2-ethoxyacetamide.

An ethanolic solution (420 mL) of ethyl 2-acetamido-2-ethoxyacetate (27.92 g, 147 mmol) and benzylamine (23.70 g, 24 mL, 221 mmol) was stirred at 40°–45° C. for 3 days. The reaction mixture was evaporated in vacuo and the residue recrystallized (1:3.5 tetrahydrofuran/hexanes (650 mL)) to yield 25.80 g (70%) of the desired product as beige crystals: $R_f$ 0.59 (95:5 chloroform/methanol).

mp 153°–155° C.

$^1$H NMR (300 MHz, CDCl$_3$): δ 1.20 (t,J=7.0 Hz, CH$_3$), 2.07 (s, CH$_3$), 3.60–3.76 (m, CH$_2$CH$_3$), 4.40–4.54 (m, CH$_2$NH), 5.60 (d,J=8.7 Hz, CH), 6.63 (d,J=8.7 Hz, NH), 7.00 (br s, NH), 7.26–7.36 (m, Ph).

$^{13}$C NMR (300 MHz, CDCl$_3$): 15.06 (CH$_3$CH$_2$), 23.25 (CH$_3$CO), 43.60 (CH$_2$NH), 64.51 (CH$_2$CH$_3$), 77.43 (CH), 127.69 (2C$_2$" or 2C$_3$", C$_4$"), 128.79 (2C$_2$" or 2C$_3$"), 137.57 (C$_1$"), 168.13 (COCH$_3$), 171.29 (CONH) ppm.

IR (KBr): 3260, 1630 (br), 1550 (sh), 1505 (br), 1380, 1360, 1230, 1115, 1060, 1015, 890, 745, 690 cm$^{-1}$.

Mass spectrum, m/e (relative intensity): 251 (4), 163 (9), 116 (98), 106 (34), 91 (98), 74 (100).

Elemental analysis Calculated for $C_{13}H_{18}N_2O_3$ 62.38% C; 7.25% H; 11.19% N. Found 62.49% C; 7.27% H; 11.24% N.

EXAMPLE 19

Preparation of D,L-2-Acetamido-N-benzyl-2-methoxyacetamide.

To a methanolic solution (180 mL) of methyl 2-acetamido-2-methoxyacetate (8.73 g, 54 mmol) was rapidly added benzylamine (8.68 g, 8.80 mL, 81 mmol) and then the mixture was stirred at 50° C. (3 days) during which time a beige precipitate appeared. The solvent was removed in vacuo and the resulting precipitate was recrystallized from tetrahydrofuran (2×) to give 7.67 g (32%) of the desired product as beige crystals: $R_f$ 0.35 (95:5 chloroform/methanol).

mp 145°–146° C.

$^1$H NMR (300 MHz, CDCl$_3$): δ 2.06 (s, CH$_3$CO), 3.37 (s, CH$_3$O), 4.40–4.35 (m, CH$_2$), 5.52 (d,J=8.7 Hz, CH), 7.12 (d,J=8.7 Hz, NH), 7.20–7.40 (m, Ph, NH).

$^{13}$C NMR (300 MHz, CDCl$_3$): 23.03 (CH$_3$CO), 43.51 (CH$_2$), 55.84 (CH$_3$O), 78.94 (CH), 127.62 (C$_4$"), 127.70 (2C$_2$" or 2C$_3$"), 128.70 (2C$_2$" or 2C$_3$"), 137.45 (C$_1$"), 166.91 (COCH$_3$), 171.57 (CONH) ppm.

IR (KBr): 1260, 1825 (br), 1550, 1505, 1435, 1390, 1370, 1230, 1120, 1050, 935, 890, 690 cm$^{-1}$.

Mass spectrum, m/e (relative intensity): 237 (1), 205 (2), 177 (2), 163 (4), 146 (1), 134 (1) 121 (2), 106 (26), 102 (98), 91 (95), 77 (13), 61 (100).

Elemental analysis Calculated for $C_{12}H_{16}N_2O_3$ 61.00% C; 6.83% H; 11.86% N. 60.91% C; 6.85% H; 11.66% N.

EXAMPLE 20

Preparation of (D,L)-α-Acetamido-N-benzyl-2-(5-methylfuran)acetamide.

N-Acetyl-D,L-ethoxyglycine-N-benzylamide (2.00 g, 8.0 mmol) was suspended in anhydrous ethyl ether, and then boron trifluoride etherate (1.82 g, 12.8 mmol) was rapidly added, and the resulting solution was stirred for 15 min. The 2-methylfuran (2.63 g, 32.0 mmol) was then added and the reaction was stirred at room temperature (3 d). The reaction mixture was poured into an aqueous saturated NaHCO$_3$ solution and extracted with ethyl acetate (3×). The ethyl acetate extracts were combined, dried (Na$_2$SO$_4$) and evaporated in vacuo to give a beige solid, which was purified by flash chromatography (98:2 chloroform/methanol) to give the desired product as a white crystalline solid.

Yield: 1.40 g (61%)

$R_f$ 0.25 (98:2 chloroform/methanol).

mp 148°–150° C.

$^1$H NMR (DMSO-d$_6$) δ 1.88 (s, CH$_3$CO), 2.23 (s, CH$_3$), 4.24–4.36 (m, CH$_2$), 5.49 (d, J=8.0 Hz, CH), 6.01 (br s, C$_3$'H), 6.14 (d, J=2.4 Hz, C$_4$'H), 7.20–7.31 (m, Ph), 8.52 (d, J=8.0 Hz, NH), 8.69 (t, J=5.6 Hz, NH).

$^{13}$C NMR (DMSO-d$_6$) 13.44 (CH$_3$), 22.35 (CH$_3$CO), 44.11 (CH$_2$), 53.23 (CH), 107.51 (C$_3$' or C$_4$'), 110.40 (C$_3$' or C$_4$'), 128.13 (C$_4$"), 128.18 (2C$_2$" or 2C$_3$"), 129.43 (2C$_2$" or 2C$_3$"), 139.69 (C$_1$"), 149.18 (C$_2$' or C$_5$'), 153.81 (C$_2$' or C$_5$'), 170.78 (CH$_3$CO), 173.03 (CONH) ppm.

IR (KBr) 3270, 1620 (br), 1520 (br), 1440, 1360, 1210, 1010 cm$^{-1}$.

Mass spectrum, m/e (relative intensity) 286 (3), 179(8), 153 (57), 152 (57), 111 (23), 110 (100), 97 (23), 91 (31).

Elemental Analysis Calculated: 67.12% C; 6.34% H; 9.78% N. Found: 66.92% C; 6.52% H; 9.52% N.

EXAMPLE 21

Preparation of (D,L)-α-Acetamido-N-benzyl-2-benzofuranacetamide.

N-Acetyl-D,L-ethoxyglycine-N-benzylamide (1.00 g, 4 mmol) was suspended in anhydrous ethyl ether (30 mL) and then boron trifluoride etherate (0.91 g, 63 mmol) was rapidly added, and the resulting solution was stirred for 15 min. The benzofuran (1.89 g, 16 mmol) was then added and the reaction was stirred at room temperature (3 d). The reaction mixture was poured into an ice-cold saturated aqueous solution of NaHCO$_3$, and then the mixture was maintained at this temperature for an additional 15 min. The mixture was extracted with ethyl acetate (2×), and the organic layers were combined, dried (Na$_2$SO$_4$) and evaporated in vacuo. The residue was purified by flash chromatography (100% chloroform, then 99:1 chloroform/methanol) to yield the desired product.

Yield: 0.43 g (33%).

$R_f$ 0.30 (98:2 chloroform/methanol).

mp 195°–196° C.;

$^1$H NMR (DMSO-d$_6$) δ 1.94 (s, CH$_3$CO), 4.34 (d, J=5.7 Hz, CH$_2$), 5.77 (d, J=8.1 Hz, CH), 7.24–7.32 (m, C$_3$H, C$_5$H, C$_6$H, Ph), 7.54 (d, J=7.0 Hz, C$_4$H or C$_7$H), 7.62 (d, J=7.0 Hz, C$_4$H or C$_7$H), 8.74 (d, J=8.1 Hz, NH), 8.86 (t, J=5.7 Hz, NH).

$^{13}$C NMR (DMSO-d$_6$) 22.27 (CH$_3$CO), 42.30 (CH$_2$), 51.22 (CH), 104.34 (C$_3$'), 110.90 (C$_7$'), 121.05 (C$_4$'), 122.90 (C$_5$'), 124.28 (C$_6$'), 126.73 (C$_{3'a}$), 127.01 (2C$_2$" or 2C$_3$"), 127.69 (2C$_2$" or 2C$_3$"), 128.14 (C$_4$"), 138.87 (C$_1$"), 154.10 (C$_{7'a}$), 154.30 (C$_2$'), 167.40 (CH$_3$CO), 169.26 (CONH) ppm.

IR (KBr) 3230, 1625 (br), 1520 (br), 1440, 1090, 1085, 890, 785, 690 cm$^{-1}$;

Mass spectrum, m/e (relative intensity) 322 (5), 279 (1), 264 (1), 234 (1), 215 (5), 189 (45), 146 (100), 130 (11), 118 (7), 91 (87), 65 (16).

High resolution mass spectrum, Calcd for $C_{19}H_{18}N_2O_3$ 322.1317. Found 322.1318.

EXAMPLE 22

Preparation of (D,L)-α-Acetamido-N-benzyl-2-benzo[b]thiopheneacetamide.

N-Acetyl-D,L-ethoxyglycine-N-benzylamide (1.00 g, 4 mmol) was suspended in anhydrous ethyl ether (15 mL) and then boron trifluoride etherate (0.91 g, 6.3 mmol) was rapidly added, and the resulting solution was stirred for 15 min. The benzo[b]thiophene (2.14 g, 16 mmol) was then added and the reaction was stirred at room temperature (3 d). The solution was poured into an ice-cold saturated aqueous solution of $NaHCO_3$, and then stirred for 15 min at 0° C. The mixture was extracted with ethyl acetate (2×), and the organic layers were combined, dried ($Na_2SO_4$) and evaporated in vacuo to give an orange oil. The oil was triturated with ethyl ether to yield a crystalline product which was filtered and further purified by flash chromatography (99:1 chloroform/methanol) to give the desired product.

Yield: 0.06 g (4%).

$R_f$ 0.32 (99:1 chloroform/methanol).

mp 226°–227° C.

$^1$H NMR (DMSO-$d_6$) δ 1.94 (s, $CH_3CO$), 4.34 (d, J=5.7 Hz, $CH_2$), 5.86 (d, J=8.1 Hz, CH), 7.20–7.38 (m, $C_3H$, $C_6H$, $C_7H$, Ph), 7.77–7.80 (m, $C_4H$ or $C_5H$), 7.89–7.93 (m, $C_4H$ or $C_5H$), 8.76 (d, J=8.1 Hz, NH), 8.97 (t, J=5.7 Hz, NH).

$^{13}$C NMR (DMSO-$d_6$) 22.34 ($CH_3CO$), 42.38 ($CH_2$), 52.70 (CH), 122.15 ($C_{4'}$ or $C_{7'}$), 122.32 ($C_{4'}$ or $C_{7'}$), 123.45 ($C_{3'}$), 124.37 ($C_{5'}$ or $C_{6'}$), 124.41 ($C_{5'}$ or $C_{6'}$), 126.89 ($C_{4''}$), 127.27 ($2C_{2''}$ or $2C_{3''}$), 128.27 ($2C_{2''}$ or $2C_{3''}$), 138.84 ($C_{3'a}$ or $C_{7'a}$), 138.95 ($C_{3'a}$ or $C_{7'a}$), 142.58 ($C_{1'}$), 168.65 ($CH_3CO$), 169.12 (CONH) ppm. [A distinct signal for the $C_{2'}$ carbon was not detected and is presumed to coincide with the $C_{1'}$ carbon at 142.58 ppm.].

IR (KBr) 3240, 1610 (br), 1510 (br), 1420, 1360, 1215, 1085, 885, 730, 710, 685 cm$^{-1}$.

Mass spectrum, m/e (relative intensity) 338 (8), 295 (2), 205 (76), 162 (100), 135 (22), 108 (12), 91 (59).

Elemental Analysis: Calculated: 67.43% C; 5.36% H; 8.28% N. Found: 67.21% C; 5.37% H; 8.12% N.

EXAMPLE 23

Preparation of (D,L)-α-Acetamido-N-benzyl-3-indoleacetamide.

N-Acetyl-D,L-ethoxyglycine-N-benzylamide (0.69 g, 2.78 mmol) was suspended in anhydrous ethyl ether (20 mL) and then boron trifluoride etherate (0.63 g, 4.40 mmol) was rapidly added, and the resulting solution was stirred for 15 min. The indole (1.30 g, 11.00 mmol) was then added and the reaction was stirred at room temperature (22 h). Petroleum ether (35°–60° C.) was added to the reaction, and the resulting semisolid material filtered, and washed with petroleum ether (35°–60° C.). Purification of the reaction mixture was accomplished by flash chromatography (98:2 chloroform/methanol) to produce the title compound as a white solid.

Yield: 0.25 g (18%).

$R_f$ 0.14 (95:5 chloroform/methanol)

mp 213°–214° C.

$^1$H NMR (DMSO-$d_6$) δ 1.90 (s, $CH_3CO$), 4.36 (d, J=6.0 Hz, $CH_2$), 5.72 (d, J=7.2 Hz, CH), 6.90–7.37 (m, Ph, $C_2H$), 7.02 (dd, J=7.5 Hz, J=7.5 Hz, $C_5H$ or $C_6H$), 7.12 (dd, J=7.5 Hz, J=7.5 Hz, $C_5H$ or $C_6H$), 7.39 (d, J=7.5 Hz, $C_4H$ or $C_7H$), 7.65 (d, J=7.5 Hz, $C_4H$ or $C_7H$), 7.86 (d, J=7.2 Hz, NHCH), 8.13 (t, J=6.0 Hz, $NHCH_2$), 10.30–10.80 (br s, NH).

$^{13}$C NMR (DMSO-$d_6$) 22.32 ($CH_3CO$), 42.23 ($CH_2$), 49.98 (CH), 111.51 ($C_{7'}$), 112.08 ($C_{3'}$), 118.76 ($C_{4'}$ or $C_{6'}$), 119.24 ($C_{4'}$ or $C_{6'}$), 121.37 ($C_{5'}$), 123.94 ($C_{2'}$), 126.58 ($C_{3'a}$), 126.71 ($C_{4''}$), 127.33 ($2C_{2''}$ or $2C_{3''}$), 128.18 ($2C_{2''}$ or $2C_{3''}$), 136.28 ($C_{7'a}$), 139.44 ($C_{1''}$), 169.13 ($CH_3CO$), 170.81 (CONH) ppm.

IR (KBr) 3260, 1610 (br), 1515 (br), 1450, 1420, 1370, 1350, 1235, 1095, 895, 735, 715, 695, 600 cm$^{-1}$.

Mass spectrum, m/e (relative intensity 321 (5), 278 (1), 264 (1), 233 (1), 214 (6), 187 (85), 171 (3), 145 (100), 118 (18), 91 (39).

Elemental Analysis: Calculated: 71.01% C; 5.96% H; 13.06% N. Found: 70.87% C; 6.15% H; 12.78% N.

EXAMPLE 24

Preparation of (D,L)-α-Acetamido-N-benzyl-2-(5-methylpyrrole)acetamide.

N-Acetyl-D,L-ethoxyglycine-N-benzylamide (2.00 g, 8 mmol) was suspended in anhydrous ethyl ether (175 mL), and then boron trifluoride etherate (1.38 g, 9.7 mmol) was added and the resulting solution stirred (15 min). The 2-methylpyrrole (0.85 g, 10 mmol) was then added and the reaction mixture was stirred under $N_2$ (6 d), during which time the color of the reaction mixture turned reddish brown and a dark-brown deposit formed at the bottom of the flask. The clear solution was decanted and treated with an aqueous saturated $NaHCO_3$ solution containing ice (100 mL) for 30 min. The aqueous reaction mixture was extracted with ethyl acetate (3×30 mL). The combined extracts were dried ($Na_2SO_4$) and the solvent removed in vacuo. The brown oily residue was purified by flash column chromatography using 98:2 chloroform/methanol as the eluent to yield the desired compound. The product was recrystallized from ethyl acetate/hexane to give a light yellow amorphous solid.

Yield 0.20 g (94%)

$R_f$ 0.44 (95:5, chloroform/methanol).

mp 167°–168° C.

$^1$H NMR (DMSO-$d_6$) δ 1.87 (s, $CH_3$), 2.13 (s, $COCH_3$), 4.27 (br s, $CH_2$), 5.33 (d, J=7.4 Hz, CH), 5.60 (s, $C_4H$), 5.77 (s, $C_3H$), 7.19–7.30 (m, 5 PhH), 8.22 (d, J=7.4 Hz, NH), 8.45 (t, J=5.5 Hz, NH), 10.38 (s, NH).

$^{13}$C NMR (DMSO-$d_6$) 12.74 ($CH_3$), 22.49 ($COCH_3$), 42.11 ($CH_2$), 51.21 (CH), 105.09 ($C_4$), 106.07 ($C_3$), 126.16 ($C_5$), 126.64 ($C_{4'}$), 126.85 ($C_2$), 127.09 ($2C_{2'}$ or $2C_{3'}$), 128.17 ($2C_{2'}$ or $2C_{3'}$), 139.33 ($C_{1'}$), 168.88 ($COCH_3$), 169.79 (CONH) ppm.

IR (KBr) 3250, 1630, 1520, 1420, 1360, 1300, 1260, 1230, 1160, 1110, 1020 cm$^{-1}$.

Mass spectrum, m/e (relative intensity) 285 (M$^+$, 10), 178 (20), 152 (24), 151 (100), 110 (12), 109 (93), 108 (22), 107 (25), 94 (16), 91 (43).

Elemental Analysis: Calculated: 67.35% C; 6.71% H; 14.73% N. Found: 67.57% C; 6.90% H; 14.52% N.

Synthesis of Unsubstituted and Substituted-α-Acetamido-N-benzyl-2-furanacetamides.

General Procedure.

4-Methylmorpholine (1 equiv) was added to a solution of α-acetamido-2-furanacetic acid (1 equiv) in dry tetrahydrofuran (75 mL/10 mmol) at −10° to −15° C. under $N_2$. After stirring (2 min), isobutyl chloroformate (1 equiv) was added leading to the precipitation of a white solid. The reaction was allowed to proceed for 2 additional minutes and then a solution of the substituted benzylamine (1 equiv) in tetrahydrofuran (10 mL/10 mmol) was added over 5 min at −10° to −15° C. The reaction mixture was allowed to stir at room temperature for 5 min and then the 4-methylmorpholine hydrochloride salt filtered. The organic layer was concentrated in vacuo, and the residue was triturated with ethyl acetate, and the remaining white solid filtered. Concentration of the ethyl acetate layer led to additional amounts of the white solid. The desired product was purified by either recrystallization, or flash chromatography of the combined solid material. Examples 25–32 were prepared according to this procedure.

EXAMPLE 25

(D,L-α-Acetamido-N-benzyl-2-furanacetamide.

Using benzyl amine (0.27 g, 2.56 mmol) and racemic α-acetamido-2-furanacetic acid (0.47 g, 2.56 mmol) gave the desired compound. The product was recrystallized from ethyl acetate to give a white solid.

Yield: 0.46 g (65%)

$R_f$ 0.30 (98:2 chloroform/methanol).

mp 177°–178° C.

$^1$H NMR (DMSO-$d_6$) δ 1.90 (s, CH$_3$), 4.31 (d, J=6.0 Hz, CH$_2$), 5.58 (d, J=8.1 Hz, CH), 6.27–6.33 (m, C$_3$H), 6.40–6.44 (m, C$_4$H), 7.20–7.36 (m, 5 PhH), 7.60–7.64 (m, C$_5$H), 8.57 (d, J=8.1 Hz, NH), 8.73 (t, J=6.0 Hz, NH).

EXAMPLE 26

(D,L)-α-Acetamido-N-(2-fluorobenzyl)-2-furanacetamide.

Using 2-fluorobenzylamine (1.13 g, 9.0 mmol) and racemic α-acetamido-2-furanacetic acid (1.50 g, 8.2 mmol) gave the desired product.

Yield: 120 g (50%).

$R_f$ 0.36 (94:4 chloroform/methanol).

mp 193°–195° C. (recrystallized from EtOAc).

$^1$H NMR (DMSO-$d_6$) δ 1.89 (s, COCH$_3$), 4.33 (d, J=5.5 Hz, CH$_2$), 5.58 (d, J=80 Hz, CH), 6.28 (s, C$_4$H), 6.29 (s, C$_3$H), 7.62 (s, C$_5$H), 7.13–7.35 (m, 4 ArH), 8.61 (d, J=80 Hz, NH), 8.76 (t, J=5.5 Hz, NH).

$^{13}$C NMR (DMSO-$d_6$) 22.35 (COCH$_3$), 36.12 (d, $J_{CF}$=6.6 Hz, CH$_2$), 50.88 (CH), 107.64 (C$_4$), 110.43 (C$_3$), 115.04 (d, $J_{CF}$=21.4 Hz, C$_{3'}$), 124.29 (d, $J_{CF}$=4.2 Hz, C$_5$), 125.64 (d, $J_{CF}$=15.0 Hz, C$_{1'}$), 128.94 (d, $J_{CF}$=9.0 Hz, C$_{4'}$ or C$_{6'}$), 129.27 (d, $J_{CF}$=5.5 Hz, C$_{4'}$ or C$_{3'}$), 142.66 (C$_5$), 151.07 (C$_2$), 159.99 (d, $J_{CF}$=244.4 Hz, C$_{2'}$), 168.17 (COCH$_3$), 169.24 (CONH) ppm.

IR (KBr) 3270, 1630, 1520, 1440, 1360, 1220, 1180, 1140, 1100, 1000, 740 cm$^{-1}$.

Mass spectrum, m/e (relative intensity) 291 (M$^+$+1, 3), 274 (2), 247(3), 165 (4), 145 (10), 139 (98), 138 (46), 126 (7), 110 (10), 109 (65), 97 (93), 96 (100).

Elemental Analysis: Calculated: 62.02% C; 5.21% H; 9.65% N. Found: 62.20% C; 5.19% H; 9.69% N.

EXAMPLE 27

(D,L)-α-Acetamido-N-(3-fluorobenzyl)-2-furanacetamide.

Making use of 3-fluorobenzylamine (1.13 g, 9.0 mmol) and racemic α-acetamido-2-furanacetic acid (1.50 g, 8.2 mmol) gave the desired product.

Yield 1.90 g (80%).

$R_f$ 0.30 (96:4 chloroform/methanol).

mp 163°–165° C. (recrystallized from ethyl acetate).

$^1$H NMR (DMSO-$d_6$) δ 1.89 (s, COCH$_3$), 4.31 (d, J=5.5 Hz, CH$_2$), 5.55 (d, J=7.8 Hz, CH, 6.31 (s, C$_4$H), 6.42 (s, C$_3$H), 6.98–7.37 (m, 4 ArH), 7.62 (s, C$_5$H), 8.61 (d, J=7.8 Hz, NH), 8.70 (t, J=5.5 Hz, NH).

$^{13}$C NMR (DMSO-$d_6$) 22.35 (COCH$_3$), 41.71 (CH$_2$), 51.01 (CH), 107.73 (C$_4$), 110.59 (C$_3$), 113.50 (d, $J_{CF}$=21.6 Hz, C$_{2'}$ or C$_{4'}$), 113.60 (d, $J_{CF}$=22.3 Hz, C$_{2'}$ or C$_{4'}$), 122.95 (br, C$_{6'}$), 130.18 (d, $J_{CF}$=8.6 Hz, C$_{5'}$), 142.21 (d, $J_{CF}$=7.5 Hz, C$_{1'}$), 142.66 (C$_5$), 151.03 (C$_2$), 162.28 (d, $J_{CF}$=243.3 Hz, C$_{3'}$), 168.23 (COCH$_3$), 169.31 (CONH) ppm.

IR (KBr) 3230, 1630, 1540, 1440, 1360, 1220, 1140, 1000, 730 cm$^{-1}$.

Mass spectrum, m/e (relative intensity) 290 (M$^+$,71), 231 (7), 165 (18), 140 (23), 130 (100), 126 (16), 109 (6), 97 (118), 96 (100), 96 (30).

Elemental analysis: Calculated: 62.02% C; 5.21% H, 9.65% N. Found: 61.97% C; 5.35% H; 9.53% N.

EXAMPLE 28

(D,L)-α-Acetamido-N-(4-fluorobenzyl)-2-furanacetamide.

Using racemic α-acetamido-2-furanacetic acid (1.50 g, 8.2 mmol) and 4-fluorobenzylamine (1.13 g, 9.0 mmol) gave the desired product.

Yield 2.10 g (88%).

$R_f$ 0.30 (96:4 chloroform/methanol).

mp 188°–190° C. (recrystallized from ethyl acetate).

$^1$H NMR (DMSO-$d_6$) δ 1.88 (s, COCH$_3$), 4.27 (d, J=5.5 Hz, CH$_2$), 5.55 (d, J=8.0 Hz, CH), 6.27 (s, 1H), 6.41 (s, 1H), 7.09–7.15 (m, 2ArH), 7.12–7.27 (m, 2 ArH), 7.61 (s, 1H), 8.58 (d, J=8.0 Hz, NH), 8.75 (t, J=5.5 Hz, NH).

$^{13}$C NMR (DMSO-$d_6$) 22.28 (COCH$_3$), 41.51 (CH$_2$), 50.87 (CH), 107.52 (C$_4$), 110.46 (C$_3$), 114.90 (d, $J_{CF}$=21.1 Hz, C$_{3'}$), 129.48 (d, $J_{CF}$=8.3 Hz, C$_{2'}$), 135.23 (d, $J_{CF}$=3.2 Hz, C$_{1'}$), 142.53 (C$_5$), 151.08 (C$_2$), 161.12 (d, $J_{CF}$=242.2 Hz, C$_{4'}$), 167.95 (COCH$_3$), 169.13 (CONH) ppm.

IR (KBr) 3230, 1620, 1500, 1360, 1320, 1260, 1210, 1140, 1000, 820, 780, 730 cm$^{-1}$.

Mass spectrum, m/e (relative intensity) 291 (M$^+$1, 4), 165 (4), 140 (9), 139 (92), 138 (52), 124 (6), 109 (71), 97 (60), 96 (100).

Elemental Analysis: Calculated: 62.02% C; 5.21% H; 9.65% N. Found: 61.76% C; 5.41% H; 9.43% N.

EXAMPLE 29

(D,L)-α-Acetamido-N-(2,5-difluorobenzyl)-2-furanacetamide.

Using 2,5-difluorobenzylamine (1.30 g, 9.0 mmol) and racemic α-acetamido-2-furanacetic acid (1.50 g, 8.2 mmol) gave the desired product.

Yield 1.60 g (64%).

$R_f$ 0.38 (96:4 chloroform/methanol).

mp 177°–178° C. (recrystallized from ethyl acetate).

$^1$H NMR (DMSO-$d_6$) δ 1.89 (s, COCH$_3$), 4.31 (d, J=5.5 Hz, CH$_2$), 5.55 (d, J=7.7 Hz, CH), 6.32 (s, C$_4$H), 6.43 (s, CH$_3$H), 7.22–7.25 (m, 3 ArH), 7.62 (s, C$_5$H), 8.62 Hz, NH), 8.78 (t, J=5.5 H, NH).

$^{13}$C NMR (DMSO-$d_6$) 22.30 (COCH$_3$), 35.98 (d, $J_{CF}$=5.8 Hz, CH$_2$), 51.02 (CH), 107.81 (C$_4$), 110.58 (C$_3$), 115.06 (dd, $J_{CF}$=19.5, 25.6 Hz, C$_{3'}$ or C$_{6'}$), 115.16 (dd, $J_{CF}$=15.6, 24.7 Hz, C$_{3'}$ or C$_{6'}$), 116.52 (dd, $J_{CF}$=10.1, 23.9 Hz, C$_{4'}$), 127.98 (dd, $J_{CF}$=9.2, 17.7 Hz, C$_{1'}$), 142.69 (C$_5$), 150.78 (C$_2$), 155.89 (d, $J_{CF}$=239.0 Hz, C$_{2'}$ or C$_{5'}$), 158.18 (d, $J_{CF}$=238.8 Hz, C$_{2'}$ or C$_{5'}$), 168.38 (COCH$_3$), 169.35 (CONH) ppm.

IR (KBr) 3230, 1620, 1520, 1480, 1360, 1260, 1230, 1180, 1140, 1000, 860, 810, 730, 710 cm$^{-1}$.

Mass spectrum, m/e (relative intensity) 309 (M$^+$+1, 1), 266 (1), 222(1), 165 (5), 140 (5), 139 (61), 138 (36), 127 (37), 97 (44), 96 (100).

Elemental Analysis: Calculated: 58.44% C; 4.58% H; 9.09% N. Found: 58.68% C; 4.69% H; 8.87% N.

EXAMPLE 30

(D,L)-α-Acetamido-N-(2,6-difluorobenzyl)-2-furanacetamide.

Making use of 2,6-difluorobenzylamine (1.30 g, 9.0 mmol) and racemic α-acetamido-2-furanacetic acid (1.50 g, 8.2 mmol) the desired product was form Yield 1.90 g (73%).

mp 237°–239° C. (recrystallized from ethanol).

$^1$H NMR (DMSO-d$_6$) δ 1.86 (COCH$_3$), 4.33 (d, J=4.5 Hz, CH$_2$), 5.53 (d, J=8.3 Hz, CH, 6.17 (s, C$_4$H), 6.38 (s, C$_3$H), 7.05–7.10 (m, 2 ArH, 7.36–7.41 (m, 1 ArH, 7.60 (s, C$_5$H), 8.52 (d, J=8.3 Hz, NH), 8.66 (t, J=4.5 Hz, NH).

$^{13}$C NMR (DMSO-d$_6$) δ 22.33 (COCH$_3$), 30.74 (t, J$_{CF}$=4.4 Hz, CH$_2$), 50.48 (CH), 107.24 (C$_4$), 110.40 (C$_3$), 111.61 (dd, J$_{CF}$=8.0, 25.1 Hz, C$_3$', C$_5$'), 113.67 (t, J$_{CF}$=19.5 Hz, C$_1$'), 129.98 (t, J$_{CF}$=10.5 Hz, C$_4$'), 142.50 (C$_5$), 151.23 (C$_2$), 160.93 (d, J$_{CF}$=248.1, C$_2$' or C$_6$'), 161.10 (d, J$_{CF}$=248.1 Hz, C$_2$' or C$_6$'), 167.59 (COCH$_3$), 169.00 (CONH) ppm.

IR (KBr) 3230, 1620, 1530, 1460, 1360, 1320, 1260, 1220, 1160, 1140, 1030, 1000, 820, 780, 750, 740, 710 cm$^{-1}$.

Mass spectrum, m/e (relative intensity) 309 (M$^+$+1, 4), 265 (2), 165 (4), 147 (7), 140 (8), 139 (87), 138 (36), 127 (54), 97 (58), 96 (100).

Elemental Analysis: Calculated: 58.44% C; 4.58% H; 9.09% N. Found: 58.62% C; 4.74H; 8.89% N.

EXAMPLE 31

(D)-(–)α-Acetamido-N-benzyl-2-furanacetamide

Starting with D-α-acetamido-2-furanacetic acid (2.45 g, 13.38 mmol) and benzylamine (1.43 g, 13.38 mmol), the desired product was obtained.

Yield: 2.54 g (70%) The product was further recrystallized from ethyl acetate to give the title compound Yield: 2.30 g mp 196°–197° C.

$[α]^{26}{}_{D[c=1, MeOH]}$=–78.3°. Addition of R(–)-mandelic acid to a CDCl$_3$ solution of the product gave only one signal for the acetamide methyl protons.

Mass spectrum, m/e (relative intensity) 272 (M$^+$, 2), 184 (2), 165 (2), 140 (8), 139 (88), 138 (34), 97 (46), 96 (100), 91 (63).

Elemental Analysis: Calculated: 66.16% C; 5.92% H; 10.29% Found: 66.09% C; 6.01% H; 10.38% N.

EXAMPLE 32

(L)-(+)-α-Acetamido-N-benzyl-2-furanacetamide.

Using L-α-acetamido-2-furanacetic acid (2.83 g, 15.46 mmol) and benzylamine (1.65 g, 15.46 mmol) gave 3.80 g of the enriched desired product. $^1$H NMR analysis with R(–)-mandelic acid showed that it was greater than 80% enriched in the title compound. The pure L-enantiomer was obtained by recrystallization from absolute ethanol.

Yield: 1.60 g.

mp 196°–197° C.

$[α]^{26}{}_{D[c=1, MeOH]}$=+79.0°.

Mass spectrum, m/e (relative intensity) 273 (M$^+$+1, 3), 229 (2), 214 (2), 184 (1), 165 (7), 157 (4), 140 (33), 139 (100), 138 (95), 97(98), 96 (100), 91 (98).

Elemental Analysis: Calculated: 66.16% C; 5.92% H; 10.29% N. Found: 65.89% C; 5.86% H; 10.42% N.

EXAMPLE 33

Resolution of (D,L)-α-Acetamido-2-furanacetic acid Using (R)-(+)-α-Methylbenzylamine and (S)-(–)-α-Methylbenzylamine.

(R)-(+)-α-Methylbenzylamine (13.22 g, 0.11 mol) was added to an absolute ethanol solution (550 mL) of racemic α-acetamido-2-furanacetic acid (20.00 g, 0.11 mol). The resulting solution was cooled in the freezer overnight. The white precipitate (12.00 g) which separated upon cooling was filtered, and the mother liquid evaporated to give a salt which was later used for obtaining L-α-acetamido-2-furanacetic acid. The initial salt was recrystallized (3×) from absolute ethanol to yield 4.00 g of the pure diasteromeric salt.

mp 173°–175° C.

$[α]^{26}$D[c=1, MeOH]=–108°.

Elemental Analysis Calculated: 63.14% C; 6.62% H; 9.21% N. Found: 63.19% C; 6.62% H; 9.12% N.

The purified salt was treated with 5% aqueous NH$_4$OH solution, extracted with ethyl ether (3×50 mL), and then acidified with a 8.5% aqueous solution of H$_3$PO$_4$ and then extracted with ethyl acetate (3×100 mL) to yield 2.45 g (25%) of D-α-acetamido-2-furanacetic acid.

mp 69°–171° C.

$[α]^{26}$D[c=1, MeOH]=–184.2°.

Elemental Analysis: Calculated: 52.46% C; 4.95% H; 7.65% N. Found: 52.17% C; 4.89% H; 7.56% N.

The salt obtained after evaporation of the main mother liquor was hydrolysed with 5% aqueous NH$_4$OH solution to give 10.10 g of the enriched L-α-acetamido-2-furanacetic acid $[[α]^{26}$D[c=1, MeOH]=+47.7°]. (S)-(–)-methylbenzylamine (6.70 g, 0.055 mol) was added to a solution of enriched L-α-acetamido-2-furanacetic acid (10.10 g, 0.055 mol) in absolute ethanol (275 mL). The white precipitate of the diasteroemeric salt (8.10 g) that separated upon cooling the solution in the freezer (1 h) was filtered. The salt was recrystallized from absolute ethanol (3×) to yield 3.00 g of the salt.

mp 172°–174° C.

$[α]^{26}$D[c=1, MeOH]=+106°.

Elemental Analysis: Calculated: 63.14% C; 6.62% H; 9.21% N. Found: 63.18% C; 6.47% H; 9.00% N.

The salt from the third recrystallization was treated with a 5% aqueous NH$_4$OH solution and extracted with ethyl ether (3×50 mL), and then acidified with a 8.5% aqueous solution of H$_3$PO$_4$, and then extracted with ethyl acetate (3×100 mL) to give 1.63 g (32%) of L-α-acetamido-2-furanacetic acid.

mp 169°–171° C.

$[α]^{26}$D[c=1, MeOH]=+182°.

EXAMPLE 34

Enzymatic Separation of D(–)α-acetamido-2-furanacetic acid (R-19) from DL (±)α-acetamido-2-furanacetic acid.

DL (±)α-acetamido-2-furanacetic acid (2.00 g, 10.9 mmol) was suspended in deionized H$_2$O (600 mL). An aqueous solution of LiOH (1N) was added to this suspension dropwise until all of the acid had dissolved and the pH was 7.2 Acylase 1, Grade II (20 mg, activity=900 units/mg, Sigma Chemical Company, Cat. No. A 8376) was then added to the above solution and the mixture stirred at 34°–37° C. (41 h). The suspension was then cooled to room temperature and acidified to pH 1.5 with aqueous 1N HCl. The suspended material was filtered, and the filtrate was saturated with solid NaCl, and then extracted with ethyl acetate (3×250 mL). The combined ethyl acetate extracts was dried ($Na_2SO_4$). The solvent was removed in vacuo and the residue was triturated with ethyl acetate (10 mL). The white solid (0.75 g) that remained was filtered and was pure D(−)α-acetamido-2-furanacetic acid; mp 168°–169° C., mixed mp with an authentic sample 168°–169° C.; $[\alpha]_D^{26}$ [c=1, MeOH]=−184.3°.

EXAMPLE 35

Preparation of D,L-α-Acetamido-2-furanacetic Acid.

An ethereal solution of $ZnCl_2$ (1N, 28 mL, 0.028 mol) was added to a stirred solution of ethyl acetamido-2-bromoacetate (4.40 g, 0.019 mol) and furan (11.23 g, 0.165 mol) in dry tetrahydrofuran (100 mL), and allowed to stir at room temperature (5 h). The mixture was then treated with $H_2O$ (50 mL), the organic phase separated, and the aqueous layer extracted with $CH_2Cl_2$ (2×100 mL). The organic layers were combined, dried ($Na_2SO_4$) and the volatile materials were removed by distillation in vacuo to give approximately 4.00 g (97%) of light-brown semi-solid material. TLC analysis showed a major spot at $R_f$ 0.30 (99:1 chloroform/methanol). The desired compound, D,L-ethyl α-acetamido-2-furanacetate, was purified by flash column chromatography on silica gel using 99:1 chloroform/methanol as the eluent to give 3.60 g (87%) of a beige solid.

mp 68°–70° C.

D,L-Ethyl α-acetamido-2-furanacetate (4.00 g, 19 mmol) was dissolved in 90:10 ethanol/water (150 mL) and then KOH (2.00 g, 35 mmol) was added and the resulting solution stirred at room temperature (48 h). The reaction was concentrated in vacuo and the residue diluted with $H_2O$ and then washed with ethyl ether (3×50 mL). The aqueous layer was then made acidic with a 8.5% aqueous solution of $H_3PO_4$ and extracted with ethyl acetate (3×150 mL). The organic layers were combined, dried ($Na_2SO_4$), evaporated to dryness in vacuo to give the desired compound.

Yield: 2.65 g (76%).

$R_f$ 0.37 (8:1:1 isopropanol/$NH_4OH$/$H_2O$).

mp 172°–174° C.

EXAMPLE 36

Synthesis of (D,L)-α-Acetamido-4-pentenoic Acid-N-benzylamide.

4-Methylmorpholine (0.55 g, 5.40 mmol) was added to a stirred solution of 2-acetamido-4-pentenoic acid (0.81 g, 5.18 mmol) in dry tetrahydrofuran (60 mL) at −10° to −15° C. under $N_2$. After stirring (2 min), isobutyl chloroformate (0.75 g, 5.70 mmol) was added leading to the precipitation or a white solid. The reaction was allowed to proceed for 2 additional minutes and then a solution of benzylamine (0.61 g, 5.70 mmol) in tetrahydrofuran (10 mL) was added slowly at −10° to −15° C. After stirring (5 min) at room temperature, the insoluble salt was removed by filtration. The filtrate was evaporated to dryness and the residue was triturated with ethyl acetate, and the remaining white solid was filtered to yield the desired product.

Yield 0.81 g (64%).

$R_f$ 0.36 (4% methanol/chloroform).

mp 118°–120° C. (recrystallized from ethyl acetate/cyclohexane).

$^1H$ NMR (DMSO-$d_6$) δ 1.83 (s, $COCH_3$), 2.22–2.49 (m, $CH_2CH=CH_2$), 4.26 (d, J=5.3 Hz, $CH_2Ph$), 4.25–4.33 (m, CH), 4.99–5.09 (m, $CH_2CH=CH_2$), 7.21–7.29 (m, 5 PhH), 8.05 (d, J=7.6 Hz, NH), 8.46 (br s, NH).

$^{13}C$ NMR (DMSO-$d_6$) 22.41 ($COCH_3$), 36.24 ($CH_2CH=CH_2$), 41.91 ($CH_2Ph$), 52.20 (CH), 117.15 ($CH_2CH=CH_2$), 126.54 ($C_4$), 126.99 ($2C_{2'}$ or $2C_{3'}$), 128.04 ($2C_{2'}$ or $2C_{3'}$), 134.25 ($CH_2CH=CH_2$), 139.22 ($C_{1'}$), 169.02 ($COCH_3$), 170.96 (CONH) ppm.

Mass spectrum, m/e (relative intensity) 246 ($M^+$, 4), 205 (4), 163 (15), 140 (8), 106 (33), 91 (77), 70 (100).

Elemental Analysis: Calculated: 68.27% C; 7.37% H; 11.37% N. Found: 68.55% C; 7.31% H; 11.48% N.

Mass spectrum m/e (relative intensity) 292 ($M^+$+1, 1), 233 (8), 158 (19), 157 (100), 116 (26), 115 (100), 106 (29), 91 (72).

Elemental Analysis: Calculated: 61.84% C; 7.26% H; 14.42% N. Found: 61.67% C; 7.10% H; 14.14% N.

EXAMPLE 37

Synthesis or (D,L)-2-Acetamido-N-benzyl-2-(1-morpholine)acetamide.

A mixture of ethyl 2-acetamido-2-(1-morpholine)acetate (0.59 g, 2.56 mmol), benzylamine (0.28 g, 2.82 mmol) and sodium cyanide (0.01 g, 0.26 mmol) in methanol (5 mL) was stirred at 50°–55° C. for 18 hr. The solvent was removed in vacuo and the residue triturated with ethyl acetate (5 mL). The white solid (0.35 g) that remained was collected by filtration and identified as the desired compound. The filtrate was concentrated and the residue purified by flash column chromatography (2% methanol/chloroform) on $SiO_2$. The initial fractions gave a trace amount (0.09 g) or (D,L)-2-acetamido-N-benzyl-2-(N-benzylamine)acetamide. Continued elution gave additional amounts (0.20 g) of the title compound.

(D,L)-2-Acetamido-N-benzyl-2-(N-benzylamine) acetamide:

Yield: 0.09 g (11%).

mp 135°–138° C.

$^1H$ NMR (DMSO-$d_6$) δ 1.83 (s, $COCH_3$), 3.56 (d, J=13.6 Hz, NHCH), 3.66 (d, J=13.6 Hz, NHCH), 4.23 (d, J=5.4 Hz, $CH_2$), 4.89 (d, J=8.0 Hz, CH), 7.05–7.38 (m, 10 PhH), 8.20 (d, J=8.0 Hz, NH), 8.51 (t, J=5.4 Hz, NH).

$^{13}C$ NMR (DMSO-$d_6$) 22.63 ($COCH_3$), 42.11 ($CH_2$), 48.57 ($NHCH_2$), 64.41 (CH), 126.65 ($C_4$), 126.70 ($C_{4'}$), 127.13, 128.00, 128.13, 128.22, 139.24 ($C_1$ or $C_{1'}$), 140.12 ($C_1$ or $C_{1'}$), 169.61 ($COCH_3$), 169.90 (CONH) ppm.

(D,L)-2-Acetamido-N-2-benzyl-2-(1-morpholine) acetamide.

Yield: 0.48 g (64%).

$R_f$ 0.35 (4% methanol/chloroform).

mp 171°–172° (recrystallized from ethyl acetate).

$^1H$ NMR (DMSO-$d_6$) δ 1.86 (s, $COCH_3$), 2.30–2.40 (m, $CH_2NCH_2$), 3.51 (br s, $CH_2OCH_2$), 4.18–4.33 (m, $CH_2$), 5.07 (d, J=8.9 Hz, CH), 7.18–7.25 (m, 5 PhH), 8.23 (d, J=8.9 Hz, NH), 8.58 (br s, NH).

$^{13}C$ (DMSO-$d_6$) 22.39 ($COCH_3$), 42.20 ($CH_2$), 48.43 ($CH_2NCH_2$), 66.03 (CH), 69.24 ($CH_2OCH_2$), 126.76 ($C_{4'}$), 127.13 ($2C_{2'}$ or $2C_{3'}$), 128.23 ($2C_{2'}$ or $2C_{3'}$), 139.42 ($C_{1'}$),

EXAMPLE 38

Synthesis of (D,L)-Ethyl 2-acetamido-2-(ethylamino) acetate.

A cold (−78° C.) solution of ethyl 2-acetamido-2-bromoacetate (2.10 g, 9.38 mmol) in dry tetrahydrofuran (80 mL) was added slowly into a cooled (−78° C.) tetrahydrofuran (20 mL) solution of methylamine (1.40 g, 31.04 mmol) over a period of 20 min. The reaction was stirred at −78° C. (1 h), and then at room temperature (1 h). The precipitated salt was filtered and the filtrate concentrated. The residue was purified by flash column chromatography on $SiO_2$ using 3% methanol/chloroform as the eluent to yield the desired compound as a light yellow oil.

Yield: 0.90 (51%).

$R_f$ 0.36 (4% methanol/chloroform).

$^1$H NMR (CDCl$_3$) 0.93 (t, J=6.7 Hz, NHCH$_2$CH$_3$), 1.12 (t, J=6.8 Hz, OCH$_2$CH$_3$), 1.87 (s, COCH$_3$), 2.48 (q, J=6.7 Hz, NHCH$_2$CH$_3$), 4.05 (q, J=6.8 Hz, OCH$_2$CH$_3$), 5.05 (d, J=7.1 Hz, CH), 7.09 (d, J=7.1 Hz, NH).

$^{13}$C NMR (CDCl$_3$) 13.64 (NHCH$_2$CH$_3$), 14.55 (OCH$_2$CH$_3$), 22.53 (COCH$_3$), 39.06 (NHCH$_2$CH$_3$), 61.38 (CH), 64.14 (OCH$_2$CH$_3$), 170.09 (COCH$_3$), 170.20 (COOCH$_2$CH$_3$) ppm.

EXAMPLE 39

Using the procedures described herein, the following examples are also prepared:
(D,L)α-Acetamido-N-benzyl-3-furanacetamide
(D,L)α-Acetamido-N-(2-fluorobenzyl)-3-furanacetamide
(D,L)α-Acetamido-N-(3-fluorobenzyl)-3-furanacetamide
(D,L)α-Acetamide-N-(4-fluorobenzyl)-3-furanacetamide
α-Acetamide-N-benzyl-2-aminoacetamide
Preparation of α-Heteroatom Substituted Amino Acids, Synthesis of Ethyl 2-Acetamido-2-substituted Acetates.
General Procedure.

A cooled (−78° C.) solution of ethyl 2-bromo-2-acetamidoacetate (1 equiv) in THF (1 mmol/10 mL) was added slowly to a THF (1 mmol/4 mL) solution of the nitrogen nucleophile (5–10 equiv) at −78° C. The reaction was stirred at this temperature (0.5 h) and then at room temperature (1 h). The insoluble materials were filtered and washed with THF. The filtrate was concentrated in vacuo and the residue was purified by flash chromatography on $SiO_2$ gel (using the indicated solvent as the eluent) to give the desired product.

Using this procedure the following examples were prepared.

EXAMPLE 40

Synthesis of Ethyl 2-Acetamido-2-aminoacetate.

Ethyl 2-bromo-2-acetamidoacetate (2.00 g, 8.93 mmol) and liquid NH$_3$ (5–6 equiv) yielded a light brown residue, which on purification by flash column chromatography on $SiO_2$ gel (5% MeOH/CHCl$_3$) gave the desired product as a yellow oil.

Yield: 1.00 g (70%).

$R_f$ 0.21 (5% MeOH/CHCl$_3$).

$^1$H NMR (CDCl$_3$) δ 1.31 (t, J=7.1 Hz, 3H), 2.03 (s, 3H), 2.61 (br s, 2H), 4.24 (q, J=7.1 Hz, 2H), 5.21 (d, J=7.1 Hz, 1H), 7.50 (d, J=7.1 Hz, 1H).

$^{13}$C NMR (CDCl$_3$) 13.72, 22.68, 59.70, 61.73, 170.40, 170.68 ppm.

EXAMPLE 41

Synthesis of Ethyl 2-Acetamido-2-(methylamino)acetate.

Use of ethyl 2-bromo-2-acetamidoacetate (2.00 g, 8.93 mmol) and MeNH$_2$ (2.50 g, 80.6 mmol) gave an oily residue (1.50 g). The residue was purified by flash column chromatography on $SiO_2$ gel (3% MeOH/CHCl$_3$) to yield the desired product as an oil.

Yield: 1.00 g (65%).

$^1$H NMR (CDCl$_3$) δ 1.32 (t, J=7.1 Hz, 3H), 2.07 (s, 3H), 2.36 (s, 3H), 4.26 (q, J=7.1 Hz, 2H), 5.20 (d, J=7.4 Hz, 1H), 6.60 (br s, 1H).

$^{13}$C NMR (CDCl$_3$) 14.02, 23.06, 30.84, 62.04, 65.72, 170.09, 170.40 ppm.

EXAMPLE 42

Synthesis of Ethyl 2-Acetamido-2-(N,N-dimethylamino)acetate.

Ethyl 2-bromo-2-acetamidoacetate (2.00 g, 8.93 mmol) and Me$_2$NH (5–6 equiv) gave the desired product as a yellow oil.

Yield: 1.50 g (89%).

$^1$H NMR (CDCl$_3$) δ 1.25 (t, J=7.1 Hz, 3H), 2.02 (s, 3H), 2.33 (s, 6H), 4.10–425 (m, 2H), 5.24 (d, J=8.3 Hz, 1H), 6.59 (d, J=8.3 Hz, 1H).

$^{13}$C NMR (CDCl$_3$) 14.05, 23.00, 40.28 (2 C), 61.84, 69.24, 169.38, 170.57 ppm.

EXAMPLE 43

Synthesis of Ethyl 2-Acetamido-2-(4-morpholine)acetate.

Using morpholine (1.71 g, 19.64 mmol) and ethyl 2-bromo-2-acetamidoacetate (2.00 g, 8.93 mmol) gave an oily residue, which was purified by flash column chromatography on $SiO_2$ gel (2% MeOH/CHCl$_3$) to give the desired product as a thick oil.

Yield: 1.90 g (93%).

$R_f$ 0.29 (3% MeOH/CHCl$_3$).

$^1$H NMR (CDCl$_3$) δ 1.32 (t, J.=6.8 Hz, 3H), 2.07 (s, 3H), 2.43–2.72 (m, 4H), 3.58–3.78 (m 4H), 4.26 (q, J=6.8 Hz, 2H), 5.27 (d, J=7.9 Hz, 1H), 6.39 (d, J=7.9 Hz, 1H).

$^{13}$C NMR (CDCl$_3$) 14.21, 23.25, 48.47 (2 C), 62.06, 66.71 (2 C), 69.22, 169.00, 170.46 ppm.

EXAMPLE 44

Synthesis of Ethyl 2-Acetamido-2-(N-anilino)acetate.

Use of aniline (1.83 g, 19.6 mmol) and ethyl 2-bromo-2-acetamidoacetate (2.00 g, 8.93 mmol) provided a brown residue which was purified by flash column chromatography on $SiO_2$ gel (CHCl$_3$-2% MeOH/CHCl$_3$ gradient) to yield the desired product.

Yield: 1.80 g (85%).

$R_f$ 0.52 (4% MeOH/CHCl$_3$).

mp 87°–89° C. (recrystallized from ethyl acetate/petroleum ether).

$^1$H NMR (CDCl$_3$) δ 1.29 (t, J=7.1 Hz, 3H), 1.84 (s, 3H), 4.27 (q, J=7.1 Hz, 2H), 5.89 (d, J=8.2 Hz, 1H), 6.43 (d, J=8.2 Hz, 1H), 6.68–6.71 (m, 2H), 6.80–6.83 (m, 1H), 7.17–7.22 (m, 2H). The remaining amino proton was not detected.

$^{13}$C NMR (CDCl$_3$) 13.96, 22.98, 60.19, 62.41, 113.87 (2 C), 119.29, 129.37 (2 C), 144.09, 169.77, 170.14 ppm.

IR (KBr) 3340, 1720, 1635, 1590, 1490, 730, 710 cm$^{-1}$.

Mass spectrum (FD) 237 (M$^{30}$+1).

Elemental analysis Calculated for $C_{12}H_{16}N_2O_3$ 61.00% C; 6.83% H; 11.86% N. Found 60.88% C; 6.56% H; 12.00% N.

EXAMPLE 45

Synthesis of Ethyl 2-Acetamido-2-(N-(3-pyrazolylamino)) acetate.

Using ethyl 2-bromo-2-acetamidoacetate (2.00 g, 8.92 mmol) and 3-aminopyrazole (1.85 g, 22.32 mmol) and purification of the reaction product by chromatography on $SiO_2$ gel (2% MeOH/$CHCl_3$) gave the desired product as a yellow oil.

Yield: 1.80 g (89%).

$R_f$ 0.35 (8% MeOH/$CHCl_3$).

$^1H$ NMR ($CDCl_3$) δ 1.21 (t, J=7.1 Hz, 3H), 1.89 (s, 3H), 4.20 (q, J=7.1 Hz, 2H), 5.64 (d, J=1.8 Hz, 1H), 5.71 (br s, 1H), 5.73 (d, J=7.1 Hz, 1H), 7.29 (d, J=1.8 Hz, 1H), 7.98 (d, J=7.1 Hz, 1H). The remaining amino proton was not detected.

$^{13}C$ NMR ($CDCl_3$) 13.73, 22.49, 61.41, 62.02, 91.79, 130.53, 153.02, 169.96, 170.93 ppm.

EXAMPLE 46

Synthesis of Ethyl 2-Acetamido-2-hydroxyamino)acetate.

Using ethyl 2-bromo-2-acetamidoacetate (2.10 g, 9.37 mmol) and anhydrous $NH_2OH$ (0.93 g, 28.00 mmol) gave an oily residue. The residue was purified by flash column chromatography on $SiO_2$ gel (5% MeOH/$CHCl_3$) to give the desired product. The product was recrystallized from EtOH to give a white flaky solid.

Yield: 1.00 g (61%).

$R_f$ 0.24 (5% MeOH/$CHCl_3$).

mp 119°–121° C.

$^1H$ NMR (DMSO-$d_6$) δ 1.19 (t, J=6.9 Hz, 3H), 1.87 (s, 3H), 4.10 (q, J=6.9 Hz, 2H), 5.09 (dd, J=4.0, 8.0 Hz, 1H), 6.06 (br s, 1H), 7.63 (s, 1H), 8.50 (d, J=8.0 Hz, 1H).

$^{13}C$ NMR (DMSO-$d_6$) 14.05, 22.46, 60.82, 67.37, 169.19, 169.48 ppm.

IR (KBr) 3300, 1750, 1660, 1540, 1390, 610 cm$^{-1}$.

Mass spectrum (FD) 177 ($M^+$+1).

Elemental analysis Calculated for $C_6H_{12}N_2O_4$ 40.91% C; 6.87% H; 15.90% N. Found 40.79% C; 6.87% H; 15.90% N.

EXAMPLE 47

Synthesis of Ethyl 2-Acetamido-2-(N-(N-methylhydroxyamino))acetate.

MeNHOH (17.39 mmol) (prepared from MeNHOH.HCl (2.00 g, 23.95 mmol) and NaOMe (0.94 g, 17.39 mmol)), and ethyl 2-bromo-2-acetamidoacetate (1.00 g, 4.46 mmol) gave an oily residue. The residue was triturated with EtOAc (5 mL) and the solid that remained was filtered and recrystallized from EtOH to give the desired product as a white solid.

Yield: 0.70 g (82%).

$R_f$ 0.34 (5% MeOH/$CHCl_3$).

mp 148°–150° C.

$^1H$ NMR (DMSO-$d_6$) δ 1.17 (t, J=7.0 Hz, 3H), 1.89 (s, 3H), 2.37 (s, 3H), 4.00–4.20 (m, 2H), 5.04 (d, J=9.2 Hz, 1H), 8.17 (s, 1H), 8.43 (d, J=9.2 Hz, 1H).

$^{13}C$ NMR (DMSO-$d_6$) 14.04, 22.28, 43.78, 60.79, 71.46, 168.29, 170.23 ppm.

IR (KBr) 3320, 3200 (br), 1760, 1660, 1530, 1470, 720, 640 cm$^{-1}$.

Mass spectrum (FD) 192 ($M^+$+1).

Elemental analysis Calculated for $C_7H_{14}N_2O_4$·0.25 $H_2O$ 43.18% C; 7.51% H; 14.39% N. Found 43.28% C; 7.25% H; 14.64% N.

EXAMPLE 48

Synthesis of Ethyl 2-Acetamido-2-(N-(N,O-dimethylhydroxyamino))acetate.

MeNHOMe (17.40 mmol) (prepared from MeNHOMe.HCl (2.18 g, 22.32 mmol) and NaOMe (0.94 g, 17.40 mmol)) and ethyl 2-bromo-2-acetamidoacetate (1.00 g, 4.46 mmol) gave a residue which was purified by flash column chromatography on $SiO_2$ gel (1% MeOH/$CHCl_3$) to give the desired product as an oil.

Yield: 0.60 g (66%).

$R_f$ 0.53 (2% MeOH/$CHCl_3$).

$^1H$ NMR ($CDCl_3$) δ 1.35 (t, J=7.0 Hz, 3H), 2.12 (s, 3H), 2.62 (s, 3H), 3.46 (s, 3H), 4.30 (q, J=7.0 Hz, 2H), 5.36 (d, J=8.9 Hz, 1H), 6.66 (d, J=8.9 Hz, 1H).

$^{13}C$ NMR ($CDCl_3$) 14.06, 22.89, 40.30, 60.01, 61.89, 70.16, 168.14, 170.53 ppm.

Synthesis of 2-Acetamido-N-benzyl-2-substituted Acetamides.

General Procedure.

A mixture of the ethyl 2-substituted-2-acetamidoacetate (1 equiv), benzylamine (1.2 equiv), and NaCN (0.1 equiv) in MeOH (1 mmol/25 mL) was stirred at 45°–50° C. (18 h). The solvent was removed in vacuo and the residue was purified using either trituration with EtOAc or flash column chromatography on $SiO_2$ gel with the indicated solvent as the eluent.

Using this procedure the following examples were prepared.

EXAMPLE 49

Synthesis of 2-Acetamido-N-benzyl-2-aminoacetamide.

Ethyl 2-acetamido-2-aminoacetate (1.00 g, 6.25 mmol), benzylamine (0.80 g, 7.5 mmol) and NaCN (0.03 g, 0.61 mmol) gave a residue which solidified on standing (18 h). The reaction mixture was triturated with EtOAc (20 mL). The white solid which remained was filtered and then further purified by recrystallization from EtOAc.

Yield: 1.00 g (72%).

$R_f$ 0.21 (5% MeOH/$CHCl_3$).

mp 131°–133° C. (dec.).

$^1H$ NMR (DMSO-$d_6$) δ 1.83 (s, 3H), 2.35 (br s, 2H), 4.28 (d, J=4.4 Hz, 2H), 4.91 (d, J=7.0 Hz, 1H), 7.20–7.32 (m, 5H), 8.31 (br s, 1H), 8.51 (br s, 1H).

$^{13}C$ NMR (DMSO-$d_6$) 22.6, 42.05, 60.29, 126.67, 127.10 (2 C), 128.18 (2 C), 139.23, 169.24, 170.67 ppm.

IR (KBr) 3300, 1650 (br), 1530 (br), 1450, 740 cm$^{-1}$.

Mass spectrum, m/e (relative intensity) 222 ($M^+$+100), 221 ($M^+$, 29), 133 (8).

Elemental analysis Calculated for $C_{11}H_{15}N_3O_2$ 59.71% C; 6.83% H; 18.99% N. Found 59.86% C; 6.88% H; 18.72% N.

EXAMPLE 50

Synthesis of 2-Acetamido-N-benzyl-2-(methylamino) acetamide.

Ethyl 2-acetamido-2-(methylamino)acetate (1.50 g, 8.63 mmol), benzylamine (1.11 g, 10.35 mmol) and NaCN (0.04 g, 0.82 mmol) gave a brown residue which was purified by flash column chromatography on SiO$_2$ gel (2% MeOH/CHCl$_3$) to yield the desired product.

Yield: 1.00 g (49%).

R$_f$ 0.33 (3% MeOH/CHCl$_3$).

mp 115°–117° C. (recrystallized from ethyl acetate/petroleum ether).

$^1$H NMR (DMSO-d$_6$) δ 1.87 (s, 3H), 2.18 (s, 3H), 4.20–4.29 (m, 2H), 4.87 (d, J=7.9 Hz, 1H), 7.24–7.35 (m, 5H), 8.14 (d, J=7.9 Hz, 1H), 8.55 (br s, 1H). The remaining amino proton was not detected.

$^{13}$C NMR (DMSO-d$_6$) 22.52, 31.37, 42.04, 65.99, 126.68, 127.12 (2 C), 128.18 (2 C), 139.28, 169.51, 169.83 ppm.

IR (KBr) 3240, 1610 (br), 1500 (br), 1430, 725, 670 cm$^{-1}$.

Elemental analysis Calculated for C$_{12}$H$_{17}$N$_3$O$_2$ 61.26% C; 7.28% H; 17.86% N. Found 61.12% C; 7.01% H; 17.71% N.

EXAMPLE 51

Synthesis of 2-Acetamido-N-benzyl-2-(ethylamino)acetamido.

Using ethyl 2-acetamido-2-(ethylamino)acetate (0.90 g, 4.79 mmol), benzylamine (0.62 g, 5.75 mmol), and NaCN (0.03 g, 0.51 mmol) gave an oily residue which was purified by flash column chromatography on SiO$_2$ gel (3% MeOH/CHCl$_3$) to give the desired product as a white solid.

Yield: 0.35 g (29%).

R$_f$ 0.34 (4% MeOH/CHCl$_3$).

mp 123°–125° C. (recrystallized from ethyl acetate/hexane).

$^1$H NMR (DMSO-d$_6$) δ 0.93 (t, J=6.8 Hz, 3H), 1.81 (s, 3H), 2.08 (br s, 1H), 2.40–2.48 (m, 2H), 4.22 (d, J=5.5 Hz, 2H), 4.90 (d, J=7.8 Hz, 1H), 7.20–7.27 (m, 5H), 8.08 (d, J=7.8 Hz, 1H), 8.48 (t, J=5.5 Hz, 1H).

$^{13}$C NMR (CDCl$_3$) 15.14, 22.97, 37.65, 43.53, 65.68, 127.44 (2 C), 127.50, 128.64 (2 C), 137.73, 169.75, 171.20 ppm.

IR (KBr) 3250, 1620 (br), 1510 (br), 1450 (br), 740, 680 cm$^{-1}$.

Elemental analysis Calculated for C$_{13}$H$_{19}$N$_3$O$_2$ 62.63% C; 7.68% H; 16.85% N. Found 62.69% C; 7.49% H; 16.65% N.

EXAMPLE 52

Synthesis of 2-Acetamido-N-benzyl-2-(N-anilino)acetamido.

Employing ethyl 2-acetamido-2-(N-anilino)acetate (2.00 g, 8.47 mmol), benzylamine (1.09 g, 10.00 mmol), and NaCN (0.04 g, 0.84 mmol) gave a white solid which separated during the course of the reaction. The precipitate was filtered and purified by recrystallization from absolute EtOH to give the desired product.

Yield: 1.10 g (44%).

mp 183°–185° C.

$^1$H NMR (DMSO-d$_6$) δ 1.84 (s, 3H), 4.31 (d, J=5.8 Hz, 2H), 5.67 (t, J=8.1 Hz, 1H), 6.04 (d, J=8.1 Hz, 1H), 6.59–6.64 (m, 1H), 6.70–6.72 (m, 2H), 7.06–7.11 (m, 2H), 7.20–7.33 (m, 5H), 8.41 (d, J=8.1 Hz, 1H), 8.72 (t, J=5.8 Hz, 1H).

$^{13}$C NMR (DMSO-d$_6$) 22.46, 42.25, 60.42, 113.21 (2 C), 117.22, 126.72, 127.16 (2 C), 128.18 (2 C), 128.77 (2 C), 138.99, 145.88, 168.65, 169.70 ppm.

IR (KBr) 3270, 1630, 1520, 1490, 1430, 740, 690 cm$^{-1}$.

Mass spectrum, m/e (relative intensity) 297 (M$^+$, 2), 239 (7), 164 (28), 163 (100), 122 (20), 121 (100), 106 (47), 104 (65), 93 (63), 91 (77).

Elemental analysis Calculated for C$_{17}$H$_{19}$N$_3$O$_2$ 68.67% C; 6.44% H; 14.13% N. Found 68.94% C; 6.42% H; 13.92% N.

EXAMPLE 53

Synthesis of 2-Acetamido-N-benzyl-2-(N-(3-pyrazolylamino))acetamide.

A solution of ethyl 2-acetamido-2-(N-(3-pyrazolylamino)) acetate (1.60 g, 7.1 mmol) in MeOH (40 mL) containing benzylamine (0.83 g, 7.8 mmol) and NaCN (50 mg, 1 mmol) was stirred at 45–55° C. (18 h). TLC analysis (8% MeOH/CHCl$_3$) of the reaction mixture indicated the presence of only a minor amount of product. A second lot of NaCN (50 mg, 1 mmol) was then added and the reaction was allowed to proceed at 45°–55° C. (6 h) and then at room temperature (48 h). The solvent was removed in vacuo and the residue was triturated with EtOAc (15 mL). The insoluble solid that remained was filtered and purified by flash column chromatography on SiO$_2$ gel (7% MeOH/CHCl$_3$) to give the desired product.

Yield: 0.90 g (44%).

R$_f$ 0.35 (8% MeOH/CHCl$_3$).

mp 135°–137° C.

$^1$H NMR (DMSO-d$_6$) δ 1.82 (s, 3H), 4.29 (d, J=5.9 Hz, 2H), 5.51–5.55 (m, 3H), 7.18–7.40 (m, 6H), 8.36 (br s, 1H), 8.53 (br s, 1H), 11.66 (br s, 1H).

$^{13}$C. NMR (DMSO-d$_6$) 22.59, 42.29, 61.79, 90.68, 126.67, 127.07 (2 C), 128.17 (2 C), 129.10, 139.41, 153.53, 169.19, 169.67 ppm.

IR (KBr) 3230 (br), 1620 (br), 1500 (br), 1430, 730, 690 cm$^{-1}$.

Mass spectrum, m/e (relative intensity) 288 (M$^+$+1, 64), 287 (M$^+$, 2), 230 (28), 229 (100), 153 (46).

Elemental analysis Calculated for C$_{14}$H$_{17}$N$_5$O$_2$.0.5 H$_2$O 56.47% C; 6.12% H; 23.63% N. Found 56.63% C; 5.79% H; 23.43% N.

Preparation of Functionalized α-Heteroatom Substituted Amino Acids.

General Procedure.

A BBr$_3$ solution (1M in CH$_2$Cl$_2$, 1.1 equiv) was added to n solution of 2-acetamido-N-benzyl-2-ethoxyacetamido (1 equiv) in CH$_2$Cl$_2$ (10 mmol/125 mL). The mixture was stirred at room temperature (5 h) and then concentrated to dryness in vacuo to give 2-acetamido-N-benzyl-2-bromoacetamide as in pale yellow crystalline material. The bromo adduct was then dissolved in THF (10 mmol/250 mL), cooled (−78° C.), and then added over a 15 min interval to a cooled (−78° C.) solution of the heteroatom nucleophile in THF (1 mmol/1 mL). The reaction mixture was stirred at this temperature (30 min) and then at room temperature (90 min). The insoluble salts were filtered and the filtrate concentrated in vacuo. The residue was then purified by flash column chromatography on SiO$_2$ gel using the indicated solvent as the eluent.

Using this procedure the following examples were prepared.

EXAMPLE 54

Synthesis of 2-Acetamido-N-benzyl-2-(N,N-dimethylamino)acetamido.

By making use of 2-acetamido-N-benzyl-2-ethoxyacetamide (3.00 g, 12.0 mmol), BBr$_3$ (1M in CH$_2$Cl$_2$, 13.2 mL, 13.2 mmol), and Me₂NH (5–6 equiv) was obtained a brown residue which was purified by flash column chromatography on SiO₂ gel (2.5% MeOH/CHCl₃) to give the desired product. The product was recrystallized from ethyl acetate/hexane to give light yellow cubic crystals.

Yield: 1.20 g (40%).

$R_f$ 0.39 (5% MeOH/CHCl₃).

mp 104°–106° C.

$^1$H NMR (DMSO-d₆) δ 1.91 (s, 3H), 2.11 (s, 6H), 4.22 (dd, J=5.2, 14.7 Hz, 1H), 4.34 (dd, J=6.1, 14.7 Hz, 1H), 5.11 (d, J=8.3 Hz, 1H), 7.23–7.31 (m, 5H), 8.18 (d, J=8.3 Hz, 1H), 8.55 (br s, 1H).

$^{13}$C NMR (DMSO-d₆) 22.43, 40.33 (2 C), 42.28, 69.42, 126.73, 127.27 (2 C), 128.21(2 C), 139.49, 168.49, 170.31 ppm.

IR (KBr) 3280, 1670 (br), 1500 (br), 1460, 760, 700 cm$^{-1}$.

Mass spectrum 250 (M$^+$+1).

Elemental analysis Calculated for C₁₃H₁₉N₃O₂ 62.63% C; 7.68% H; 16.85% N. Found 62.82% C; 7.66% H; 16.69% N.

EXAMPLE 55

Synthesis of 2-Acetamido-N-benzyl-2-(N-hydroxyamino) acetamide.

Using 2-acetamido-N-benzyl-2-ethoxyacetamide (2.00 g, 8.0 mmol), BBr₃ (1M in CH₂Cl₂, 8.8 mL, 8.8 mmol), and anhydrous NH₂OH (5–6 equiv) gave an oily residue. The residue was separated into three components by flash chromatography on SiO₂ gel (7.5% MeOH/CHCl₃).

2-Acetamido-N-benzyl-2-(N-hydroxyamino)acetamide.

Yield: 0.14 g (7%).

$R_f$ 0.30 (8% MeOH/CHCl₃).

mp 144°–146° C. (dec.) (recrystallized from EtOH)

$^1$H NMR (DMSO-d₆) δ 1.88 (s, 3H), 4.31 (d, J=5.7 Hz, 2H), 5.08 (dd, J=4.4, 8.1 Hz, 1H), 5.94 (dd, J=2.8, 4.4 Hz, 1H), 7.19–7.35 (m, 5H), 7.5 (d, J=2.8 Hz, 1H), 8.26 (d, J=8.1 Hz, 1H), 8.42 (t, J=5.7 Hz, 1H).

$^{13}$C NMR (DMSO-d₆) 22.69, 42.25, 67.86, 126.69, 127.14 (2 C), 128.18 (2 C), 139.08, 168.53, 169.67 ppm.

IR (KBr) 3320 (br), 1660 (br), 1540 (br), 1460, 750, 700 cm$^{-1}$.

Mass spectrum (FD) 238 (M$^+$+1).

Elemental analysis Calculated for C₁₁H₁₅N₃O₃ 55.69% C; 6.37% H; 17.71% N. Found 55.86% C; 6.37% H; 17.38% N.

Dimer A.

Yield: 0.05 g (3%).

$R_f$ 0.27 (8% MeOH/CHCl₃).

mp 177°–179° C. (recrystallized from EtOH).

$^1$H NMR (DMSO-d₆) δ 1.82 (s, 6H), 4.25–4.34 (m, 4H), 5.21 (d, J=9.3 Hz, 2H) 7.20–73.3 (m, 10H), 8.16 (d, J=9.3 Hz, 2H), 8.26 (t, J=5.8 Hz, 2H), 8.51 (s, 1H).

$^{13}$C NMR (DMSO-d₆) 22.54 (2 C), 42.30 (2 C), 67.55 (2 C), 126.63 (2 C), 127.13 (4 C), 128.11 (4 C), 139.02 (2 C), 168.24 (2 C), 169.33 (2 C) ppm.

IR (KBr) 3240 (br), 1640 (br), 1510 (br), 1450, 690 cm$^{-1}$.

Mass spectrum (FD) 442 (M$^+$+1).

Elemental analysis Calculated for C₂₂H₂₇N₅O₅ 59.85% C; 6.16% H; 15.86% N. Found 59.56% C; 6.08% H; 15.64% N.

Dimer B.

Yield: 0.10 g (6%).

$R_f$ 0.18 (8% MeOH/CHCl₃).

mp 184°–186° C. (recrystallized from MeOH).

$^1$H NMR (DMSO-d₆) δ 1.87 (6H), 4.20 (dd, J=5.3, 15.3 Hz, 2H), 4.44 (dd, J=6.2, 15.3 Hz, 2H), 5.28 (d, J=9.0 Hz, 2H), 7.15–7.31 (m, 10H), 8.00 (d, J=9.0 Hz, 2H), 8.39 (dd, J=5.3, 6.2 Hz, 2H), 8.51 (s, 1H).

$^{13}$C NMR (DMSO-d₆) 22.50 (2 C), 42.58 (2 C), 69.98 (2 C), 126.73 (2 C), 127.23 (4 C), 128.22 (4 C), 139.08 (2 C), 167.60 (2 C), 169.57 (2 C) ppm.

IR (KBr) 3300 (br), 1660 (br), 1530 (br), 1450, 740, 700 cm$^{-1}$.

Mass spectrum (FD) 442 (M$^+$+1).

Elemental analysis Calculated for C₂₂H₂₇N₅O₅ 59.85% C; 6.16% H; 15.86% N. Found 60.09% C; 5.93% H; 15.76% N.

EXAMPLE 56

Improved Synthesis of 2-Acetamido-N-benzyl-2-(N-hydroxyamino)acetamide.

2-Acetamido-N-benzyl-2-bromoacetamide (prepared from 2-acetamido-N-benzyl-2-ethoxyacetamide (3.00 g, 12.0 mmol) and BBr₃ (1M in CH₃Cl₂, 17.2 mL, 17.2 mmol)) was dissolved in THF (250 mL), cooled (−10° C.), and then added dropwise (30 min) to a suspension of NH₂OH (5–6 equiv) in THF (50 mL) at −10° C. The reaction mixture was stirred (30 min) at this temperature and then allowed to warm to room temperature (1 h). The insoluble materials were filtered and the filtrate was concentrated in vacuo. The residue was separated into two components by flash column chromatography on SiO₂ gel (7.5% MeOH/CHCl₃).

2-Acetamido-N-benzyl-2-(N-hydroxyamino)acetamide.

Yield: 0.66 g (23%).

mp 144°–146° C. (dec.) (recrystallized from EtOH).

Dimer B.

Yield: 0.10 g (5%).

mp 184°–186° C. (recrystallized from MeOH).

Dimer A was not observed under these conditions.

EXAMPLE 57

Synthesis of 2-Acetamido-N-benzyl-2-(N²-phenylhydrazino)acetamide.

Using 2-acetamido-N-benzyl-2-ethoxyacetamide (2.00 g, 8.0 mmol), BBr₃ (1M in CH₂Cl₂, 10.0 mL, 10.0 mmol), and phenylhydrazine (2.60 g, 24.0 mmol) gave a pale yellow oily residue which was purified by flash column chromatography on SiO₂ gel (2% MeOH/CHCl₃) to give the desired product. The product was recrystallized from chloroform/hexane as a light yellow solid.

Yield: 0.75 g (29%).

$R_f$ 0.26 (2% MeOH/CHCl₃).

mp 132°–134° C.

$^1$H NMR (DMSO-d₆) δ 1.89 (s, 3H), 4.28 (d, J=5.8 Hz, 2H), 4.89 (d, J=5.2 Hz, 1H), 5.09 (dd, J=5.2, 7.4 Hz, 1H), 6.61 (t, J=7.4 Hz, 1H), 6.70–7.28 (m, 10H), 8.29 (d, J=7.4 Hz, 1H), 8.60 (t, J=5.8 Hz, 1H).

$^{13}$C NMR (DMSO-d₆) 22.88, 42.22, 66.22, 112.66 (2 C), 117.57, 126.65, 127.08 (2 C), 128.15 (2 C), 128.53 (2 C), 139.12, 149.90, 168.66, 170.04 ppm.

IR (KBr) 3300, 1640 (br), 1610, 1520 (br), 1460, 760, 700 cm$^{-1}$.

Mass spectra (FD) 313 (M$^+$+1).

Elemental analysis Calculated for $C_{17}H_{20}N_4O_2$ 65.37% C; 6.45% H; 17.94% N. Found 65.15% C; 6.25% H; 17.71% N.

EXAMPLE 58

Synthesis of 2-Acetamido-N-benzyl-2-($N^2$-benzyloxycarbonylhydrazino)acetamide.

Employing 2-acetamido-N-benzyl-2-ethoxyacetamide (3.00 g, 12.0 mmol), $BBr_3$ (1M in $CH_2Cl_2$, 15.0 mL, 15.0 mmol), and benzyl carbazate (4.58 g, 27.6 mmol), 0.95 g (21%) of the desired product was obtained. The product was recrystallized from chloroform/hexane to give a white amorphous solid.

$R_f$ 0.32 (2% MeOH/CHCl$_3$).

mp 152°–154° C.

$^1$H NMR (DMSO-d$_6$) δ 1.85 (s, 3H), 4.27 (d, J=4.4 Hz, 2H), 5.00 (s, 2H), 5.14 (dd,J=3.1, 8.0 Hz, 1H), 5.23 (t, J=3.1 Hz, 1H), 7.25–7.35 (m, 10H), 8.26 (d, J=8.0 Hz, 1H), 8.56 (br s, 1H), 8.66 (br s, 1H).

$^{13}$C NMR (DMSO-d$_6$) 22.71, 42.23, 65.56, 65.97, 126.69, 127.16 (2 C), 127.61 (2 C), 127.77, 128.13 (2 C), 128.27 (2 C), 136.74, 138.87, 168.04, 169.95 ppm.

IR (KBr) 3325, 1620 (br), 1500 (br), 1440, 740, 680 cm$^{-1}$.

Mass spectrum (FD) 371 (M$^+$+1).

Elemental analysis Calculated for $C_{19}H_{22}N_4O_4$ 61.61% C; 5.99% H; 15.13% N. Found 61.40% C; 6.21% H; 15.39% N.

EXAMPLE 59

Synthesis of 2-Acetamido-N-benzyl-2-phenoxyacetamide.

Using 2-acetamido-N-benzyl-2-ethoxyacetamide (3.00 g, 12.0 mmol), $BBr_3$ (1M in $CH_2Cl_2$, 15.0 mL, 15.0 mmol), and NaOPh (4.18 g, 30 mmol) gave a brown oily residue which was purified by flash column chromatography on $SiO_2$ gel using first CHCl$_3$ and then 2% MeOH/CHCl$_3$ as the eluents to give the desired product. The compound was recrystallized from chloroform/hexane.

Yield: 0.80 g (22%).

$R_f$ 0.58 (3% MeOH/CHCl$_3$).

mp 125°–128° C. (softens at 122° C.).

$^1$H NMR (DMSO-d$_6$) δ 1.83 (s, 3H), 4.35 (d, J=5.7 Hz, 2H), 6.18 (d, J=9.4 Hz, 1H), 6.94–6.99 (m, 2H), 7.02–7.33 (m, 8H), 8.98 (t, J=5.7 Hz, 1H), 9.10 (d, J=9.4 Hz, 1H).

$^{13}$C NMR (DMSO-d$_6$) 22.54, 42.24, 76.44, 116.09 (2 C), 121.78, 126.84, 127.26 (2 C), 128.25 (2 C), 128.44 (2 C), 138.84, 155.97, 166.63, 170.73 ppm.

IR (KBr) 3300, 1650 (br), 1600, 1530 (br), 1490, 1450, 760, 700 cm$^{-1}$.

Mass spectrum (FD) 299 (M$^+$+1).

Elemental analysis Calculated for $C_{17}H_{18}N_2O_3 \cdot 0.5 H_2O$ 66.43% C; 6.23% H; 9.11% N. Found 66.62% C; 6.23% H; 9.16% N.

EXAMPLE 60

Synthesis of 2-Acetamido-N-benzyl-2-(methylmercapto)acetamide.

A cooled (–78° C.) solution or Et$_3$N (4.85 g, 48.0 mmol) in THF (20 mL) was added to a cooled (–78° C.) solution of 2-acetamido-N-benzyl-2-bromoacetamide (prepared from 2-acetamido-N-benzyl-2-ethoxyacetamide (4.00 g, 16.0 mmol) and $BBr_3$ (1M in $CH_2Cl_2$, 20.0 mL, 20.0 mmol)) in THF (275 mL). A cooled (–78° C.) solution of excess MeSH (5–6 equiv) in THF (55 mL) was then added. The reaction mixture was stirred at this temperature (30 min) and then at room temperature (1 h). The insoluble materials were filtered and the filtrate was evaporated to dryness in vacuo. The oily residue obtained was purified by flash column chromatography on $SiO_2$ gel (2% MeOH/CHCl$_3$) to give 1.10 g (27%) of the desired product as a yellow orange oil. The product was purified by a second flash column chromatography on $SiO_2$ gel (2% MeOH/CHCl$_3$) to give 0.72 g of the pure product as a white solid.

$R_f$ 0.65 (3% MeOH/CHCl$_3$).

mp 155°–157° C.

$^1$H NMR (CD$_3$NO$_2$) δ 1.98 (s, 3H), 2.08 (s, 3H), 4.39 (dd, J=6.1, 15.2 Hz, 1H), 4.49 (dd, J=6.1, 15.2 Hz, 1H), 5.51 (d, J=7.8 Hz, 1H), 7.15 (d, J=7.8 Hz, 1H), 7.17–7.41 (m, 6H).

$^{13}$C NMR (CD$_3$NO$_2$) 12.28, 22.94, 44.26, 56.03, 128.46, 128.60 (2 C), 129.77 (2 C), 140.17, 169.19, 171.06 ppm.

IR (KBr) 3320, 1650 (br), 1520 (br), 1460, 750 cm$^{-1}$.

Mass spectrum (FD) 253 (M$^+$+1).

Elemental analysis Calculated for $C_{12}H_{16}N_2O_2S$ 57.12% C; 6.39% H; 11.10% N. Found 57.06% C; 6.57% H; 11.28% N.

EXAMPLE 61

Synthesis of 2-Acetamido-N-benzyl-2-(ethylmercapto)acetamide.

Using the procedure described for the synthesis of 2-acetamido-N-benzyl-2-(methylmercapto)acetamide, 2-acetamido-N-benzyl-2-ethoxyacetamide (2.00 g, 8.0 mmol) and EtSH (0.65 g, 10.4 mmol) were converted to 0.80 g (38%) of the desired product. The compound was further purified by recrystallization from chloroform/hexane to give a beige solid.

$R_f$ 0.60 (4% MeOH/CHCl$_3$).

mp 146°–148° C.

$^1$H NMR (DMSO-d$_6$) δ 1.56 (t, J=7.4 Hz, 3H), 1.88 (s, 3H), 2.49–2.67 (m, 2H), 4.23 (dd, J=5.9, 15.2 Hz, 1H), 4.32 (dd, J=5.9, 15.2 Hz, 1H), 5.55 (d, J=9.1 Hz, 1H), 7.20–7.35 (m, 5H), 8.59 (d, J=9.1 Hz, 1H), 8.75 (t, J=5.9 Hz, 1H).

$^{13}$C NMR (DMSO-d$_6$) 14.73, 22.43, 23.73, 42.10, 53.70, 126.87, 127.14 (2 C), 128.32 (2 C), 139.01, 167.89, 169.02 ppm.

IR (KBr) 3240, 1620 (br), 1510 (br), 1415, 680, 640 cm$^{-1}$.

Mass spectrum (FD) 267 (M$^+$+1).

Elemental analysis Calculated for $C_{13}H_{18}N_2O_2S \cdot 0.25 H_2O$ 57.65% C; 6.88% H; 10.34% N. Found 57.48% C; 6.84% H; 10.28% N.

Preparation of Functionalized α-Heteroatom Substituted Amino Acids.

General Procedure.

A mixture of 2-acetamido-2-(N,N,N-trimethylammonium)acetamide tetrafluoroborate (1 eqiuv), and the nitrogen nucleophile (4–5 equiv) in MeOH (1 mmol/1 mL) was stirred at 55°–60° C. (3 h). The solvent was removed in vacuo and the residue was purified by flash column chromatography on $SiO_2$ gel using the indicated solvents as the eluent.

Using this procedure the following examples were prepared.

EXAMPLE 62

Synthesis of 2-Acetamido-N-benzyl-2-(N-methoxyamino)acetamide.

Using a MeOH solution of MeONH$_2$ (prepared from MeONH$_2$.HCl (2.83 g, 33.9 mmol) and NaOMe (1.41 g, 26.1 mmol)), and 2-acetamido-2-(N,N,N-trimethylammonium)acetamide tetrafluoroborate (2.70 g, 7.67 mmol) gave an oily residue which was purified by flash column chromatography on SiO$_2$ gel (2% MeOH/CHCl$_3$) to give the desired product. The product was recrystallized from chloroform/hexane.

Yield: 0.80 g (42%).

R$_f$ 0.23 (2% MeOH/CHCl$_3$)

mp 95°–97° C.

$^1$H NMR (DMSO-d$_6$) δ 1.88 (s, 3H), 3.38 (s, 3H), 4.22–4.41 (m, 2H), 5.18 (dd, J=4.9, 7.8 Hz, 1H), 6.78 (d, J=4.9 Hz, 1H), 7.21–7.32 (m, 5H), 8.33 (d, J=7.8 Hz, 1H), 8.56 (br s, 1H).

$^{13}$C NMR (DMSO-d$_6$) 22.64, 42.28, 61.42, 66.25, 126.74, 127.19 (2 C), 128.19 (2 C), 139.11, 167.95, 169.66 ppm.

IR (KBr) 3300, 1650, 1620, 1510 (br), 1440, 750, 680 cm$^{-1}$.

Mass spectrum (FD) 252 (M$^+$+1).

Elemental analysis Calculated for C$_{12}$H$_{17}$N$_3$O$_3$ 57.63% C; 6.82% H; 16.72% N. Found 57.06% C; 6.63% H; 16.65% N.

EXAMPLE 63

Synthesis of 2-Acetamido-N-benzyl-2-(N-(N-methylhydroxyamino))acetamide.

An MeOH solution (30 mL) of MeNHOH (21.74 mmol) (prepared from MeNHOH.HCl (2.36 g, 28.26 mmol) and NaOMe (1.17 g, 21.74 mmol)) and 2-acetamido-2-(N,N,N-trimethylammonium)acetamide tetrafluoroborate (2.20 g, 6.25 mmol) gave a residue which was purified by flash column chromatography on SiO$_2$ gel (6% MeOH/CHCl$_3$) to give the desired product as a white solid. The product was then purified by recrystallization from EtOH.

Yield: 0.95 g (61%).

R$_f$ 0.32 (8% MeOH/CHCl$_3$).

mp 159°–161° C.

$^1$H NMR (DMSO-d$_6$) δ 1.95 (s, 3H), 2.43 (s, 3H), 4.26 (dd, J=5.7, 15.1 Hz, 1H), 4.35 (dd, J=5.7, 1.51 Hz, 1H), 5.09 (d, J=9.1 Hz, 1H), 7.21–7.29 (m, 5H), 8.05 (s, 1H), 8.18 (d, J=9.1 Hz, 1H), 8.23 (t, J=5.7 Hz, 1H).

$^{13}$C NMR (DMSO-d$_6$) 22.40, 42.34, 43.92, 71.49, 126.62, 127.12 (2 C), 128.12 (2 C), 139.14, 167.82, 170.28 ppm.

IR (KBr) 3440 (br), 3300, 1640, 1530, 1460, 750, 700 cm$^{-1}$.

Mass spectrum (FD) 252 (M$^+$+1).

Elemental analysis Calculated for C$_{12}$H$_{17}$N$_3$O$_3$ 57.36% C; 6.82% H; 16.72% N. Found 57.65% C; 6.59% H; 16.66% N.

EXAMPLE 64

Synthesis of 2-Acetamido-N-benzyl-2-(N-(N,O-methylhydroxyamino))acetamide.

An MeOH solution (20 mL) of MeNHOMe (17.39 mmol) (prepared from MeNHOMe.HCl (2.20 g, 23.02 mmol) and NaOMe (0.94 g, 17.39 mmol)) and 2-acetamido-2-(N,N,N-trimethylammonium)acetamide tetrafluoroborate (2.10 g, 5.97 mmol) gave a solid residue. Flash column chromatography of the solid on SiO$_2$ gel (2% MeOH/CHCl$_3$) yielded pure desired product. The product was recrystallized from EtOH.

Yield: 1.30 g (82%).

R$_f$ 0.39 (2% MeOH/CHCl$_3$).

mp 165°–167° C.

$^1$H NMR (DMSO-d$_6$) δ 1.93 (s, 3H), 2.43 (s, 3H), 3.32 (s, 3H), 4.25 (dd, J=5.9, 149 Hz, 1H), 4.37 (dd, J=5.9, 14.9 Hz, 1H), 5.19 (d, J=9.4 Hz, 1H), 7.21–7.35 (m, 5H), 8.31 (d, J=9.4 Hz, 1H), 8.56 (t, J=5.9 Hz, 1H).

$^{13}$C NMR (DMSO-d$_6$) 22.36, 39.68, 42.34, 59.16, 70.33, 126.74, 127.41 (2 C), 128.21 (2 C), 139.30, 167.38, 170.30 ppm.

IR (KBr) 3300, 1640 (br), 1540 (br), 1460, 750, 700 cm$^{-1}$.

Mass spectrum (FD) 266 (M$^+$+1).

Elemental analysis Calculated for C$_{13}$H$_{19}$N$_3$O$_3$ 58.85% C; 7.22% H; 15.84% N. Found 59.05% C; 7.37% H; 15.75% N.

EXAMPLE 65

Synthesis of 2-Acetamido-N-benzyl-2-(N-isoxazolidino) acetamide.

Using 2-acetamido-2-(N,N,N-trimethylammonium) acetamide tetrafluoroborate (1.60 g, 4.55 mmol), isoxazolidine (prepared from isoxazolidine hydrobromide (2.41 g, 15.65 mmol) and NaOMe (0.70 g, 13.04 mmol)) gave the desired product. The product was recrystallized from chloroform/hexane to give a white amorphous solid.

Yield: 0.80 g (64%).

R$_f$ 0.29 (4% MeOH/CHCl$_3$).

mp 149°–151° C.

$^1$H NMR (DMSO-d$_6$) δ 1.91 (s, 3H), 2.05–2.20 (m, 2H), 2.45–2.89 (m, 1H), 2.98–3.07 (m, 1H), 3.74–3.90 (m, 2H), 4.25 (dd, J=6.1, 15.3 Hz, 1H), 4.35 (dd, J=6.1, 15.3 Hz, 1H), 5.23 (d, J=9.2 Hz, 1H), 7.15–7.35 (m, 5H), 8.49 (d, J=9.2 Hz, 1H), 8.56 (br s, 1H).

$^{13}$C NMR (DMSO-d$_6$) 22.26, 28.26, 42.15, 48.94, 66.19, 68.77, 126.64, 127.02 (2 C), 128.13 (2 C), 139.22, 167.43, 170.27 ppm.

IR (KBr) 3400 (br), 3300, 1650, 1530, 1470, 740, 700, 610 cm$^{-1}$.

Mass Spectrum (FD) 278 (M$^+$+1).

Elemental analysis Calculated for C$_{14}$H$_{19}$N$_3$O$_3$ 60.64% C; 6.91% H; 15.15% N. Found 60.16% C; 7.04% H; 15.07% N.

Preparation of Functionalized α-Heteroatom Substituted Amino Acids.

General Procedure.

2-Acetamido-N-benzyl-2-ethoxyacetamide (1 equiv) was suspended in Et$_2$O (100 mL/100 mmol), and then BF$_3$.Et$_2$O (1.6–2.4 equiv) was rapidly added and the resulting solution was stirred (10 min). The nucleophile (H$_2$O or EtSH) (1.6–4.0 equiv) was then added and the reaction was stirred at room temperature (18–48 h). The reaction was then quenched by the addition of an aqueous NaHCO$_3$ (100 mL/10 mmol)/ice mixture. The experimental workup varied slightly for each compound and is described in the following examples along with the observed spectral properties.

EXAMPLE 66

Synthesis of 2-Acetamido-N-benzyl-2-hydroxyacetamide.

Reacting 2-acetamido-N-benzyl-2-ethoxyacetamide (1.00 g, 4.0 mmol), BF$_3$.Et$_2$O (0.91 g, 6.4 mmol) and H$_2$O (0.12 g, 6.7 mmol) followed by aqueous NaHCO$_3$ workup gave an aqueous reaction mixture. The solution was then extracted with EtOAc (3×50 mL), and the combined EtOAc extracts were dried (Na$_2$SO$_4$), and concentrated in vacuo. The residue was purified by flash column chromatography on $SiO_2$ gel (3% MeOH/$CHCl_3$) to give the desired product as a white solid.

Yield: 0.30 g (34%).

$R_f$ 0.14 (3% MeOH/$CHCl_3$).

mp 136°–138° C.

$^1$H NMR (DMSO-$d_6$) δ 1.85 (s, 3H), 4.29 (d, J=5.9 Hz, 2H), 5.48 (dd, J=5.5, 8.6 Hz, 1H), 6.47 (d, J=5.5 Hz, 1H), 7.21–7.35 (m, 5H), 8.52 (t, J=5.9 Hz, 1H), 8.59 (d, J=8.6 Hz, 1H).

$^{13}$C NMR (DMSO-$d_6$) 22.66, 41.99, 71.42, 126.66, 127.22 (2 C), 128.13 (2 C), 139.20, 169.47, 169.62 ppm.

IR (KBr) 3300, 1620, 1530 (br), 1430 (br), 730, 690 $cm^{-1}$.

Mass spectrum, m/e (relative intensity) 223 ($M^+$+1, 1), 163 (11), 134 (9), 106 (46), 91 (100), 77 (22), 65 (38).

Elemental analysis Calculated for $C_{11}H_{14}N_2O_3$ 59.45% C; 6.35% H; 12.61% N. Found 59.24% C; 6.36% H; 12.50% N.

EXAMPLE 67

Synthesis of 2-Acetamido-N-benzyl-2-(ethylmercapto) acetamido.

Using 2-acetamido-N-benzyl-2-ethoxyacetamide (2.00 g, 8.0 mmol), $BF_3$·$Et_2O$ (2.72 g, 19.2 mmol) and EtSH (2.38 g, 38.4 mmol) gave an aqueous reaction mixture. The solution was extracted with $CHCl_3$ (3×100 mL). The combined $CHCl_3$ layers were dried ($Na_2SO_4$), and then concentrated in vacuo to give the desired product as white solid.

Yield: 1.90 g (89%).

$R_f$ 0.60 (4% MeOH/$CHCl_3$).

mp 148°–149° C. (mixed melting point with an authentic sample, of Example 61 was undepressed).

EXAMPLE 68

Synthesis of 2,2-Dicacetamido-N-benzylacetamide.

$Ac_2O$ (1 mL) was added to a solution of 2-acetamido-N-benzyl-2-aminoacetamide (1.10 g, 4.98 mmol) in dry pyridine (10 mL) and then $CH_2Cl_2$ (20 mL) was added. The mixture was stirred at room temperature (4 h) and then the volatile materials were removed in vacuo. The residue was then treated with a saturated aqueous $NaHCO_3$ solution (50 mL). The white solid that remained was the desired product and was filtered, dried ($Na_2SO_4$), and recrystallized from MeOH.

Yield: 1.20 g (92%).

mp 265°–267° C. (dec.).

$^1$H NMR (DMSO-$d_6$) δ 1.84 (s, 6H), 4.26 (d, J=5.8 Hz, 2H), 5.71 (t, J=7.6 Hz, 1H), 7.20–7.31 (m, 5H), 8.44 (d, J=7.6 Hz, 2H), 8.48 (t, J=5.8 Hz, 1H).

$^{13}$C (DMSO-$d_6$) 22.44 (2 C), 42.26, 56.99, 126.62, 127.02 (2 C), 128.12 (2 C), 139.15, 168.19, 169.39 (2 C) ppm.

IR (KBr) 3260, 1530, 1500, 740, 690 $cm^{-1}$.

Mass spectrum (FD) 264 ($M^+$+1).

Elemental analysis Calculated for $C_{13}H_{17}N_3O_3$ 59.30% C; 6.51% H; 15.96% N. 59.16% C; 6.49% H; 15.86% N.

EXAMPLE 69

Synthesis of 2-Acetamido-N-benzyl-2-trifluoroacetamidoacetamide.

Ice cold trifluoroacetic anhydride (8 mL) was added in one portion to ice cold 2-acetamido-N-benzyl-2-aminoacetamide (1.00 g, 4.53 mmol). The reaction was accompanied by the evolution of heat. After stirring (5 min), the volatile materials were removed in vacuo. The residue was treated with a saturated aqueous $NaHCO_3$ solution (20 mL), and the solid that remained was filtered and washed with $H_2O$ to give the desired product. The product was recrystallized from EtOH.

Yield: 1.00 g (70%).

$R_f$ 0.34 (8% MeOH/$CHCl_3$).

mp 228°–230° C.

$^1$H NMR (DMSO-$d_6$) δ 1.90 (s, 3H), 4.30 (d, J=5.1 Hz, 2H), 5.85 (d, J=8.0 Hz, 1H), 7.21–7.35 (m, 5H), 8.64 (d, J=8.0 Hz, 1H), 8.75 (t, J=5.1 Hz, 1H), 10.04 (s, 1H).

$^{13}$C NMR(DMSO-$d_6$) 22.52, 42.52, 57.42, 117.4 (q, JCF= 288.3 Hz), 126.80, 127.16 (2 C), 128.21 (2 C), 138.93, 156.14 (q, JCF=35.3 Hz), 166.3.9, 169.88 ppm.

IR (KBr) 3300, 1720, 1660, 1520, 1380, 760, 700 $cm^{-1}$.

Mass spectrum (FD) 318 ($M^+$+1).

Elemental analysis Calculated for $C_{13}H_{14}N_3O_3F_3$ 49.21% C; 4.45% H; 13.24% N. Found 49.48% C; 4.43% H; 13.10% N.

EXAMPLE 70

Synthesis of 2-Acetamido-N-benzyl-2-(N,N,N-trimethylammonium)acetamide Tetrafluoroborate.

A solution of 2-acetamido-N-benzyl-2-(N,N-dimethylamino)acetamide (1.93 g, 7.76 mmol) in nitromethane (7 mL) was added slowly to an ice cold solution of trimethyloxonium tetrafluoroborate (1.26 g, 8.54 mmol) in nitromethane (6 mL). The reaction mixture was stirred at this temperature (15 min) and then at room temperature (2 h). Anhydrous $Et_2O$ (~50 mL) was added the reaction mixture and the white solid that separated was filtered, washed with $Et_2O$, and dried in vacuo.

Yield: 1.95 g (72%).

mp 171°–173° C. (dec.).

$^1$H NMR (CD$_3$NO$_2$) δ 2.14 (s, 3H), 3.18 (s, 9H), 4.50 (d, J=5.8 Hz, 2H), 5.70 (d, J=9.3 Hz, 1H), 7.30–7.41 (m, 5H), 7.57 (d, J=9.3 Hz, 1H), 7.70 (br s, 1H).

IR (KBr) 3300, 1680 (br), 1530, 1490, 710 $cm^{-1}$.

Mass spectrum (FD) 264 ($M^+$).

Elemental analysis Calculated for $C_{14}H_{22}N_3O_2BF_4$ 47.89% C; 6.31% H; 11.97% N. Found 47.80% C; 6.33% H; 12.00% N.

EXAMPLE 71

Synthesis of 2-Acetamido-N-benzyl-2-(ethylmercapto) acetamide-S-oxide.

A solution of m-chloroperbenzoic acid (1.00 g (~65%), 3.76 mmol) in $CH_2Cl_2$ (10 mL) was added dropwise into a stirred, cooled (−10° to −15° C.) $CH_2Cl_2$ solution (125 mL) of 2-acetamido-N-benzyl-2-(ethylmercapto)acetamide (1.00 g, 3.76 mmol) under $N_2$. The reaction was stirred (30 min) at this temperature and then, the m-chlorobenzoic acid was precipitated as its ammonium salt by passing $NH_3$ gas over the surface of the reaction solution. The excess $NH_3$ was removed by passing $N_2$ gas through the solution (20 min) at room temperature. The ammonium salt was filtered, and the filtrate was concentrated in vacuo. The residue was purified by flash chromatography on $SiO_2$ gel (2% MeOH/$CHCl_3$) to give the desired product. The product was recrystallized from chloroform/hexane as a white granular solid.

Yield: 0.55 g (52%).

$R_f$ 0.23 (2% MeOH/$CHCl_3$).

mp 135°–137° C.

$^1$H NMR (DMSO-d$_6$) δ 1.15 (t, J=7.5 Hz, 3H), 1.99 (s, 3H), 2.49–2.56 (m, 1H), 2.65–2.72 (m, 1H), 4.34 (d, J=5.7 Hz, 2H), 5.55 (d, J=9.5 Hz, 1H), 7.23–7.34 (m, 5H), 8.74 (d, J=9.5 Hz, 1H), 8.77 (t, J=5.7 Hz, 1H).

$^{13}$C NMR (DMSO-d$_6$) 7.03, 22.34, 42.40, 42.47, 67.15, 126.89, 127.27 (2 C), 128.24 (2 C), 138.55, 164.66, 170.18 ppm.

IR (KBr) 3300 (br), 1640 (br), 1510 (br), 1370, 1230, 1100, 1020, 900 cm$^{-1}$.

Mass spectrum (FD) 283 (M$^+$+1).

Elemental analysis Calculated for C$_{13}$H$_{18}$N$_2$O$_3$S 55.30% C; 6.43% H; 9.92% N. Found 55.17% C; 6.38% H; 9.70% N.

EXAMPLE 72

Synthesis of 2-Acetamido-N-benzyl-2-(S-ethylmercapto) acetamide-S-oxide.

A solution of NaIO$_4$ (1.77 g, 8.27 mmol) in H$_2$O (20 mL) was added dropwise into a stirred solution of 2-acetamido-N-benzyl-2-(ethylmercapto)acetamide (2.00 g, 7.52 mmol) in MeOH (25 mL). A precipitate appeared rapidly. H$_2$O (~30 mL) was added to the mixture to dissolve most of the suspension, and the reaction was stirred (4 h) at room temperature. The reaction was concentrated in vacuo and the remaining aqueous mixture was extracted with CHCl$_3$ (3×100 mL). The combined CHCl$_3$ extracts were dried (Na$_2$SO$_4$) and the solvent was removed in vacuo. The oily residue (1.95 g, 92%) solidified on drying in vacuo. NMR analysis (DMSO-d$_6$) or the product showed that it was a 2:1 mixture of the two diastereomers of the desired product. The reaction was recrystallized from EtOAc to give nearly pure diastereomer A (1.20 g) that was obtained from the m-chloroperbenzoic acid reaction. The EtOAc mother liquor was concentrated and the remaining residue (0.75 g) was recrystallized from ethyl acetate/hexane to give a diastereomeric mixture (0.41 g) of the two diastereomers A and B in a 2:3 ratio, respectively.

R$_f$ 0.60 (4% MeOH/CHCl$_3$).

mp 135°–137° C. (softens at 117° C.).

IR (KBr) 3300 (br), 1640 (br), 1510 (br), 1370, 1230, 1100, 1020, 900 cm$^{-1}$.

Mass spectrum (FD) 283 (M$^+$+1).

Elemental analysis: Calculated for C$_{13}$H$_{18}$N$_2$O$_3$S: 55.30% C; 6.43% H; 9.92% N. Found: 55.58% C; 6.49% H; 9.97% N.

The following NMR spectral properties have been assigned to compounds A and B.

Diastereomer A.

$^1$H NMR (DMSO-d$_6$) δ 1.16 (t, J=7.5 Hz, 3H), 2.00 (s, 3H), 2.49–2.72 (m, 2H), 4.28–4.39 (m, 2H), 5.56 (d, J=9.7 Hz, 1H), 7.21–7.34 (m, 5H), 8.71–8.77 (m, 2H).

$^{13}$C NMR (DMSO-d$_6$) 7.10, 22.43, 42.48, 42.57, 67.23, 126.98, 127.36 (2 C), 128.33 (2 C), 138.63, 164.73, 170.25 ppm.

Diastereomer B.

$^1$H NMR (DMSO-d$_6$) δ 1.13 (t, J=7.6 Hz, 3H), 1.94 (s, 3H), 2.49–2.72 (m, 2H), 4.28–4.39 (m, 2H), 5.71 (d, J=9.9 Hz, 1H), 7.21–7.34 (m, 5H), 8.83 (d, J=9.9 Hz, 1H), 8.98 (t, J=5.6 Hz, 1H).

$^{13}$C NMR (DMSO-d$_6$) 6.47, 22.43, 41.53, 42.55, 67.90, 126.98, 127.36 (2 C), 128.33 (2 C), 138.39, 164.43, 169.82 ppm.

EXAMPLE 73

Synthesis of 2-Acetamido-N-benzyl-2-(ethanesulfonyl) acetamide.

An aqueous solution (20 mL) of NaIO$_4$ (3.00 g, 14.02 mmol) was added to a MeOH solution (20 mL) of 2-acetamido-N-benzyl-2-(ethylmercapto)acetamide (0.95 g, 3.57 mmol). The initial homogeneous solution rapidly became turbid. H$_2$O (~10 mL) was then added dropwise until the system became homogeneous. The solution was stirred (18 h) at 50°–60° C. MeOH (50 mL) was added to the reaction solution and the precipitated salt was filtered and washed with MeOH (10 mL). The filtrate was concentrated and the remaining solution was extracted with CHCl$_3$ (3×50 mL). The combined CHCl$_3$ extracts were dried (Na$_2$SO$_4$), and concentrated in vacuo. Time residue was purified by flash chromatography on SiO$_2$ gel (1% MeOH/CHCl$_3$) to give the desired product. The product was further purified by recrystallization from EtOH:.

Yield: 0.34 g (32%).

R$_f$ 0.34 (3% MeOH/CHCl$_3$).

mp 161°–163° C.

$^1$H NMR (DMSO-d$_6$) δ 1.22 (t, J=7.4 Hz, 3H), 1.99 (s, 3H), 3.04–3.24 (m, 2H), 4.31 (dd, J=5.7, 15.3 Hz, 1H), 4.41 (dd, J=5.7, 15.3 Hz, 1H), 5.93 (d, J=9.8 Hz, 1H), 7.22–7.35 (m, 5H), 9.13 (t, J=5.7 Hz, 1H), 9.17 (d, J=9.8 Hz, 1H).

$^{13}$C NMR (DMSO-d$_6$) 5.72, 22.27, 42.63, 45.43, 69.14, 127.02, 127.28 (2 C), 128.33 (2 C), 138.16, 161.88, 169.83 ppm.

IR (KBr) 3300, 2940, 1660, 1520, 1310, 1230, 1120, 900 cm$^{-1}$.

Mass spectrum (FD) 298 (M$^+$).

Elemental analysis Calculated for C$_{13}$H$_{18}$N$_2$O$_4$S 52.33% C; 6.08% H; 9.39% N. Found 52.52% C; 6.06% H; 9.53% N.

EXAMPLE 74

Synthesis of 2-Acetamido-N-benzyl-2-(N,N,N-trimethylammonium)acetamide Tetrafluoroborate.

A solution or 2-acetamido-N-benzyl-2-(N,N-dimethylamino)acetamide (1.93 g, 7.76 mmol) in nitromethane (7 mL) was added slowly to an ice cold solution of trimethyloxonium tetrafluoroborate (1.26 g, 8.54 mmol) in nitromethane (6 mL). The reaction mixture was stirred at this temperature (15 min) and then at room temperature (2 h). Anhydrous Et$_2$O (~50 mL) was added to the reaction mixture and the white solid that separated was filtered, washed with Et$_2$O, and dried in vacuo.

Yield: 1.95 g (72%).

mp 171°–173° C. (dec.).

$^1$H NMR (CD$_3$NO$_2$) δ 2.14 (s, 3H), 3.18 (s, 9H), 4.50 (d, J=5.8 Hz, 2H), 5.70 (d, J=9.3 Hz, 1H), 7.30–7.41 (m, 5H), 7.57 (d, J=9.3 Hz, 1H), 7.70 (br s, 1H).

IR (KBr) 3300, 1680 (br), 1530, 1490, 710 cm$^{-1}$.

Mass spectrum (FD) 264 (M$^+$).

Elemental analysis

Calculated for C$_{14}$H$_{22}$N$_3$O$_2$BF$_4$ 47.89% C; 6.31% H; 11.97% N. Found 47.80% C; 6.33% H; 12.00% N.

EXAMPLE 75

Synthesis of 2-Acetamido-N-benzyl-2-(1-pyrrole) acetamide.

A solution 2-acetamido-N-benzyl-2-bromoacetamide (prepared from 2-acetamido-N-benzyl-2-ethoxyacetamide (2.00 g, 8.0 mmol) and BBr₃ (1M CH₂Cl₂ solution, 8.8 mL, 8.8 mmol)) was prepared in THF (225 mL) and cooled to −78° C. It was then added under N₂ gas atmosphere to a cooled (−78° C.) suspension of potassium pyrrole (2.71 g, 25.8 mmol) in THF (25 mL). The reaction mixture was stirred at −78° C. (1 h) and then at room temperature (1 h). H was then treated with water (10 mL) and acidified with 5% citric acid to pH 4.0 after which it was made basic with aqueous saturated Na₂CO₃ solution. The aqueous mixture was extracted with EtOAc (2×250 mL) and the organic layers were dried (Na₂SO₄). The volatile materials were removed in vacuo and the residue was purified by flash column chromatography on silica gel using 3% MeOH/ CHCl₃ as the eluant to give 0.4 g (18%) of the desired product. It was purified by recrystallization from EtOH: mp 182°–184° C.; $R_f$ 0.44 (4% MeOH/CHCl₃); ¹H NMR (DMSO-d₆) δ 1.91 (s, COCH₃), 4.30 (d, J=5.5 Hz, CH₂), 6.01 (s, 2×C₃H), 6.38 (d, J=8.7 Hz, CH), 6.85 (s, 2×C₂H), 7.11–7.35 (m, 5PhH), 8.96 (t, J=5.5 Hz, NH), 9.14 (d, J=8.7 Hz, NH); ¹³C NMR (DMSO-d₆) 22.22 (COCH₃), 42.15 (CH₂), 62.86 (CH), 107.79 (2C₃), 119.19 (2C₂), 126.76 (C₄'), 127.01 (2C₂' or 2C₃'), 128.11 (2C₂' or 2C₃'), 138.34 (C₁'), 166.37 (CONH), 169.41 (COCH₃) ppm; mass spectrum, m/e (relative intensity) 272 (M⁺+1, 22), 271 (M⁺, 100).

Anal. Calcd for C₁₅H₁₇N₃O₂.0.2 H₂O: C, 65.53; H, 6.37; N, 15.28. Found: C, 65.80; H, 6.22; N, 15.13.

EXAMPLE 76

Synthesis of 2-Acetamido-N-benzyl-2-(1-imidazole) acetamide.

Making use of the experimental procedure described in the above experiment, 2-acetamido-N-benzyl-2-ethoxyacetamide (2.00 g, 8.0 mmol), BBr₃ (1M CH₂Cl₂ solution, 8.8 mL, 8.8 mmol), Et₃N (1.62 g, 1.60 mmol), and imidazole (0.60 g, 8.8 mmol) gave 0.60 g (30%) of the desired product. It was recrystallized from ethyl acetate/ hexane as a beige colored solid: mp 146°–148° C.; $R_f$ 0. (7% MeOH/CHCl₃); ¹H NMR (DMSO-d₆) δ 1.85 (s, COCH₃), 4.30 (br s, CH₂), 6.53 (d, J=8.0 Hz, CH), 6.89 (s, C₅H), 7.12–7.33 (m, C₄H, 5PhH), 7.69 (s, C₂H), 9.06 (br s, NH), 9.29 (d, J=8.0 Hz, NH); ¹³C NMR (DMSO-d₆) 22.28 (COCH₃), 42.36 (CH₂), 61.18 (CH), 117.56 (C₅), 126.92 (C₄'), 127.16 (2C₂' or 2C₃'), 128.19 (C₄), 128.26 (2C₂' or 2C₃'), 136.21 (C₂), 138.27 (C₁'), 165.72 (CONH), 169.77 (COCH₃) ppm; mass spectrum, FD (relative intensity) 274 (M⁺+2, 12), 273 (M⁺+1, 77), 272 (100), 205 (34), 274 (18).

Anal. Calcd for C₁₄H₁₆N₄O₂: C, 61.75; H, 5.92; N, 20.57. Found: C, 61.95; H, 6.09; N, 20.32.

EXAMPLE 77

Synthesis of 2-Acetamido-N-benzyl-2-(1-pyrazole) acetamide.

A solution of 2-acetamido-N-benzyl-2-bromoacetamide (prepared from 2-acetamido-N-benzyl-2-ethoxyacetamide (3.60 g, 14.4 mmol) and BBr₃ (1M CH₂Cl₂ solution, 15.8 mL, 15.8 mmol)) was prepared in THF (250 mL) and cooled to −78° C. A solution of triethylamine (2.91 g, 28.8 mmol) in THF (20 mL) was then added to the above solution. This was followed by the addition of THF (30 mL) solution of pyrazole (1.17 g, 17.28 mmol) and the mixture thus obtained was stirred at −78° C. (30 min) and room temperature (1 h). The insoluble materials were filtered and the solvents removed from the filtrate in vacuo. The residue was then purified by flash column chromatography on silica gel using 4% MeOH/CHCl₃ as the eluant to give 0.80 g (22%) of the desired product. It was then recrystallized from EtOAc as a white solid: mp 158°–160° C.; $R_f$ 0.51 (6% MeOH/CHCl₃); ¹H NMR (DMSO-d₆) δ 1.93 (s, COCH₃), 4.29 (d, J=5.8 Hz, NH), 6.26 (s, C₄H), 6.57 (d, J=8.8 Hz, CH), 7.15–7.33 (m, 5PhH), 7.48 (br s, C₅H), 7.76 (br s, C₃H), 8.96 (t, J=5.8 Hz, NH), 9.23 (d, J=8.8 Hz, NH); ¹³C NMR (DMSO-d₆) 22.41 (COCH₃), 42.40 (CH₂), 65.51 (CH), 105.37 (C₄), 126.87 (C₄'), 127.14 (2C₂' or 2C₃'), 128.25 (2C₂' or 2C₃'), 129.00 (C₅), 138.59 (C₃), 139.17 (C₁'), 165.68 (CONH), 169.81 (COCH₃) ppm; mass spectrum, m/e (relative intensity) 273 (M⁺+1, 11), 272 (M⁺, 2), 139 (83), 138 (100), 92 (37).

Anal. Calcd for C₁₄H₁₆N₄O₂: C, 61.75; H, 5.92; N, 20.57. Found: C, 61.95; H, 5.96; N, 20.28.

EXAMPLE 78

Synthesis of 2-Acetamido-N-benzyl-2-(1-(1,2,4-triazole)) acetamide.

Using 2-acetamido-N-benzyl-2-ethoxyacetamide (4.00 g, 16.0 mmol), BBr₃ (1M CH₂Cl₂ solution, 17.6 mL, 17.6 mmol), Et₃N (4.85 g, 48.0 mmol), and 1,2,4-triazole (1.43 g, 20.8 mmol), 1.20 g (28%) of the desired product was obtained. It was recrystallized from EtOAc as an amorphous white solid: mp 146°–148° C.; $R_f$ 0.48 (6% MeOH/CHCl₃); ¹H NMR (DMSO-d₆) δ 1.85 (s, COCH₃), 4.32 (br s, CH₂), 6.70 (d, J=7.8 Hz, CH), 7.21–7.29 (m, 5PhH), 8.01 (s, C₃H), 8.57 (s, C₅H), 9.04 (br s, NH), 9.39 (d, J=7.8 Hz, NH); ¹³C NMR (DMSO-d₆) 22.39 (COCH₃), 42.59 (CH₂), 65.02 (CH), 126.97 (C₄'), 127.25 (2C₂' or 2C₃'), 128.32 (2C₂' or 2C₃'), 138.47 (C₁'), 143.93 (C₅), 151.50 (C₃), 164.77 (CONH), 170.23 (COCH₃) ppm; mass spectrum, FD (relative intensity) 275 (M⁺+2, 12), 274 (M⁺+1, 100), 273 (11), 205 (19), 204 (13), 140 (67), 139 (31).

Anal. Calcd for C₁₃H₁₅N₅O₂: C, 57.13; H, 5.53; N, 25.63. Found: C, 57.37; H, 5.66; N, 25.38.

EXAMPLE 79

Synthesis of 2-Acetamido-N-benzyl-2-(1-tetrazole)) acetamide.

Making use of 2-acetamido-N-benzyl-2-ethoxyacetamide (3.00 g, 12.0 mmol), BBr₃ (1M CH₂Cl₂ solution, 13.2 mL, 13.2 mmol), Et₃N (2.42 g, 24.0 mmol), and tetrazole (1.10 g, 15.6 mmol), 0.90 g (27%) of the desired product was obtained as a white solid. It was recrystallized from EtOH: mp 169°–171° C.; $R_f$ 0.22 (4% MeOH/CHCl₃); ¹H NMR (DMSO-d₆) δ 1.97 (s, COCH₃), 4.25–4.40 (m, CH₂), 7.05 (d, J=8.4 Hz, CH), 7.21–7.38 (m, 5PhH), 9.23 (t, J=5.5 Hz, NH), 9.44 (s, C₅H), 9.69 (d, J=8.4 Hz, NH); ¹³C NMR (DMSO-d₆) 22.38 (COCH₃), 42.78 (CH₂), 63.62 (CH), 127.10 (C₄'), 127.39 (2C₂' or 2C₃'), 128.38 (2C₂' or 2C₃'), 138.26 (C₁'), 143.67 (C₅), 163.88 (CONH), 170.62 (COCH₃), ppm; mass spectrum, FD (relative intensity) 275 (M⁺ 79), 273 (14), 206 (100), 205 (50).

Anal. Calcd for C₁H₁₄N₆O₂: C, 52.55; H, 5.15; N, 30.64. Found: C, 52.75; H, 5.33; N, 30.64.

EXAMPLE 80

Preparation of α-acetamido-N-benzyl-2-pyridylacetamide and 2-acetamido-N-benzyl-2-(2'-pyridone)acetamide.
Preparation of 2-acetamido-2-bromo-N-benzylacetamide.

A solution of 2-acetamido-2-ethoxy-N-benzylacetamide (2.00 g, 8 mmol) in dry CH₂Cl₂ (200 mL) was stirred at room temperature as a solution of BBr₃ (8.8 mL, 8.8 mmol, 1.0M in CH₂Cl₂) was introduced by means of a syringe under a nitrogen atmosphere. A while mist formed and alter it disappeared, the N₂ line was removed and the reaction sealed. The resulting yellow solution was stirred (3.5 h) and then concentrated in vacuo to give yellow crystals of α-acetamido-2-bromo-N-benzyl acetamido which was stored under vacuum overnight.

Preparation of 2-pyridyllithium.

The generation of 2-pyridyllithium in situ was run under nitrogen. A solution of n-butyllithium (7.2 mL, 2.5M solution in hexane, 18 mmol) was added to dry ether (60 mL), cooled to −20° C., and stirred as 2-bromopyridine (1.6 mL, 17 mmol) in dry ether (15 mL,) was added dropwise (15 min). The resulting blood red solution was stirred at −20° C. for an additional 5 minutes and then transferred through a doubled-ended needle under a stream of nitrogen to an addition funnel where it was cooled to −78° C.

Preparation of α-acetamido-N-benzyl-2-pyridylacetamide and 2-acetamido-N-benzyl-2-(2'-pyridone)acetamide.

The cooled 2-pyridyllithium solution was added dropwise (approximately 2 drops per second) to the solution of 2-acetamido-2-bromo-N-benzylacetamide in dry THF (200 mL) and maintained at −78° C. The reaction mixture was stirred for an additional 30–45 minutes at −78° C. The reaction was quenched with saturated aqueous solution of $NH_4Cl$ (40 mL) at −78° C. producing a heterogenous mixture $Na_2CO_3$ was added dropwise until the precipitate dissolved. The organic layer was separated and then the aqueous layer was extracted with ether (2×50 mL). The combined organic layers were dried ($Na_2SO_4$), concentrated under vacuum and separated using flash chromatography on silica gel with ethyl acetate as the eluent. The fractions containing the products were concentrated under vacuum, separated and then further purified by column chromatography on alumina (80–200 mesh, Grade 1, Fisher) employing ethyl acetate as the solvent. Fractions containing α-acetamido-N-benzyl-2-pyridylacetamide was concentrated to dryness and gave a white amorphous solid (250 mg, 11% yield); $R_f$=0.39 (5% $CH_3OH/CHCl_3$); mp 146°–147° C.; IR (KBr) 3290, 3180, 3020, 1620 br, 1580, 1520 br, 1480, 1420, 1370, 1310, 1260 cm$^{-1}$; $^1H$ NMR (300 MHz, DMSO-$d_6$) δ 1.96 (s, 3H), 4.28 (d, J=5.8 Hz, 2H), 5.59 (d, J=8.0 Hz, 1H), 7.18–7.30 (m, 5H), 7.32 (dd, J=7.7, 5.2 Hz, 1H), 7.47 (d, J=7.7 Hz, 1H), 7.80 (dt, J=7.7, 1.5 Hz, 1H), 8.55 (m, 2H), 8.78 (br t, J=5.8 Hz, 1H); $^{13}C$ NMR (75 MHz, DMSO-$d_6$) 22.5, 42.1, 58.3, 121.7, 122.8, 126.6, 126.9 (2C), 128.1 (2C), 136.8, 139.1, 148.6, 157.2, 169.0, 169.2 ppm; FD (Lilly) mass spectrum, m/e (relative intensity) 284 ($M^++1$, 6), 283 ($M^+$, 0.8), 151 (8), 150 (100), 141 (4). $C_{16}H_{17}N_3O_2$ Anal. Calcd for C 67.83, H, 6.05, N, 14.83
Found: C, 68.11, H, 6.00, N, 14.89.

Fractions containing 2-acetamido-N-benzyl-2-(2'-pyridone)acetamide were combined, concentrated in vacuo and yielded a white amorphous solid: (150 mg, 6% yield). $R_f$ 0.34 (5% $CH_3OH/CHCl_3$); mp 226 decomposed (recrystallized in ethanol) $^1H$ NMR (300 MHx, DMSO-$d_6$) δ 1.94 s, 4.26 (dd, J=15.2, 5.7 Hz, 1H), 4.33 (dd, J=15.2, 6.1 Hz, 1H),6.26 (br t, J=6.8 Hz, 1H), 6.37 (br d, J=9.1 Hz, 1H), 6.69 (d, J=8.7 Hz, 1H), 7.22–7.33 (m, 5H), 7.42 (ddd, J=9.1, 6.8, 1.6 Hz, 1H), 7.58 (dd, J=6.8, 1.6 Hz, 1H), 8.93 (br t, J=5.8 Hz, 1H), 9.20 (d, J=8.7 Hz, 1H); $^{13}C$ NMR (75 MHz, DMSO-$d_6$) 22.5, 42.5, 62.5, 105.1, 119.4, 126.80, 127.10 (2C), 128.2 (2C), 135.6, 138.8, 140.2, 161.2, 166.0, 170.0 ppm. Hydrogen and carbon assignments were verified with $^1H$-$^1H$ COSY, $^1H$-$^{13}C$-COSY, zero quantum NMR experiments. The structure was confirmed by X-ray crystallography.

Preparation of authentic 2-acetamido-N-benzyl-2-(2'-pyridone)acetamide.

The generation of 2-hydroxypyridylsodium in situ was done under anhydrous conditions. A solution of 2-hydroxypyridine (1.57 g, 16 mmol, vacuum dried, 97% Aldrich) in dry THF (200 mL) was stirred and cooled to 0° C. and then NaH (0.77 g, 60% in mineral oil, 19.2 mmol) was added in one portion leading to the evolution of $H_2$ and the generation of a heterogeneous mixture. A solution of 2-acetamido-2-bromo-N-benzylacetamide (8 mmol based on 2-acetamido-2-ethoxy-N-benzylacetamide) in dry THF (160 mL) was then transferred through a double-ended needle by means of a stream of nitrogen. The resulting mixture was quenched with saturated aqueous solution of $NH_4Cl$ (50 mL) at 0° C. producing a white precipitate. A saturated aqueous solution $Na_2CO_3$ was added dropwise while stirring at 0° C. until all of the white precipitate dissolved. The two layers were separated while cold and then the aqueous fraction was extracted with THF (2×100 mL). The combined organic layers were dried ($Na_2SO_4$), and concentrated to dryness. The crude reaction mixture residue was dissolved in a minimum of $CHCl_3$ and was flash chromatographed on a silica gel column using ethyl acetate as the eluent and gave a white amorphous solid (1.10 g, 46% yield) which was identical to properties previously observed for 2-acetamido-N-benzyl-2-(2'-pyridone)acetamide: $R_f$ 0.34 (5% $CH_3OH/CHCl_3$); mp 162°–163.5° C. (recrystallized in ethyl acetate); IR (KBr) 3300, 3280, 3260, 3080, 1690, 1680, 1650 br, 1580, 1570, 1520, 1490, 1140 cm$^{-1}$; $^1H$ NMR (300 MHz, DMSO-$d_6$) δ 1.96 (s, 3H), 4.27 (dd, J=15.3, 5.8 Hz, 1H), 4.36 (dd, J=15.3, 6.2 Hz, 1H), 6.27 (dr, J=6.8, 1.1 Hz, 1H), 6.39 (bd, J=8.9 Hz, 1H), 6.71 (d, J=8.7 Hz, 1H), 7.22–7.34 (m, 5H), 7.43 (ddd, J=8.9, 6.8, 1.9 Hz, 1H), 7.59 (dd, J=6.8, 1.9 Hz, 1H), 8.93 (br t, J=5.9 Hz, 1H), 9.20 (d, J=8.7 Hz, 1H); $^{13}C$ NMR (75 MHz, DMSO-$d_6$) 22.4, 42.5, 62.5, 105.1, 119.4, 126.8, 127.1 (2C), 128.2 (2C), 135.6, 138.8, 140.1, 161.1, 166.0, 169.9 ppm; FD (Lilly) mass spectrum m/e (relative intensity) 598 (2M, 2), 300 ($M^++1$, 17), 299 ($M^+$, 100), 96 (2), 95 (26). $C_{16}H_{17}N_3O_3$.

Anal. Calcd for C, 64.20, H 5.73, N 14.04.

EXAMPLE 81

α-acetamido-N-benzyl-2-pyridyl acetamide N-oxide

To a cooled solution of 2-α-acetamido-N-benzyl-2-pyridylacetamide dissolved in dry THF is added m-perchloroperbenzoic acid to give the resulting product.

Similarly, using the procedure described hereinabove, the following examples are prepared.

2-acetamido-N-benzyl-2-(3-pyridyl)acetamide and the N-oxide thereof,
2-acetamido-N-benzyl-2-(4-pyridyl)acetamide and the N-oxide thereof,
2-acetamido-N-benzyl-2-(2-pyrimidinyl)acetamide and the N-oxide thereof
2-acetamido-N-benzyl-2-(4-pyrimidinyl)acetamide and the N-oxide thereof,
2-acetamido-N-benzyl-2-(5-pyrimidinyl)acetamide and the N-oxide thereof,
2-acetamido-N-benzyl-2-(3-pyridazinyl)acetamide and the N-oxide thereof,
2-acetamido-N-benzyl-2-(4-pyridazinyl)acetamide and the N-oxide thereof,
2-acetamido-N-benzyl-2-(4-pyrazinyl)acetamide and the N-oxide thereof,
2-acetamido-N-benzyl-2-(2-thiazolyl)acetamide,
2-acetamido-N-benzyl-2-(2-oxazolyl)acetamide,
2-acetamido-N-benzyl-2-(3-isoxazolyl)acetamide,
2-acetamido-N-benzyl-2-(5-isoxatolyl)acetamide, 2-acetamido-N-benzyl-2-(3-isothiazolyl)acetamide, and
2-acetamido-N-benzyl-2-(5-isothiazolyl)acetamide.
General Procedure.

2-Acetamido-N-benzyl-2-ethoxyacetamide (1 equiv.) was suspended in anhydrous ethyl ether, and then boron trifluoride etherate (1.6–6.3 equiv.) was rapidly added and the resulting solution was stirred for 15 min. The aromatic substrate (1.6–16 equiv.) was then added and the reaction was stirred at room temperature (1–7 days).

EXAMPLE 82

α-Acetamido-N-benzyl-2-(S-thiophenoxy)-acetamide (II).

The reaction mixture was treated with an aqueous saturated $NaHCO_3$ solution and the white insoluble solid was filtered and then washed successively with $H_2O$ and hexanes. The desired product was purified by recrystallization from chloroform hexanes to give II in 94% yield: $R_f$ 0.43 (97:3 chloroform/methanol): m.p. 165°–167°: i.r. (KBr) 3280, 1630 (br), 1520 (br), 1430, 1365, 1280, 1245, 1180 $cm^{-1}$; $^1H$ n.m.r. (DMSO-$d_6$) 81.83 (s, $CH_3CO$), 4.22–4.36 (m. $CH_2$), 5.90 (d, J=9.0 Hz, NH), 8,84 (t, J=5.4 Hz, NH); $^{13}C$ n.m.r. (DMSO-$d_6$) 22.34 ($CH_3CO$), 42.25 ($CH_2$), 57.65 (CH), 126.86 ($C_4'$), 127.20 ($2C_2'$) 123.73 ($C_4'$), 128.28 ($2C_2'$ or $2C_3'$), 128.88 ($2C_2'$ or $2C_3'$), 132.36 ($2C_3'$), 132.51 ($C_1'$), 138.76 ($C_1'$), 167.09 (CONH) 168.97 ($CH_3CO$)ppm; mass spectrum, m/e (relative intensity) 315 (M+1,1), 205 (17), 163 (40), 138 (8), 110 (90), 109 (29), 106 (96), 93 (35), 91 (100).

Anal. calc. for $C_{17}H_{18}N_2O_2S$: C 64.94, H 5.77. Found: C 65.27, H 5.54.

EXAMPLE 83

Synthesis of α-Acetamido-N-benzyl-2-(tetrahydrofuran) acetamide (3).

A methanolic solution (70 mL) of α-acetamido-N-benzyl-2-furanacetamide (3.50 g, 12.85 mmol) was hydrogenated (35–40 psi) in the presence of Pd/C (10%, 0.44 g) (44 h). The catalyst was filtered through celite, washed with MeOH (10 mL) and the filtrate concentrated to dryness in vacuo to give 3a and 3b (3.50 g) as a white solid. The products were fractionally recrystallized from EtOAc to give 1.30 g (37%) of 3a: mp 159°–161° C.; $R_f$ 0.38 (6% MeOH/CHCl$_3$); IR (KBr) 3340 (br), 3000, 1600, 1550 (br), 1420, 1350, 720, 680 $cm^{-1}$; $^1H$ NMR (DMSO-$d_6$) δ 1.66–1.90 (m, $C_3H_2$, $C_4H_2$), 1.85 (C(O)$CH_3$), 3.62–3.68 (m, $C_5HH'$), 3.75–3.80 (m, $C_5HH'$), 3.98–4.00 (m, $C_2H$), 4.26–4.38 (m, CH, $CH_2$), 7.18–7.32 (m, 5 PhH), 8.11 (d, J=8.8 Hz, NH), 8.52 (t, J=5.8 Hz, NH); $^{13}C$ NMR (DMSO-$d_6$) 22.52 (C(O)$CH_3$), 24.78 ($C_3$), 27.82 ($C_4$), 41.96 ($CH_2$), 55.67 (CH), 67.54 ($C_5$), 78.48 ($C_2$), 126.58 ($C_4'$), 127.97 ($2C_2'$ or $2C_3'$), 128.12 ($2C_2'$ or $2C_3'$), 139.27 ($C_1'$), 169.09 (C(O)NH), 170.09 (C(O)$CH_3$) ppm; mass spectrum m/e (relative intensity) 277 ($M^+$+1, 4), 206 (52), 142 (13), 106 (38), 91 (100), 71 (97). Anal. ($C_{15}H_{20}N_2O_3$) C, H, N.

The remaining EtOAc mother liquor after recrystallization was concentrated to half its volume and hexane was added dropwise while heating until the solution became turbid. A white solid (0.65 g, 18%) separated on cooling and was collected by filtration to give diastereoisomer 3b: mp 130°–132° C.; $R_f$ 0.38 (6% MeOH/CHCl$_3$); $^1H$ NMR (DMSO-$d_6$) δ 1.55–1.86 (m, $C_3H_2$, $C_4H_2$), 1.89 C(O)$CH_3$), 3.55–3.64 (m, $C_5HH'$), 3.70–3.78 (m, $C_5HH'$), (s, 4.08–4.11 (m, $C_2H$), 4.27 (d, J=5.8 Hz, $CH_2$), 4.36 (dd, J=4.7, 8.6 Hz, CH), 7.21–7.32 (m, 5 PhH), 7.94 (d, J=8.6 Hz, NH), 8.39 (t, J=5.8 Hz, NH); $^{13}C$ NMR (DMSO-$d_6$) 22.45 (C(O)$CH_3$), 25.16 ($C_4$), 27.53 ($C_3$), 42.04 ($CH_2$), 55.48 (CH), 67.53 ($C_5$), 78.26 ($C_2$), 126.59 ($C_4'$), 127.04 ($2C_2'$ or $2C_3'$), 128.10 ($2C_2'$ or $2C_3'$), 139.21 ($C_1'$), 169.55 (C(O)NH), 169.79 (C(O)$CH_3$) ppm; mass spectrum m/e (relative intensity) 277 ($M^+$+1, 4), 206 (50), 142 (23), 106 (39), 1 (100), 71 (96). Anal. ($C_{15}H_{20}N_2O_3$) C, H, N.

EXAMPLE 84

Synthesis of Methyl α-Acetamido-2-methyl-2-furanacetate (17). HBr was bubbled (2.5 min) through a CDCl$_3$ solution (25 mL) of 15 (3.80 g, 26.6 mmol). The excess HBr and CDCl$_3$ were removed by evaporating the solution with a continuous stream of Ar (20–30 min). The light yellow oily residue that remained containing 16 was dissolved in THF (100 mL), and then furan (32.76 g, 482.0 mmol) and ZnCl$_2$ (1M in ether, 53.0 mL, 53.0 mmol) were added. The reaction was stirred at room temperature (3.5 h) and then treated with H$_2$O (50 mL). The aqueous mixture was extracted with EtOAc (3×100 mL), and the combined extracts were dried (Na$_2$SO$_4$). The volatile materials were removed by distillation in vacuo to give 5.00 g (89%) of 17: $R_f$ 0.35 (50%, EtOAc/CHCl$_3$); $^1H$ NMR (CDCl$_3$) δ 1.94 (s, $CH_3$), 1.99 (s, C(O)$CH_3$), 3.74 (s, C(O)O$CH_3$), 6.36 (br s, $C_3H$, $C_4H$), 6.83 (s, NH), 7.35 (s, $C_5H$); $^{13}C$ NMR (CDCl$_3$) 21.43 ($CH_3$), 23.26 (C(O)$CH_3$), 53.03 (C(O)O$CH_3$), 58.36 (C(OH$_3$)), 107.39 ($C_4$), 110.52 ($C_3$), 142.10 ($C_5$), 152.03 ($C_2$), 169.21 (C(O)$CH_3$), 171.34 (C(O)O$CH_3$) ppm.

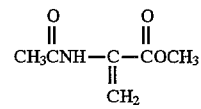

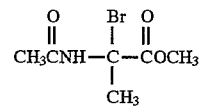

EXAMPLE 85

Synthesis of α-Acetamido-2-methyl-2-furanacetic Acid (18).

A 95% EtOH solution (150 mL) of 17 (5.00 g, 23.6 mmol) and KOH (3.00 g, 53.5 mmol) was stirred at room temperature (48 h). The solvent was removed and the residue was dissolved in H$_2$O (50 mL). The aqueous solution was washed with Et$_2$O (3×50 mL) and then acidified to pH 1.5 with 10% H$_3$PO$_4$. The acidified solution was extracted with EtOAc (3×200 mL) and the combined extracts were dried (Na$_2$SO$_4$), and concentrated in vacuo to give 2.90 g (62%) of 18: mp 178°–180° C. (d) (recrystallized from CH$_3$CN); IR (KBr) 3400 (br), 1700 (br) $cm^{-1}$; $^1H$ NMR (DMSO-$d_6$) δ 1.67 (s, $CH_3$), 1.83 (s, C(O)$CH_3$), 6.39 (m, $C_3H$, $C_4H$), 7.59 (s, $C_5H$), 8.34 (s, NH), 12.63 (s, C(O)OH); $^{13}C$ NMR (DMSO-$d_6$) 22.20 (C(O)$CH_3$), 22.59 ($CH_3$), 57.65 (C(CH$_3$)), 107.09 ($C_4$), 110.49 ($C_3$), 142.33 ($C_5$), 153.36 ($C_2$), 168.86 (C(O)NH), 171.78 (C(O)OH) ppm; mass spectrum, m/e (relative intensity) 198 ($M^+$+1, 4), 143 (97), 152 (63), 140 (23), 111 (73), 110 (100), 94 (24). Anal. ($C_9H_{11}NO_4$) C, H, N.

EXAMPLE 86

Synthesis of α-Acetamido-N-benzyl-2-methyl-2-furanacetamide (4).

Employing the mixed carbonic anhydride coupling procedure with 18 (2.40 g, 12.2 mmol), 4-methylmorpholine (1.23 g, 12.2 mmol), isobutylchloroformate (1.83 g, 13.4 mmol), and benzylamine (1.43 g, 12.7 mmol) gave 4 (1.50 g, 43%) as a thick oil: $R_f$ 0.29 (2% MeOH/CHCl$_3$); $^1$H NMR (CDCl$_3$) δ 1.94 (s, CH$_3$), 1.98 (s, C(O)CH$_3$), 4.40 (d, J=5.6 Hz, CH$_2$), 6.20 (br s, NH), 6.34–6.37 (m, C$_3$H, C$_4$H), 7.05–7.36 (m, NH, C$_5$H, 5 PhH); $^{13}$C NMR (CDCl$_3$) 22.31 (C(O)CH$_3$), 23.81 (CH$_3$), 43.77 (CH$_2$), 58.50 (C(CH$_3$)), 107.94 (C$_4$), 110.67 (C$_3$), 126.99 (2C$_2$' or 2C$_3$'), 127.41 (C$_4$'), 128.60 (2C$_2$' or 2C$_3$'), 137.52 (C$_1$'), 142.38 (C$_5$), 152.94 (C$_2$), 169.03 (C(O)NH), 171.16 (COCH$_3$) ppm; mass spectrum, m/e (relative intensity) 287 (M$^+$+1, 4), 228 (4), 153 (99), 152 (96), 138 (15), 111 (63), 110 (100), 91 (75); M$_r$ (EI) 286.13074 (calcd for C$_{16}$H$_{18}$N$_2$O$_3$, 286.13174).

EXAMPLE 87

Synthesis of α-Thioacetamido-N-benzyl-2-furanacetamide (5).

A THF solution (80 mL) of 2 (1.00 g, 3.68 mmol) and Lawesson's reagent (0.73 g, 1.84 mmol) was stirred at room temperature (4 h). The THF was removed in vacuo and the residue was purified by flash column chromatography on SiO$_2$ gel using 1% MeOH/CHCl$_3$ to give 0.75 g (71%) of 5: mp 78°–80° C.; $R_f$ 0.51 (1% MeOH/CHCl$_3$); IR (KBr) 3200 (br), 1630, 1500, 1440, 1350, 790, 710, 680 cm$^{-1}$; $^1$H NMR (DMSO-d$_6$) δ 2.46 (s, C(S)CH$_3$), 4.27–4.35 (m, CH$_2$), 6.22 (d, J=7.7 Hz, CH), 6.32 (d, J=3.3 Hz, C$_3$H), 6.41–6.44 (m, C$_4$H), 7.15–7.33 (m, 5 PhH), 7.64 (s, C$_5$H), 8.81 (t, J=5.9 Hz, NH), 10.54 (d, J=7.7 Hz, NH); $^{13}$C NMR (DMSO-d$_6$) 32.70 (s, C(S)CH$_3$), 42.39 (C$_2$), H 56.82 (CH), 108.76 (C$_3$), 110.67 (C$_4$), 126.81 (C$_4$'), 127.12 (2C$_2$' or 2C$_3$'), 128.23 (2C$_2$' or 2C$_3$'), 139.98 (C$_1$'), 143.06 (C$_5$), 149.53 (C$_2$), 166.55 (C(O)NH), 200.68 (C(S)CH$_3$) ppm; mass spectrum (FD) 288 (M$^+$). Anal. (C$_{15}$H$_{16}$N$_2$O$_2$S) C, H, N.

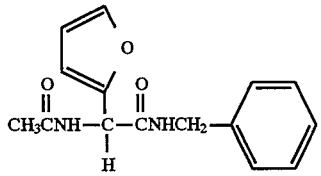

EXAMPLE 88

Synthesis of α-Thioacetamido-N-benzyl-2-furanthioacetamide (6).

A THF solution (90 mL) of 2 (2.00 g, 7.35 mmol) and Lawesson's reagent (3.27 g, 8.09 mmol) was heated to reflux (4 h). The THF was removed in vacuo and the residue was purified by two successive flash column chromatographies on SiO$_2$ gel using 0.5% MeOH/CHCl$_3$ as the eluant in the first chromatography and CHCl$_3$ in the second chromatography. Compound 6 (0.50 g, 22%) was then further purified by preparative TLC (CHCl$_3$): mp 99°–101° C.; $R_f$ 0.74 (1% MeOH/CHCl$_3$); IR (KBr) 3100, 1580, 1500 (br) cm$^{-1}$; $^1$H NMR (DMSO-d$_6$) δ 2.58 (s, C(S)CH$_3$), 4.86 (dd, J=5.4, 15.0 Hz, CHH), 4.96 (dd, J=5.4, 15.0 Hz, CHH), 6.49–6.55 (m, C$_3$H, C$_4$H), 6.65 (d, J=7.5 Hz, CH), 7.31–7.43 (m, 5 PhH), 7.75 (s, C$_5$H) 10.64 (d, J=7.5 Hz, NH), 10.95 (t, J=5.4 Hz, NH); $^{13}$C NMR (DMSO-d$_6$) 32.79 (s, C(S)CH$_3$), 48.30 (CH$_2$), 61.88 (CH), 108.50 (C$_3$), 110.53 (C$_4$), 127.05 (C$_4$'), 127.48 (2C$_2$' or 2C$_3$'), 128.19 (2C$_2$' or 2C$_3$'), 136.67 (C$_1$'), 142.91 (C$_5$), 150.15 (C$_2$), 197.45 (C(S)NH), 200.56 (C(S)CH$_3$) ppm; mass spectrum (FD) 304 (M$^+$). Anal. (C$_{15}$H$_{16}$N$_2$OS$_2$) C, H, N.

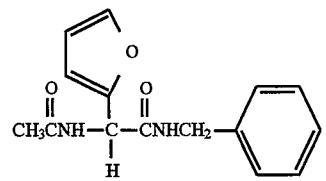

EXAMPLE 89

Synthesis of α-Acetamido-N-(3-pyridinylmethyl)-2-furanacetamide (7).

Using racemic 19 (3.00 g, 16.39 mmol), 4-methylmorpholine (1.66 g, 16.39 mmol), isobutylchloroformate (2.24 g, 16.39 mmol), and 3-aminomethylpyridine (1.77 g, 16.39 mmol) in the mixed carbonic anhydride protocol gave 3.35 g (75%) of 7: mp 172°–174° C. (recrystallized from EtOAc); $R_f$ 0.27 (8% MeOH/CHCl$_3$); IR (KBr) 3400, 3300, 1640, 1540, 1420, 1360, 820, 740 cm$^{-1}$; $^1$H NMR (DMSO-d$_6$) δ 1.89 (s, C(O)CH$_3$), 4.32 (d, J=5.8 Hz, CH$_2$), 5.55 (d, J=7.9 Hz, CH), 6.28–6.29 (m, C$_3$H), 6.41–6.43 (m, C$_4$H), 7.32 (dd, J=4.8, 7.7 Hz, C$_5$'H), 7.58–7.62 (m, C$_4$'H, C$_5$H), 8.44 (br s, C$_2$'H, C$_6$'H), 8.62 (d, J=7.9 Hz, NH), 8.81 (t, J=5.8 Hz, NH); $^{13}$C NMR (DMSO-d$_6$) 22.31 (C(O)CH$_3$), 39.98 (CH$_2$), 50.94 (CH), 107.67 (C$_4$), 110.54 (C$_3$), 123.38 (C$_5$'), 134.57 (C$_3$'), 134.83 (C$_4$'), 142.64 (C$_5$), 148.06 (C$_6$'), 148.55 (C$_2$'), 150.94 (C$_2$), 168.19 (C(O)NH), 169.26 (C(O)CH$_3$) ppm; mass spectrum (FD) 274 (M$^+$+1). Anal. (C$_{14}$H$_{15}$N$_3$O$_3$) C, H, N.

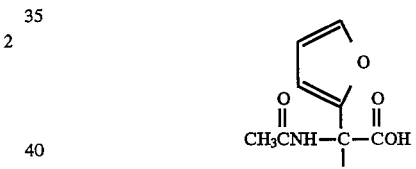

EXAMPLE 90

Synthesis of α-Acetamido-N-(4-pyridinylmethyl)-2-furanacetamide (8).

Making use of racemic 19 (3.00 g, 16.39 mmol), 4-methylmorpholine (1.66 g, 16.39 mmol), isobutylchloroformate (2.24 g, 16.39 mmol), and 4-aminomethylpyridine (1.77 g, 16.39 mmol) in the mixed carbonic anhydride method, gave 3.40 g (76%) of 8: mp 168°–170° C. (recrystallized from EtOAc); $R_f$ 0.31 (8% MeOH/CHCl$_3$); IR (KBr) 3180, 1650 (br), 1480, 1400, 1340, 780, 740 cm$^{-1}$; $^1$H NMR (DMSO-d$_6$) δ 1.90 (s, C(O)CH$_3$), 4.32 (d, J=5.7 Hz, CH$_2$), 5.57 (d, J=7.8 Hz, CH), 6.32–6.34 (m, C$_3$H), 6.42–6.43 (m, C$_4$H), 7.19 (d, J=4.9 Hz, C$_3$'H, C$_5$'H), 7.64 (s, C$_5$H), 8.46 (d, J=4.9 Hz, C$_2$'H, C$_6$'H), 8.64 (d, J=7.8 Hz, NH), 8.84 (t, J=5.7 Hz, NH); $^{13}$C NMR (DMSO-d$_6$) 22.27 (C(O)CH$_3$), 41.26 (CH$_2$), 50.99 (CH), 107.74 (C$_4$), 110.54 (C$_3$), 121.87 (C$_3$', C$_5$'), 142.63 (C$_5$), 148.17 (C$_4$'), 149.35 (C$_2$', C$_6$'), 150.82 (C$_2$), 168.35 (C(O)NH), 169.29 (C(O)CH$_3$) ppm; mass spectrum (FD) 274 (M$^+$+1). Anal. (C$_{14}$H$_{15}$N$_3$O$_3$) C, H, N.

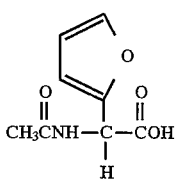

EXAMPLE 91

Synthesis of α-Acetamido-N-(1-oxo-3-pyridinylmethyl)-2-furanacetamide (9).

A solution of 7 (1.50 g, 5.49 mmol) and m-chloroperoxybenzoic acid (1.90 g, 6.04 mmol) in THF (175 mL) was heated to reflux (3 h) and then cooled to room temperature. The THF solution was concentrated to approximately half its volume, and then cooled to give 1.00 g (63%) of 9: mp 159°–161° C. (recrystallized from EtOH); $R_f$ 0.30 (20% MeOH/CHCl$_3$); IR (KBr) 3400 (br), 1620, 1500 (br), 1420, 1350, 750 cm$^{-1}$; $^1$H NMR (DMSO-d$_6$) δ 1.89 (s, C(O)CH$_3$), 4.27 (d, J=5.0 Hz, CH$_2$) 5.53 (d, J=7.6 Hz, CH), 6.31 (br s, C$_3$H), 6.42 (br s, C$_4$H), 7.14–7.18 (m, 1 ArH), 7.34–7.37 (m, 1 ArH), 7.61 (br s, C$_5$H), 8.07 (s, 2 ArH), 8.63 (br s, NH), 8.80 (br s, NH); $^{13}$C NMR (DMSO-d$_6$) 22.29 (C(O)CH$_3$), 39.36 (CH$_2$), 50.99 (CH), 107.79 (C$_4$), 110.56 (C$_3$), 124.03 (C$_4$'), 126.10 (C$_5$'), 137.16 (C$_3$'), 137.31 (C$_6$'), 138.70 (C$_2$'), 142.69 (C$_5$), 150.72 (C$_2$), 168.40 (C(O)NH), 169.32 (C(O)CH$_3$) ppm; mass spectrum (FD) 289 (M$^+$); M$_r$ (EI) 289.10554 (calcd for C$_{14}$H$_{15}$N$_3$O$_4$, 289.10626).

Anal. Calcd for C$_{14}$H$_{15}$N$_3$O$_4$.2.0 H$_2$O: C, 51.69; H, 5.89; N, 12.92. Found: C, 52.03; H, 5.56; N, 13.36.

EXAMPLE 92

Synthesis of α-Acetamido-N-(1-oxo-4-pyridinylmethyl)-2-furanacetamide (10).

Following the preceding procedure and using 8 (1.50 g, 5.49 mmol) and m-chloroperoxybenzoic add (1.90 g, 6.04 mmol) gave a light yellow solid (0.96 g, 60%) directly upon cooling the THF solution. The precipitate was filtered and recrystallized from EtOH to give 10: mp 210°–212° C. (d); $R_f$ 0.25 (20% MeOH/CHCl$_3$); IR (KBr) 3300, 1620, 1500, 1410, 1350, 740 cm$^{-1}$; $^1$H NMR (DMSO-d$_6$) δ 1.89 (s, C(O)CH$_3$), 4.26 (d, J=5.8 Hz, CH$_2$), 5.52 (d, J=7.7 Hz, CH), 6.30 (br s, C$_3$H), 6.41–6.42 (m, C$_4$H), 7.21 (d, J=6.8 Hz, C$_3$'H, C$_5$'H), 7.63 (s, C$_5$H), 8.14 (d, J=6.8 Hz, C$_2$'H, C$_6$'H), 8.62 (d, J=7.7 Hz, NH), 8.82 (t, J=5.8 Hz, NH); $^{13}$C NMR (DMSO-d$_6$) 22.35 (C(O)CH$_3$), 40.68 (CH$_2$), 51.14 (CH), 107.87 (C$_4$), 110.62 (C$_3$), 124.83 (C$_3$', C$_5$'), 137.43 (C$_4$'), 138.39 (C$_2$', C$_6$'), 142.72 (C$_5$), 150.77 (C$_2$), 168.48 (C(O)NH), 169.45 (C(O)CH$_3$) ppm; mass spectrum (FD) 289 (M$^+$). Anal. (C$_{14}$H$_{15}$N$_3$O$_4$) C, H, N.

EXAMPLE 93

Synthesis of α-Acetamido-2-furanacetic-2'-pyridinehydrazide (11).

Following the mixed carbonic anhydride procedure and using racemic 19 (2.00 g, 10.39 mmol), 4-methylmorpholine (1.10 g, 10.93 mmol), isobutylchloroformate (1.49 g, 10.93 mmol), and 2-hydrazinopyridine (1.20 g, 11.00 mmol) gave an insoluble material upon workup containing 11 and 4-methylmorpholine hydrochloride. The reaction products were suspended in EtOH (25 mL), and 11 (1.00 g) was collected by filtration. Concentration of the THF filtrate and trituration of the residue with EtOAc gave an additional 0.70 g of 11 to give a combined yield of 1.70 g (64%): mp 226°–228° C. (recrystallized from EtOH); $R_f$ 0.30 (10% MeOH/CHCl$_3$); IR (KBr) 3400, 1650, 1580, 1440, 1360, 1320, 770, 730 cm$^{-1}$; $^1$H NMR (DMSO-d$_6$) δ 1.83 (s, C(O)CH$_3$), 5.64 (d, J=8.0 Hz, CH), 6.41–6.50 (m, C$_3$H, C$_4$H, C$_5$'H), 6.67 (dd, J=5.4, 6.7 Hz, C$_3$'H), 7.44–7.52 (m, C$_4$'H), 7.66 (s, C$_5$H), 8.02 (d, J=4.0 Hz, C$_6$'H), 8.40 (s, C(O)NHNH), 8.66 (d, J=8.0 Hz, NH), 10.20 (s, C(O)NHNH); $^{13}$C NMR (DMSO-d$_6$) 22.26 (C(O)CH$_3$), 49.56 (CH), 105.93 (C$_3$'), 107.87 (C$_3$), 110.57 (C$_4$), 114.50 (C$_5$'), 137.48 (C$_4$'), 142.76 (C$_5$), 147.45 (C$_6$'), 150.60 (C$_2$), 159.59 (C$_2$'), 167.88 (C(O)NH), 169.28 (C(O)CH$_3$) ppm; mass spectrum (FD) 274 (M$^+$); M$_r$ (EI) 274.10649 (calcd for C$_{13}$H$_{14}$N$_4$O$_3$, 274.10659).

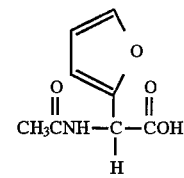

EXAMPLE 94

Synthesis of R(–) α-Acetamido-N-(4-fluorobenzyl)-2-furanacetamide ((R)-12).

Using (R)-19 (0.94 g, 5.1 mmol), 4-methylmorpholine (0.52 g, 5.1 mmol), isobutylchloroformate (0.70 g, 5.1 mmol), and 4-fluorobenzylamine (0.65 g, 5.16 mmol) in the mixed carbonic anhydride method gave 1.00 g (68%) of (R)-12: mp 205°–207° C. (recrystallized from EtOAc); $R_f$ 0.30 (4% MeOH/CHCl$_3$); [α]$^{26}_D$=–77.42 (c=1, MeOH); IR (KBr) 3400 (br), 1620, 1580, 1500 (br), 1350, 770, 720 cm$^{-1}$; $^1$H NMR (DMSO-d$_6$) δ 1.89 (s, C(O)CH$_3$), 4.27 (d, J=5.9 Hz, CH$_2$), 5.54 (d, J=8.0 Hz, CH), 6.27 (d, J=3.0 Hz, C$_3$H), 6.41 (dd, J=1.9, 3.0 Hz, C$_4$H), 7.08–7.15 (m, 2 ArH), 7.20–7.26 (m, 2 ArH), 7.61 (d, J=1.9 Hz, C$_5$H), 8.58 (d, J=8.0 Hz, NH), 8.74 (t, J=5.9 Hz, NH) ppm; addition of R(–) mandelic add to a CDCl$_3$ solution of (R)-12 gave only one signal for the acetamide methyl protons. Mass spectrum (FD) 290 (M$^+$) Anal. (C$_{15}$H$_{15}$FN$_2$O$_3$) C, H, N.

Synthesis of R(–)α-Acetamido-N-(4-methylbenzyl)-2-furanacetamide ((R-13).

Employing the mixed carbonic anhydride procedure and making use of (R)-19 (1.50 g, 8.20 mmol), 4-methylmorpholine (0.83 g, 8.20 mmol), isobutylchloroformate (1.12 g, 8.20 mmol), and 4-methylbenzylamine (0.99 g, 8.20 mmol) gave 1.80 g (77%) of (R)-13: mp 210°–212° C. (recrystallized from EtOAc); $R_f$ 0.54 (4% MeOH/CHCl$_3$); [α]$^{26}_D$=–74.43 (c=1, MeOH); IR (KBr) 3400 (br), 1610 (br), 1500 (br), 1350, 1320, 780, 720 cm$^{-1}$; $^1$H NMR (DMSO-d$_6$) δ 1.89 (s, C(O)CH$_3$), 2.25 (s, CH$_3$), 4.24 (d, J=5.5 Hz, CH$_2$), 5.56 (d, J=8.1 Hz, CH), 6.28 (br s, C$_3$H), 6.41 (br s, C$_4$H), 7.09 (br s, 4ArH), 7.61 (br s, C$_5$H), 8.58 (d, J=8.1 Hz, NH), 8.72 (t, J=5.5 Hz, NH) addition of (R)-(–)mandelic acid to a CDCl$_3$ solution of (R)-13 gave only one signal for the acetamide methyl protons. $^{13}$C NMR (DMSO-d$_6$) 20.64 (CH$_3$), 22.32 (C(O)CH$_3$), 42.00 (CH$_2$), 50.88 (CH), 107.52 (C$_4$), 110.50 (C$_3$), 127.06 (2C$_2$' or 2C$_3$'), 128.77 (2C$_2$' or 2C$_3$'), 135.82 (C$_1$' or C$_4$'), 135.98 (C$_1$' or C$_4$'), 142.51 (C$_5$), 151.21 (C$_2$) 167.87 (C(O)NH), 169.17 (C(O)CH$_3$) ppm; mass spectrum (FD) 287 (M$^+$+1). Anal. (C$_{16}$H$_{18}$N$_2$O$_3$) C, H, N.

EXAMPLE 95

Synthesis of R(–)α-Acetamido-N-(4-trifluoromethylbenzyl)-2-furanacetamide ((R)-14).

Using (R)-19 (1.00 g, 5.46 mmol), 4-methylmorpholine (0.55 g, 5.46 mmol), isobutylchloroformate (0.75 g, 5.46 mmol), and 4-trifluoromethylbenzylamine (0.96 g, 5.46 mmol) in the mixed carbonic anhydride protocol gave 1.15 g (59%) of (R)-14: m.p 193°–195° C. (recrystallized from EtOAc/hexane); $[\alpha]^{26}_D = -69.27$ (c=1, MeOH); IR (KBr) 3220, 1610, 1520, 1400, 1350, 800, 720 cm$^{-1}$; $^1$H NMR (DMSO-d$_6$) δ 1.89 (s, C(O)CH$_3$), 4.37 (d, J=5.8 Hz, CH$_2$), 5.56 (d, J=7.9 Hz, CH), 6.30–6.31 (m, C$_3$H), 6.41–6.43 (m, C$_4$H), 7.40–7.43 (m, 2ArH), 7.63–7.68 (m, 2ArH, C$_5$H), 8.62 (d, J=7.9 Hz, NH), 8.44 (t, J=5.8 Hz, NH); addition of (R)(−)-mandelic acid to a CDCl$_3$ solution of (R)-14 gave only one signal for the acetamide methyl protons. Mass spectrum (FD) 340 (M$^+$). Anal. (C$_{16}$H$_{15}$F$_3$N$_2$O$_3$) C, H, N.

GENERAL SYNTHESIS

General Synthesis—Several preparative routes were utilized for the construction of the targetted compounds. In most cases, 2-acetamido-N-benzyl-2-aminoacetamide (2r) served as the starting material. Treatment of 2r with the appropriate chloroformate, isocyanate, isothiocyanate, arthydride, or use of the mixed anhydride protocol advanced for peptide synthesis led to the preparation of the N-acyl substituted adducts 2e–2l and 2n. Correspondingly, the preformed α-bromo derivative 2s was employed as the immediate precursor for 2m and 2p, while 2-acetamido-N-benzyl-2-(trimethylammonio)acetamide tetrafluoroborate (2t) was utilized for the synthesis of 2o. Finally, alkaline hydrolysis of 2p, followed by neutralization of the dipeptide by passage through an ion exchange resin yielded 2g.

In Examples 96–108, reference is made to the following compounds

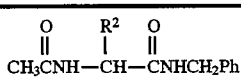
$$\text{CH}_3\text{CNH}-\text{CH}-\text{CNHCH}_2\text{Ph}$$
with O, R², O above and ‖, |, ‖

2a R² = NHCH$_2$CH$_3$
b R² = NHNHCO$_2$CH$_2$Ph
c R² = NH(OCH$_3$)
d R² = N(CH$_3$)OCH$_3$
e R² = NHC(O)OCH$_3$
f R² = NHC(O)OPh
g R² = NHC(O)NHCH$_3$
h R² = NHC(O)NHPh
i R² = NHC(O)NHS(O$_2$)Ph
j R² = NHC(S)NHCH$_3$
k R² = NHC(S)NHPh
l R² = NHC(O)Ph(2'CO$_2$H)

m 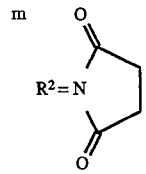
R²=N with two C=O groups n R² = NHC(O)CH$_2$NHC(O)OCH$_2$Ph
o R² = NHCH$_2$C(O)OCH$_2$CH$_3$
p R² = NHCH$_2$C(O)OCH$_2$Ph
q R² = ⁺NH$_2$CH$_2$CO$_2$⁻
r R² = NH$_2$
s R² = Br
t R² = ⁺N(CH$_3$)$_3$, BF$_4$⁻
u R² = NHC(O)CH$_3$
v R² = NHC(O)CF$_3$

EXAMPLE 96

Chemistry—Synthesis of Methyl[acetamido(benzylcarbamoyl)methyl]carbomate (2e).

Methyl chloroformate (0.33 g, 3.35 mmol) was added to a solution 2r (0.70 g, 3.16 mmol) and Et$_3$N (0.39 g, 3.80 mmol) in THF (75 mL), and then the reaction mixture was stirred at 55°–60° C. (2 h). The Et$_3$N.HCl that precipitated was filtered and the filtrate was concentrated to dryness in vacuo. The residue was triturated with EtOAc (20 mL), and the remaining white solid (0.55 g, 62%) was filtered and recrystallized from EtOH: mp. 202°–204° C. (d); R$_f$ 0.53 (10% MeOH/CHCl$_3$); IR (KBr) 3260, 1650, 1500, 1440, 1360, 780, 690 cm$^{-1}$; $^1$H NMR (DMSO-d$_6$) δ 1.86 (s, C(O)CH$_3$), 3.54 (s, OCH$_3$), 4.27 (d, J=5.6 Hz, CH$_2$), 5.56 (t, J=7.8 Hz, CH), 7.18–7.32 (m, 5PhH), 7.70 (br s, NHC(O)OCH$_3$), 8.40 (d, J=7.8 Hz, NH), 8.51 (t, J=5.6 Hz, NH); $^{13}$C NMR (DMSO-d$_6$) 22.38 (C(O)CH$_3$), 42.29 (CH$_2$), 51.46 (OCH$_3$), 58.57 (CH), 126.52 (C$_4$'), 126.98 (2C$_2$' or 2C$_3$'), 127.99 (2C$_2$' or 2C$_3$'), 139.03 (C$_1$'), 167.83 (C(O)NH), 169.33 (C(O)CH$_3$) ppm, the carbamate carbonyl signal was not detected. Mass spectrum (FD) 279 (M$^+$).

Anal. Calcd for C$_{13}$H$_{17}$N$_3$O$_4$: C, 55.91; H, 6.14; N, 15.05. Found: C, 56.16; H, 6.10; N, 14.89.

EXAMPLE 97

Synthesis of Phenyl[acetamido(benzylcarbamoyl)methyl]carbamate (2f).

Compound 2r (0.80 g, 3.62 mmol) was dissolved in warm THF (75 mL), and then Et$_3$N (0.44 g, 4.35 mmol), and phenyl chloroformate (0.62 g, 3.98 mmol) were added. The reaction mixture was stirred at 45°–50° C. (2 h), and the volatile materials were removed in vacuo. The residue was triturated with EtOAc (20 mL) and the remaining white solid material (0.80 g, 65%) was filtered, washed with H$_2$O (10 mL), and then recrystallized from MeOH: mp 201°–203° C.; R$_f$ 0.38 (5% MeOH/CHCl$_3$); IR (KBr) 3400 (br), 3240, 1700, 1630, 1500, 1460, 1320, 1200, 740, 600 cm$^{-1}$; $^1$H NMR (DMSO-d$_6$) δ 1.89 (s, C(O)CH$_3$), 4.29–4.35 (m, CH$_2$), 5.66 (t, J=7.6 Hz, CH), 7.08–7.42 (m, 10ArH), 8.43 (d, J=7.6 Hz, NH), 8.58 (d, J=7.6 Hz, NH), 8.67 (t, J=5.0 Hz, NH); $^{13}$C NMR (DMSO-d$_6$) 22.58 (C(O)CH$_3$), 42.51 (CH$_2$), 58.69 (CH), 121.70 (2C$_2$), 125.18 (C$_4$), 126.76 (C$_4$'), 127.19 (2C$_2$' or 2C$_3$'), 128.21 (2C$_2$' or 2C$_3$'), 129.30 (2C$_3$), 139.14 (C$_1$'), 150.91 (C$_1$), 167.73 (C(O)NH), 169.75 (C(O)CH$_3$) ppm, the signal for the carbamate carbonyl was not detected. Mass spectrum (FD) 341 (M$^+$).

Anal. Calcd for C$_{18}$H$_{19}$N$_3$O$_4$: C, 63.33; H, 5.61; N, 12.31. Found: C, 63.06; H, 5.64; N, 12.12.

EXAMPLE 98

Synthesis of 1-[Acetamido(benzylcarbamoyl)methyl]-3-methylurea (2g).

Methyl isocyanate (0.20 g, 3.48 mmol) was added to a solution of 2r (0.70 g, 3.16 mmol) in THF (75 mL), and then the reaction was stirred at 45°–50° C. (2 h). The white solid (0.80 g, 91%) that separated out was filtered and recrystallized from MeOH to give 2g: mp 229°–230° C. (d); R$_f$ 0.25 (10% MeOH/CHCl$_3$); IR (KBr) 3200, 3060, 1630, 1500 (br), 1350, 1300, 740, 680 cm$^{-1}$; $^1$H NMR (DMSO-d$_6$) δ 1.82 (s, C(O)CH$_3$), 2.54 (d, J=4.5 Hz, NHCH$_3$), 4.26 (d, J=5.8 Hz, CH$_2$), 5.59 (t, J=7.8 Hz, CH), 6.19 (d, J=4.5 Hz, NHCH$_3$), 6.52 (d, J=7.8 Hz, NHC(O)NHCH$_3$), 7.20–7.31 (m, 5PhH), 8.38 (t, J=5.8 Hz, NH), 8.46 (d, J=7.8 Hz, NH); $^{13}$C NMR (DMSO-d$_6$) 22.36 (C(O)CH$_3$), 26.03 (NHCH$_3$), 42.19 (CH$_2$), 57.92 (CH), 126.54 (C$_4$'), 126.93 (2C$_2$' or 2C$_3$'), 128.06 (2C$_2$' or 2C$_3$'), 139.16 (C$_1$'), 157.30 (NHC(O)NH), 168.89 (C(O)NH), 169.37 (C(O)CH$_3$) ppm; mass spectrum (FD) 279 (M$^+$+1).

Anal. Calcd for C$_{13}$H$_{18}$N$_4$O$_3$: C, 56.10; H, 6.52; N, 20.13. Found: C, 56.31; H, 6.41; N, 20.12.

EXAMPLE 99

Synthesis of 1-[Acetamido(benzylcarbamoyl)methyl]-3-phenylurea (2h).

Phenyl isocyanate (0.42 g, 3.5 mmol) was added to a solution of 2r (0.70 g, 3.16 mmol) in THF (75 mL), and then the reaction was stirred at 45°–50° C. (2 h). The white solid (0.95 g, 89%) that precipitated was filtered and dried: mp 242°≧244° C. (d); $R_f$ 0.30 (5% MeOH/CHCl$_3$); IR (KBr) 3200 (br), 1600 (br), 1430 (br), 1300, 880, 700 cm$^{-1}$; $^1$H NMR (DMSO-d$_6$) δ 1.86 (s, C(O)CH$_3$), 4.30 (d, J=5.9 Hz, CH$_2$), 5.67 (t, J=7.6 Hz, CH), 6.86–6.93 (m, 2ArH), 7.20–7.32 (m, NH, 5PhH, 1ArH), 7.37–7.40 (m, 2ArH), 8.56 (t, J=5.9 Hz, NH), 8.68 (d, J=7.6 Hz, NH), 8.89 (s, NH); $^{13}$C NMR (DMSO-d$_6$) 22.38 (C(O)CH$_3$), 42.29 (CH$_2$), 57.59 (CH), 117.61 (2C$_2$), 121.37 (C$_4$), 126.57 (C$_{4'}$), 126.95 (2C$_{2'}$ or 2C$_{3'}$), 128.07 (2C$_{2'}$ or 2C$_{3'}$), 128.62 (2C$_3$), 139.12 (C$_1$ or C$_{1'}$), 139.98 (C$_1$ or C$_{1'}$), 153.98 (NHC(O)NH), 168.55 (C(O)NH), 169.58 (C(O)CH$_3$) ppm; mass spectrum (FD) 340 (M$^+$).

Anal. Calcd for C$_{18}$H$_{20}$N$_4$O$_3$: C, 63.52; H, 5.92; N, 16.46. Found: C, 63.72; H, 5.92; N, 16.20.

EXAMPLE 100

Synthesis of 1-[Acetamido(benzylcarbamoyl)methyl]-3-benzenesulfonylurea (2i).

Benzenesulfonyl isocyanate (0.64 g, 3.48 mmol) was added to a solution of 2r (0.70 g, 3.16 mmol) in THF (75 mL), and then the reaction was stirred at 50°–55° C. (22 h). The white solid (0.84 g, 66%) that separated on cooling was filtered and dried: mp 188°–191° C. (d); $R_f$ 0.11 (10% MeOH/CHCl$_3$); IR (KBr) 3250, 1630 (br), 1500 (br), 1460, 1330, 870, 700 cm$^{-1}$; $^1$H NMR (DMSO-d$_6$) δ 1.80 (s, C(O)CH$_3$), 4.24 (d, J=5.7 Hz, CH$_2$), 5.47 (t, J=7.7 Hz, CH), 7.18–7.30 (m, 5PhH, NH), 7.57–7.71 (m, 3ArH), 7.89–7.92 (d, J=7.5 Hz, 2ArH), 8.54 (t, J=5.7 Hz, NH), 8.70 (d, J=7.7 Hz, NH), 10.80 (s, NH); $^{13}$C NMR (DMSO-d$_6$) 22.29 (C(O)CH$_3$), 42.30 (CH$_2$), 57.14 (CH), 126.58 (C$_{4'}$), 126.89 (2C$_2$), 127.12 (2C$_{2'}$ or 2C$_{3'}$), 128.05 (2C$_{2'}$ or 2C$_{3'}$), 128.96 (2C$_3$), 133.25 (C$_4$), 138.88 (C$_1$ or C$_{1'}$), 139.87 (C$_1$ or C$_{1'}$), 150.36 (NHC(O)NH), 167.55 (C(O)NH), 169.55 (C(O)CH$_3$) ppm; mass spectrum (FD) 405 (M$^+$+1).

Anal. Calcd for C$_{18}$H$_{20}$N$_4$O$_5$S: C, 53.46; H, 4.98; N, 13.85. Found: C, 53.23; H, 5.04; N, 13.62.

EXAMPLE 101

Synthesis of 1-[Acetamido(benzylcarbamoyl)methyl]-3-methylthiourea (2j).

A solution of 2r (0.50 g, 2.26 mmol) and methyl isothiocyanate (0.20 g, 2.27 mmol) in THF (75 mL) was heated to reflux (4 h), and then the volatile materials were removed in vacuo. The residue was recrystallized from absolute EtOH to give 2j as a white solid (0.22 g, 33%): mp 162°–163° C. (d); $R_f$ 0.45 (10% MeOH/CHCl$_3$); IR (KBr) 3400 (br), 3220 (br), 1620, 1500, 1430, 1340, 740 cm$^{-1}$; $^1$H NMR (DMSO-d$_6$) δ 1.83 (s, C(O)CH$_3$), 2.85 (br s, NHCH$_3$), 4.27 (d, J=5.8 Hz, CH$_2$), 6.10 (br s, CH), 7.17–7.30 (m, 5PhH), 7.80 (br s, NH), 7.96 (br s, NH), 8.44 (br s, NH), 8.72 (s, NH); $^{13}$C NMR (DMSO-d$_6$) 22.39 (C(O)CH$_3$), 30.92 (NHCH$_3$), 42.45 (CH$_2$), 61.33 (CH), 126.68 (C$_{4'}$) 127.06 (2C$_{2'}$ or 2C$_{3'}$), 128.16 (2C$_{2'}$ or 2C$_{3'}$), 139.15 (C$_{1'}$), 168.17 (C(O)NH), 170.30 (C(O)CH$_3$) ppm, the signal for the thiocarbonyl carbon group was not detected. Mass spectrum (FD) 294 (M$^+$).

Anal Calcd for C$_{13}$H$_{18}$N$_4$O$_2$S: C, 53.04; H, 6.16; N, 19.03. Found: C, 53.16; H, 6.31; N, 18.89.

EXAMPLE 102

Synthesis of 1-[Acetamido(benzylcarbamoyl)methyl]-3-phenylthiourea (2k).

A solution of 2r (0.70 g, 3.16 mmol) and phenyl isothiocyanate (0.47 g, 3.48 mmol) in THF (75 mL) was heated to reflux (3 h), and then the volatile materials were removed in vacuo. The residue was triturated with EtOH (15 mL), and the while solid material (0.70 g, 62%) that remained was filtered and recrystallized from absolute EtOH: mp 196°–197° C. (d); $R_f$ 0.65 (10% MeOH/CHCl$_3$); IR (KBr) 3400 (br, 3240 (br), 1620, 1470 (br), 1330, 750, 670 cm$^{-1}$; $^1$H NMR (DMSO-d$_6$) δ 1.89 (s, C(O)CH$_3$), 4.32 (d, J=5.8 Hz, CH$_2$), 5.24 (t, J=6.9 Hz, CH), 7.09–7.43 (m, 3ArH, 5PhH), 7.52–7.55 (m, 2ArH), 8.13 (d, J=6.9 Hz, NH), 8.55 (br s, NH), 8.85 (br, s, NH), 10.11 (s, NH); $^{13}$C NMR (DMSO-d$_6$) 22.22 (C(O)CH$_3$), 42.36 (CH$_2$), 61.18 (CH), 122.76 (2C$_2$), 124.29 (C$_4$), 126.53 (C$_{4'}$), 126.90 (2C$_{2'}$ or 2C$_{3'}$), 128.00 (2C$_{2'}$ or 2C$_{3'}$), 128.40 (2C$_3$), 138.94 (C$_1$ or C$_{1'}$), 139.01 (C$_1$ or C$_{1'}$), 167.82 (C(O)NH), 169.98 (C(O)CH$_3$), 180.02 (C(S)) ppm; mass spectrum (FD) 356 (M$^+$).

Anal. Calcd for C$_{18}$H$_{20}$N$_4$O$_2$S: C, 60.65; H, 5.66; N, 15.72. Found: C, 60.43; H, 5.70; N, 15.62.

EXAMPLE 103

Synthesis of N-[Acetamido(benzylcarbamoyl)methyl] phthalamic acid (2l).

To a warm pyridine solution (7.0 mL) containing 2r (0.63 g, 2.83 mmol), phthalic anhydride (0.43 g, 2.87 mmol) was added, and the reaction was stirred at 50°–55° C. (5 h). Pyridine was removed by distillation in vacuo and the residue was treated with H$_2$O (20 mL). The aqueous mixture was extracted with EtOAc (2×20 mL) and then acidified with aqueous 1N HCl solution. The white solid (0.70 g, 70%) that precipitated was filtered, washed with H$_2$O (10 mL), and dried: mp 186°–188° C.; $^1$H NMR (DMSO-d$_6$) δ 1.90 (s, C(O)CH$_3$), 4.36 (d, J=6.0 Hz, CH$_2$), 5.92 (t, J=7.2 Hz, CH), 7.20–7.31 (m, 5PhH), 7.43 (d, J=7.3 Hz, C$_6$H), 7.50–7.63 (m, C$_4$H, C$_5$H), 7.82 (d, J=7.3 Hz, C$_3$H), 8.41–8.48 (m, 2NH), 9.01 (d, J=7.2 Hz, NH), 13.30 (br s, CO$_2$H); $^{13}$C NMR (DMSO-d$_6$) 22.46 (C(O)CH$_3$), 42.39 (CH$_2$), 57.44 (CH), 126.57, 126.92, 127.81, 128.09, 128.72, 129.36, 129.85, 131.49, 137.78, 138.99 (ARC, PhC), 167.85, 167.93, 168.48, 169.47 (C(O)) ppm; mass spectrum (FD) 370 (M$^+$+1).

Anal. Calcd for C$_{19}$H$_{19}$N$_3$O$_5$: C, 61.78; H, 5.18; N, 11.38. Found: C, 61.63; H, 5.05; N, 11.16.

EXAMPLE 104

Synthesis of 2-Acetamido-N-benzyl-2-(N-succinimidyl) acetamide (2m).

A cooled (−78° C.) THF solution (150 mL) of 2s$^2$ (prepared from 2-acetamido-N-benzyl-2-ethoxyacetamide$^{4,5}$ (2.00 g, 8.0 mmol) and BBr$_3$ (2.51 g, 10.05 mmol)) was added slowly into a cooled (−78° C.) THF suspension (50 mL) of sodium succinimide (3.06 g, 25.25 mmol). The reaction mixture was stirred at −78° C. (30 min) and at room temperature (90 min), and then treated with a 10% aqueous citric acid solution (50 mL). The resulting solution was neutralized with a saturated aqueous NaHCO$_3$ solution, and the reaction mixture extracted with EtOAc (3×100 mL). The combined extracts were dried (Na$_2$SO$_4$), and the volatile materials were removed by distillation in vacuo. The residue was purified by flash column chromatography on SiO$_2$ gel (6% MeOH/CHCl$_3$) to give 1.10 g (45%) of 2m: mp 1.80°–183° C. (recrystallized from EtOH);

R$_f$ 0.26 (6% MeOH/CHCl$_3$); IR (KBr) 3340 (br), 1620 (br), 1480 (br), 1340, 780, 670 cm$^{-1}$; $^1$H NMR (DMSO-d$_6$) δ 1.90 (s, C(O)CH$_3$), 2.67 (s, CH$_2$CH$_2$), 4.23–4.36 (m, CH$_2$), 6.31 (d, J=9.0 Hz, CH), 7.17–7.35 (m, 5 PhH), 8.63 (t, J=5.9 Hz, NH), 8.72 (d, J=9.0 Hz, NH); $^{13}$C NMR (DMSO-d$_6$) 22.36 (C(O)CH$_3$), 27.99 (s, CH$_2$CH$_2$), 42.59 (CH$_2$), 55.19 (CH), 126.63 (C$_4$'), 126.96 (2C$_2$' or 2C$_3$'), 128.08 (2C$_2$' or 2C$_3$'), 138.91 (C$_1$'), 165.41 (C(O)NH), 169.86 (C(O)CH$_3$), 176.5 (C(O)CH$_2$CH$_2$C(O)) ppm; mass spectrum (FAB) 304 (M$^+$+1, 17), 163 (12), 155 (48), 152 (51), 135 (68), 119 (100).

Anal. Calcd for C$_{15}$H$_{17}$N$_3$O$_4$: C, 59.40; H, 5.65; N, 13.85. Found: C, 59.63; H, 5.70; N, 13.66.

EXAMPLE 105

Synthesis of Benzyl N-[Acetamido(benzylcarbamoyl)methyl]malonamate (2n).

4-Methylmorpholine (0.35 g, 3.56 mmol) was added to a solution of N-CBZ-glycine (0.74 g, 3.55 mmol) in THF (75 mL) at −10° to −15° C. The solution was stirred (5 min), and then isobutyl chloroformate (0.49 g, 3.55 mmol) was added and the mixture was stirred for an additional 20 min. A cooled (−10° C.) solution of 2r (0.79 g, 3.55 mmol) in THF (125 mL) was then added slowly (30 min). The reaction mixture was stirred at this temperature (2 h) and then at room temperature (2 h). The insoluble materials were filtered and the filtrate was concentrated in vacuo. The residue was triturated with EtOAc (20 mL) and the white solid (0.60 g) that remained was filtered, washed with H$_2$O and dried to give 2n. The initial insoluble material on trituration with H$_2$O gave an additional 0.40 g of 2n to give a combined yield of 1.00 g (68%); mp 177°–179° C. (recrystallized from EtOH); R$_f$ 0.46 (10% MeOH/CHCl$_3$); IR (KBr) 3400 (br), 3260, 1640 (br), 1540 (br), 1480, 1450, 1370, 760, 690 cm$^{-1}$; $^1$H NMR (DMSO-d$_6$) δ 1.86 (s, C(O)CH$_3$), 3.60–3.77 (m, C(O)CH$_2$NH), 4.28 (d, J=5.8 Hz, CH$_2$), 5.01 (s, OCH$_2$Ph), 5.79 (t, J=7.7 Hz, CH), 7.18–7.34 (m, 5 PhH, 5 ArH), 7.49 (t, J=5.8 Hz, NH), 8.43–8.55 (m, 3×NH); $^{13}$C NMR (DMSO-d$_6$) 22.36 (C(O)CH$_3$), 42.28 (CH$_2$), 43.39 (C(O)CH$_2$NH), 56.77 (CH), 65.42 (OCH$_2$Ph), 126.55 (2C), 126.94 (2C), 127.54, 127.66, 128.04 (2C), 128.22 (2C), 136.89, 138.96 (ArC, PhC), 156.40 (NHC(O)OCH$_2$Ph), 167.86 (NHC(O)CH$_2$), 168.96 (C(O)NH), 169.30 (C(O)CH$_3$) ppm; mass spectrum (FD) 413 (M$^+$+1, 100), 278 (75).

Anal. Calcd for C$_{21}$H$_{24}$N$_4$O$_5$: Found: C, 60.90; C, 61.16; H, 5.87; N, 1358.H, 5.77; N, 13.35.

EXAMPLE 106

Synthesis of Ethyl N-[Acetamido(benzylcarbamoyl)methyl] glycinate (2o).

A methanolic solution (70 mL) containing 2t (1.50 g, 4.28 mmol) and ethyl glycinate (prepared from ethyl glycinate hydrochloride (3.10 g, 22.2 mmol), NaOMe (1.17 g, 21.74 mmol)) was heated to reflux (2 h). The reaction was concentrated in vacuo to give an oily residue that was purified by flash column chromatography on SiO$_2$ gel (5% MeOH/CHCl$_3$) to give 0.60 g (46%) of 29o: mp 125°–127° C. (recrystallized from EtOAc); R$_f$ 0.43 (5% MeOH/CHCl$_3$); IR (KBr) 3400 (br), 3200, 1710, 1600, 1500, 1430, 1350, 740, 680 cm$^{-1}$; $^1$H NMR (DMSO-d$_6$) δ 1.17 (t, J=7.1 Hz, OCH$_2$CH$_3$), 1.86 (s, C(O)CH$_3$), 2.65–2.74 (m, NHCH$_2$C(O)), 3.26–3.33 (m, NHCH$_2$C(O)), 4.07 (q, J=7.1 Hz, OCH$_2$CH$_3$), 4.28 (d, J=5.8 Hz, CH$_2$), 5.01 (t, J=8.2 Hz, CH), 7.19–7.35 (m, 5 PhH), 8.25 (d, J=8.2 Hz, NH), 8.58 (t, J=5.8 Hz, NH); $^{13}$C NMR (DMSO-d$_6$) 13.98 (OCH$_2$CH$_3$), 22.46 (C(O)CH$_3$), 42.13 (CH$_2$), 46.22 (NHCH$_2$C(O)), 60.07 (OCH$_2$CH$_3$), 63.96 (CH), 126.67 (C$_4$'), 127.09 (2C$_2$' or 2C$_3$'), 128.13 (2C$_2$' or 2C$_3$'), 139.07 (C$_1$'), 169.07 (C(O)NH), 170.09 (C(O)CH$_3$), 171.56 (C(O)OCH$_2$CH$_3$) ppm; mass spectrum (FD) 342 (M$^+$).

Anal. Calcd for C$_{15}$H$_{21}$N$_3$O$_4$: C, 58.62; H, 6.89; N, 13.67. Found: C, 58.83; H, 7.00; N, 13.73.

EXAMPLE 107

Synthesis of Benzyl N-[Acetamido(benzylcarbamoyl)methyl]glycinate (2p).

A suspension of benzyl glycinate hydrochloride (5.00 g, 24.8 mmol) in THF (400 mL) containing Et$_3$N (4.90 g, 48.5 mmol) was stirred (4 h) at room temperature. The reaction mixture was cooled (−78° C.) and then a cooled (−78° C.) THF solution (150 mL) of 2s (prepared from 2-acetamido-N-benzyl-2-ethoxyacetamide (4.00 g, 16.0 mmol) and BBr$_3$ (1M in CH$_2$Cl$_2$, 20.0 mL, 20.0 mmol)) was added (30 min). The reaction mixture was stirred at −78° C. (30 min) and then at room temperature (16 h). The insoluble materials were filtered, the filtrate concentrated in vacuo, and the residue was purified by flash column chromatography on SiO$_2$ gel (3% MeOH/CHCl$_3$) to give 1.56 g (26%) of 2p as a white solid: mp 133°–135° C. (recrystallized from EtOH); R$_f$ 0.36 (3% MeOH/CHCl$_3$); IR (KBr) 3400, 3220, 1710, 1620, 1510, 1440, 1350, 740, 680 cm$^{-1}$; $^1$H NMR (DMSO-d$_6$) δ 1.85 (s, C(O)CH$_3$), 2.71–2.82 (m, NHCH$_2$C(O)), 3.39 (d, J=6.1 Hz, NHCHHC(O)), 3.40 (d, J=6.1 Hz, NHCHHC(O)), 4.27 (d, J=6.1 Hz, CH$_2$), 5.02 (t, J=8.2 Hz, CH), 5.11 (s, OCH$_2$Ph), 7.19–7.36 (m, 5 PhH, 5 ArH), 8.24 (d, J=8.2 Hz, NH), 8.57 (t, J=6.1 Hz, NH); $^{13}$C NMR (DMSO-d$_6$) 22.42 (C(O)CH$_3$), 42.11 (CH$_2$), 46.22 (NHCH$_2$C(O)), 63.94 (CH), 65.53 (OCH$_2$Ph), 126.62, 127.05 (2C), 127.80 (2C), 127.91, 128.08 (2C), 128.29 (2C), 135.87, 139.02 (ArC, PhC), 169.01 (C(O)NH), 170.06 (C(O)CH$_3$), 171.45 (C(O)OCH$_2$Ph) ppm; mass spectrum (FD) 370 (M$^+$+1).

Anal. Calcd for C$_{20}$H$_{23}$N$_3$O$_4$: C, 65.03; H, 6.28; N, 11.37. Found: C, 65.15; H, 6.53; N, 11.31.

EXAMPLE 108

Synthesis of N-[Acetamido(benzylcarbamoyl)methyl] glycine (2g).

A solution of methyl N-[acetamido(benzylcarbamoyl)methyl]glycinate (0.60 g, 2.05 mmol) and KOH (0.30 g, 5.36 mmol) in 90% aqueous EtOH (50 mL) was stirred at room temperature (48 h). The volatile materials were then removed in vacuo, and the residue dissolved in H$_2$O (10 mL). The aqueous solution was extracted with EtOAc (2×20 mL), and the aqueous layer was acidified to pH −2.0 with aqueous 1N HCl. A column containing ion exchange resin Dowex 50× W4 was prepared using 10% aqueous pyridine. The column was thoroughly washed with H$_2$O. The acidic aqueous reaction solution was added to the top of the column, and the column was eluted with H$_2$O (300 mL) or until the eluate was neutral. The column was then eluted with 10% aqueous pyridine (400 mL). The aqueous pyridine fraction was concentrated in vacuo to give a white solid, dried in vacuo, and then triturated with absolute EtOH (7 mL). The insoluble materials that remained were filtered and dried to give 0.29 g (50%) of 2q: mp 124°–126° C. (d); IR (KBr) 3400, 3200, 1630, 1500, 1370, 690 cm$^{-1}$; $^1$H NMR (DMSO-d$_6$) δ 1.84 (s, C(O)CH$_3$), 3.26 (s, CH$_2$C(O)), 4.29 (d, J=5.7 Hz, CH$_2$), 4.98 (d, J=8.2 Hz, CH), 7.21–7.33 (m, NH, 5 PhH), 8.39 (d, J=8.2 Hz, NH), 8.47 (t, J=5.7 Hz, NH); $^{13}$C NMR (DMSO-d$_6$) 22.41 (C(O)CH$_3$), 41.98 (CH$_2$), 47.48 (CH$_2$C(O)), 64.08 (CH), 126.75 (C$_4$'), 127.21 (2C$_2$' or 2C$_3$'), 128.24 (2C$_2$' or 2C$_3$'), 139.23 (C$_1$'), 169.91 (C(O)NH), 170.02 (C(O)CH$_3$), 170.20 (CH$_2$C(O) ppm.

Anal. Calcd for $C_{13}H_{17}N_3O_4$: C, 55.91; H, 6.13; N, 15.04. Found: C, 55.68; H, 6.06; N, 14.74.

EXAMPLE 109

Synthesis of 2-Acetamido-N-benzyl-2-(1-pyrrole) acetamide.

A cooled (−78° C.) THF solution (225 mL) of 2-acetamido-N-benzyl-2-bromoacetamide (prepared from 2-acetamido-N-benzyl-2-ethoxyacetamide (2.00 g, 8.0 mmol) and BBr$_3$ (1M CH$_2$Cl$_2$) solution, 8.8 mL, 8.8 mmol)) was added under N$_2$ a cooled (−78° C.) suspension of potassium pyrrole (2.71 g, 25.8 mmol) in THF (25 mL). The reaction mixture was stirred at −78° C. (1 h) and then at room temperature (1 h), and then treated with H$_2$O (10 mL) and acidified ("pH" 4.0) with 5% citric acid. The reaction was made basic with aqueous saturated Na$_2$CO$_3$ solution, and the aqueous mixture was extracted with EtOAc (2×250 mL) and the combined organic layers were dried (Na$_2$SO$_4$). The volatile materials were removed in vacuo and the residue was purified by flash column chromatography on SiO$_2$ gel using 3% MeOH/CHCl$_3$ as the eluant to give 0.40 g (18%) of the desired product. The compound X was purified by recrystallization from EtOH: mp 182°–184° C.; R$_f$ 0.44 (4% MeOH/CHCl$_3$); IR (KBr) 3400, 3280, 1630, 1520, 1370, 740, 720 cm$^{-1}$; $^1$H NMR (DMSO-d$_6$) δ 1.91 (s, C(O)CH$_3$), 4.30 (d, J=5.5 Hz, CH$_2$), 6.01 (s, 2×C$_3$H), 6.38 (d, J=8.7 Hz, CH), 6.85 (s, 2×C$_2$H), 7.11–7.35 (m, 5PhH), 8.96 (t, J=5.5 Hz, NH), 9.14 (d, J=8.7 Hz, NH); $^{13}$C NMR (DMSO-d$_6$) 22.22 (C(O)CH$_3$), 42.15 (CH$_2$), 62.86 (CH), 107.79 (2C$_3$), 119.19 (2C$_2$), 126.76 (C$_4$·), 127.01 (2C$_2$· or 2C$_3$·), 128.11 (2C$_2$·, or 2C$_3$·), 138.34 (C$_1$·), 166.37 (C(O)NH), 169.41 (C(O)CH$_3$) ppm; mass spectrum, m/e (relative intensity) 272 (M$^+$+1, 22), 271 (M$^+$, 100).

Anal. Calcd for $C_{15}H_{17}N_3O_2$·0.2 H$_2$O: C, 65.53; H, 6.37; N, 15.28. Found: C, 65.80; H, 6.22; N, 15.13.

EXAMPLE 110

Synthesis of 2-Acetamido-N-benzyl-2-(1-pyrazole) acetamide.

To a cooled (−78° C.) solution (250 mL) of 2-acetamido-N-benzyl-2-bromoacetamide (prepared from 2-acetamido-N-benzyl-2-ethoxyacetamide (3.60 g, 14.4 mmol) and BBr$_3$ (1M CH$_2$Cl$_2$ solution, 15.8 mL, 15.8 mmol)), a THF solution (20 mL) of Et$_3$N (2.91 g, 28.8 mmol) was added, followed by the addition of THF solution (30 mL) of pyrazole (1.17 g, 17.28 mmol). The mixture was stirred at −78° C. (30 min) and room temperature (1 h). The insoluble materials were filtered and the solvents removed in vacuo. The residue was purified by flash column chromatography on SiO$_2$ gel using 4% MeOH/CHCl$_3$ as the eluant to give 0.80 g (22%) of the desired product. The compound X was recrystallized from EtOAc as a white solid: mp 158°–160° C.; R$_f$ 0.51 (6% MeOH/CHCl$_3$); IR (KBr) 3400, 3180, 1650, 1530, 1470, 1370, 1350, 740, 700 cm$^{-1}$; $^1$H NMR (DMSO-d$_6$) δ 1.93 (s, C(O)CH$_3$), 4.29 (d, J=5.8 Hz, CH$_2$), 6.26 (s, C$_4$H), 6.57 (d, J=8.8 Hz, CH), 7.15–7.33 (m, 5PhH), 7.48 (br s, C$_5$H), 7.76 (br s, C$_3$H), 8.96 (t, J=5.8 Hz, NH), 9.23 (d, J=8.8 Hz, NH); $^{13}$C NMR (DMSO-d$_6$) 22.41 (C(O)CH$_3$), 42.40 (CH$_2$), 65.51 (CH), 105.37 (C$_4$), 126.87 (C$_4$·), 127.14 (2C$_2$· or 2C$_3$·), 128.25 (2C$_2$· or 2C$_3$·), 129.00 (C$_5$), 138.59 (C$_3$), 139.17 (C$_1$·), 165.68 (C(O)NH), 169.81 (C(O)CH$_3$) ppm; mass spectrum, m/e (relative intensity) 273 (M$^+$+1, 11), 272 (M$^+$, 2), 139 (83), 138 (100), 92 (37).

Anal. Calcd for $C_{14}H_{16}N_4O_2$: C, 61.75; H, 5.92; N, 20.57. Found: C, 61.95; H, 5.96; N, 20.28.

EXAMPLE 111

Synthesis of 2-Acetamido-N-benzyl-2-(1-imidazole) acetamide.

Using the preceeding procedure, 2-acetamido-N-benzyl-2-ethoxyacetamide (2.00 g, 8.0 mmol), BBr$_3$ (1M CH$_2$Cl$_2$ solution, 8.8 mL, 8.8 mmol), Et$_3$N (1.62 g, 1.60 mmol), and imidazole (0.60 g, 8.8 mmol) gave 0.60 g (30%) of the desired product. Compound X was recrystallized from ethyl acetate/hexane as a beige colored solid: mp 146°–148° C.; R$_f$ 0. (7% MeOH/CHCl$_3$); IR (KBr) 3400 (br), 1640, 1560, 1480, 1360, 720, 670 cm$^{-1}$; $^1$H NMR (DMSO-d$_6$) δ 1.85 (s, C(O)CH$_3$), 4.30 (br s, CH$_2$), 6.53 (d, J=8.0 Hz, CH), 6.89 (s, C$_5$H), 7.12–7.33 (m, C$_4$H, 5PhH), 7.69 (s, C$_2$H), 9.06 (br s, NH), 9.29 (d, J=8.0 Hz, NH); $^{13}$C NMR (DMSO-d$_6$) 22.28 (C(O)CH$_3$), 42.36 (CH$_2$) 61.18 (CH), 117.56 (C$_5$), 126.92 (C$_4$·), 127.16 (2C$_2$· or 2C$_3$·), 128.19 (C$_4$), 128.26 (2C$_2$· or 2C$_3$·), 136.21 (C$_2$), 138.27 (C$_1$·), 165.72 (C(O)NH), 169.77 (C(O)CH$_3$) ppm; mass spectrum, FD (relative intensity) 274 (M$^+$+2, 12), 273 (M$^+$+1, 77), 272 (100), 205 (34) 274 (18).

Anal. Calcd for $C_{14}H_{16}N_4O_2$: C, 61.75; H, 5.92; N, 20.57. Found: C, 61.95; H, 6.09; N, 20.32.

EXAMPLE 112

Synthesis of 2-Acetamido-N-benzyl-2-(1-(1,2,4-triazole)) acetamide.

Using 2-acetamido-N-benzyl-2-ethoxyacetamide (4.00 g, 16.0 mmol), BBr$_3$ (1M CH$_2$Cl$_2$ solution, 17.6 mL, 17.6 mmol), Et$_3$N (4.85 g, 48.0 mmol), and 1,2,4-triazole (1.43 g, 20.8 mmol), 1.20 g (28%) of the desired product was obtained. Compound X was recrystallized from EtOAc as an amorphous white solid: mp 146°–148° C.; R$_f$ 0.48 (6% MeOH/CHCl$_3$); IR (KBr) 3400, 1660, 1470, 1370, 830 cm$^{-1}$; $^1$H NMR (DMSO-d$_6$) δ 1.85 (s, C(O)CH$_3$), 4.32 (br s, CH$_2$), 6.70 (d, J=7.8 Hz, CH), 7.21–7.29 (m, 5PhH), 8.01 (s, C$_3$H), 8.57 (s, C$_5$H), 9.04 (br s, NH), 9.39 (d, J=7.8 Hz, NH); $^{13}$C NMR (DMSO-d$_6$) 22.39 (C(O)CH$_3$), 42.59 (CH$_2$), 65.02 (CH), 126.97 (C$_4$·), 127.25 (2C$_2$· or 2C$_3$·), 128.32 (2C$_2$· or 2C$_3$·), 138.47 (C$_1$·), 143.93 (C$_5$), 151.50 (C$_3$), 164.77 (C(O)NH), 170.23 (C(O)CH$_3$) ppm; mass spectrum, FD (relative intensity) 274 (M$^+$+1, 100), 273 (11), 205 (19), 204 (13), 140 (67), 139 (31).

Anal. Calcd for $C_{13}H_{15}N_5O_2$: C, 57.13; H, 5.53; N, 25.63. Found: C, 57.37; H, 5.66; N, 25.38.

EXAMPLE 113

Synthesis of 2-Acetamido-N-benzyl-2-(1-tetrazole)) acetamide.

Making use of 2-acetamido-N-benzyl-2-ethoxyacetamide (3.00 g, 12.0 mmol), BBr$_3$ (1M CH$_2$Cl$_2$ solution, 13.2 mL, 13.2 mmol), Et$_3$N (2.42 g, 24.0 mmol), and tetrazole (1.10 g, 15.6 mmol), 0.90 g (27%) of the desired product was obtained as a white solid. The compound X was recrystallized from EtOH: mp 169°–171° C.; R$_f$ 0.22 (4% MeOH/CHCl$_3$); IR (KBr) 3300 (br), 1660, 1510, 1360, 870, 740 cm$^{-1}$; $^1$H NMR (DMSO-d$_6$) δ 1.97 (s, C(O)CH$_3$), 4.25–4.40 (m, CH$_2$), 7.05 (d, J=8.4 Hz, CH), 7.21–7.38 (m, 5PhH), 9.23 (t, J=5.5 Hz, NH), 9.44 (s, C$_5$H), 9.69 (d, J=8.4 Hz, NH); $^{13}$C NMR (DMSO-d$_6$) 22.38 (C(O)CH$_3$), 42.78 (CH$_2$), 63.62 (CH), 127.10 (C$_4$·), 127.39 (2C$_2$· or 2C$_3$·), 128.38 (2C$_2$· or 2C$_3$·), 138.26 (C$_1$·), 143.67 (C$_5$), 163.88 (C(O)NH), 170.62 (C(O)CH$_3$) ppm; mass spectrum, FD (relative intensity) 275 (M$^+$, 79), 273 (14), 206 (100), 205 (50).

Anal. Calcd for $C_{12}H_{14}N_6O_2$: C, 52.55; H, 5.15; N, 30.64. Found: C, 52.75; H, 5.33; N, 30.64.

EXAMPLE 114

Synthesis of α-Acetamido-N-benzyl-1-(dimethylsulfamoyl) imidazole-4-acetamide.

To a cooled (−78° C.) THF solution (150 mL) of 2-acetamido-N-benzyl-2-bromoacetamide (prepared from 2-acetamido-N-benzyl-2-ethoxyacetamide (2.00 g, 8.0 mmol) and BBr$_3$ (1M solution in CH$_2$Cl$_2$, 9.0 mL, 9.0 mmol)) was added Et$_3$N (1.62 g, 16.0 mmol), and then a THF solution of the 2-lithio salt of N,N-dimethylimidazole-1-sulfonamide (generated by the addition of n-BuLi (2.5M in hexane, 3.9 mL, 9.68 mmol) into a cooled (−78° C.) THF solution (25 mL) of N,N-dimethylimidazole-1-sulfonamide (1.54 g, 8.8 mmol)) was added during a 15 min interval. The reaction mixture was stirred at this temperature (30 min) and then at room temperature (45 min). A saturated aqueous NH$_4$Cl solution (50 mL) and H$_2$O (50 mL) were then sucessively added to the reaction, and the aqueous mixture was extracted with EtOAc (3×50 mL). The combined extracts were dried (Na$_2$SO$_4$), and the volatile materials were removed by distillation in vacuo. The residue was purified by flash column chromatography on SiO$_2$ gel (4% MeOH/CHCl$_3$) to give 0.50 g (17%) of the desired product: mp 145°–147° C. (recrystallized from EtOAc/hexane); R$_f$ 0.35 (4% MeOH/CHCl$_3$); IR (KBr) 3400, 1640, 1530, 1380, 720 cm$^{-1}$; $^1$H NMR (DMSO-d$_6$) δ 1.96 (s, C(O)CH$_3$), 2.77 (s, N(CH$_3$)$_2$), 4.25 (dd, J=6.0, 15.5 Hz, CHH), 4.34 (dd, J=6.0, 15.5 Hz, CHH), 5.43 (d, J=8.0, Hz, CH), 7.19–7.30 (m, 5 PhH), 7.40 (s, C$_5$H), 8.17 (s, C$_2$H), 8.42 (d, J=8.0 Hz, NH), 8.67 (t, J=6.0 Hz, NH); $^{13}$C NMR (DMSO-d$_6$) 22.42 (C(O)CH$_3$), 37.80 (N(CH$_3$)$_2$), 42.11 (CH$_2$), 51.40 (CH), 115.50 (C$_5$), 126.64 (C$_4$·), 126.94 (2C$_2$· or 2C$_3$·), 128.12 (2C$_2$· or 2C$_3$·), 136.70 (C$_2$), 139.17 (C$_1$·), 140.26 (C$_4$), 168.93 (C(O)NH), 169.09 (C(O)CH$_3$) ppm; mass spectrum (FD) 380 (M$^+$+1, 34), 248 (13), 247 (100), 108 (64).

Anal. Calcd for C$_{16}$H$_{21}$N$_5$O$_4$S: C, 50.65; H, 5.58; N, 17.87. Found: C, 51.92; H, 5.65; N, 18.09.

EXAMPLE 115

Synthesis of α-Acetamido-N-benzyl-4-imidazole acetamide.

A 75% aqueous EtOH (16 mL) solution of α-acetamido-N-benzyl-1-(N,N-dimethylsulfamido)imidazole-4-acetamide (0.85 g, 3.05 mmol) was acidified ("pH" ~1.5) with ethanolic HCl, and the solution was heated to reflux (8 h). The reaction was neutralized with a saturated aqueous NaHCO$_3$ solution and the EtOH-H$_2$O azeotrope removed by distillation in vacuo. The remaining aqueous layer was made basic ("pH" 10) with aqueous NaOH. The aqueous mixture was extracted with EtOAc (3×50 mL) and the combined extracts were dried (Na$_2$SO$_4$). The reaction was concentrated in vacuo to give 0.35 g (57%) of the desired product: mp 189°–191° C. (d) (recrystallized from acetone); R$_f$ 0.19 (10% MeOH/CHCl$_3$); IR (KBr) 3400, 3260, 1650, 1600, 1500, 1430, 1360, 1330, 730, 710 cm$^{-1}$; $^1$H NMR (DMSO-d$_6$) δ 1.88 (s, C(O)CH$_3$), 4.28 (d, J=5.9 Hz, CH$_2$), 5.38 (d, J=6.8 Hz, CH), 5.38 (br s, C$_5$H), 7.15–7.30 (m, 5 PhH), 7.60 (s, C$_2$H), 8.26 (br s, NH), 8.53 (br s, NH), 12.01 (br s, NH) ppm; mass spectrum (FD) 273 (M$^+$+1).

Anal. Calcd for C$_{14}$H$_{16}$N$_4$O$_2$: C, 61.75; H, 5.92; N, 20.58. Found: C, 61.59; H, 5.98; N, 20.37.

EXAMPLE 116

Synthesis of α-Acetamido-N-benzyl-2-imidazole acetamide.
Preparation or 1-diethoxymethyl-2-lithioimidazole.

n-BuLi (2.5M in hexane, 6.8 mL, 17.0 mmol) was added to a cooled (−46° C.) solution of 1-diethoxymethylimidazole (2.90 g, 17.06 mmol) in THF (45 mL) under N$_2$ atm. The solution was stirred at −46° C. (15 min) to give the desired product.

Preparation of α-Acetamido-N-benzyl-2-imidazoleacetamide.

The 2-lithio salt solution of 1-diethoxymethylimidazole was added dropwise (15 min) into a cooled (−78° C.) THF solution (130 mL) of 2-acetamido-N-benzyl-2-bromoacetamide (prepared from 2-acetamido-N-benzyl-2-ethoxyacetamide (2.00 g, 8.0 mmol) and BBr$_3$ (1M in CH$_2$Cl$_2$, 10 mL, 10.0 mmol)). The reaction was stirred at −78° C. (1 h) and then quenched with a saturated aqueous NH$_4$Cl (50 mL) solution. The mixture was stirred at room temperature (30 min), and made basic ("pH" 9.2)by adding aqueous K$_2$CO$_3$. The aqueous mixture was extracted with EtOAc (3×100 mL), and the combined extracts were dried (Na$_2$SO$_4$). The solvents were removed in vacuo and the residue was purified by flash column chromatography on SiO$_2$ gel (2.5% MeOH/CHCl$_3$) to give 0.14 g (7%) of the desired product: mp 228°–230° C. (recrystallized from EtOH); R$_f$ 0.46 (10% MeOH/CHCl$_3$); IR (KBr) 3200 (br), 1610, 1500 (br), 1430, 1350, 740, 680 cm$^{-1}$; $^1$H NMR (DMSO-d$_6$) δ 1.91 (s, C(O)CH$_3$), 4.29 (d, J=5.6 Hz, CH$_2$), 5.51 (d, J=7.7 Hz, CH), 6.85 (br s, C$_4$H), 7.05 (br s, C$_5$H), 7.18–7.30 (m, 5 PhH), 8.42 (d, J=7.7 Hz, NH), 8.65 (t, J=5.6 Hz, NH), 11.91 (br s, NH); $^{13}$C NMR (DMSO-d$_6$) 22.49 (C(O)CH$_3$), 42.21 (CH$_2$), 51.62 (CH), 126.60 (C$_4$·), 126.98 (2C$_2$· or 2C$_3$·), 127.21 (C$_4$), 128.09 (2C$_2$· or 2C$_3$·), 128.32 (C$_5$), 139.05 (C$_1$·), 143.74 (C$_2$), 168.12 (C(O)NH), 169.30 (C(O)CH$_3$) ppm; mass spectrum (FD) 273 (M$^+$+1, 65), 272 (M$^+$, 100).

Anal. Calcd for C$_{14}$H$_{16}$N$_4$O$_2$: C, 61.75; H, 5.92; N, 20.58. Found: C, 61.56; H, 5.92; N, 20.37.

EXAMPLE 117

Synthesis of α-Acetamido-N-benzyl-5-(tetrazole) acetamide.

A mixture of (2-acetamido-N-benzyl-2-cyanoacetamide (1.00 g, 4.33 mmol), potassium azide (1.70 g, 20.96 mmol) and Et$_3$N.HCl (1.78 g, 13.0 mmol) in 1-methyl-2-pyrrolidinone (1.25 mL) was stirred at 110° C. (7 h). After cooling, aqueous concentrated HCl (1 mL) was added, and the reaction mixture was filtered. The solvent was removed in vacuo. The residue was dissolved in aqueous 1N NaOH (20 mL), and then aqueous 1N HCl (20 mL) was added. The precipitate was filtered to give 0.77 g (65%) of the desired product. The compound X was recrystallized from EtOH: mp 236°–238° C.; R$_f$ 0.20 (30% MeOH/CHCl$_3$); $^1$H NMR (DMSO-d$_6$) δ 1.94 (s, C(O)CH$_3$), 4.33 (d, J=5.7 Hz, CH$_2$), 5.89 (d, J=7.8 Hz, CH), 7.18–7.33 (m, 5 PhH), 8.86 (d, J=7.8 Hz, NH), 8.92 (t, J=5.7 Hz, NH), 16.54 (br s, NH); $^{13}$C NMR (DMSO-d$_6$) 22.21 (C(O)CH$_3$), 42.37 (CH$_2$), 48.13 (CH), 126.67 (C$_4$·), 127.00 (2C$_2$· or 2C$_3$·), 128.05 (2C$_2$· or 2C$_3$·), 138.52 (C$_1$·), 166.18 (C(O)NH), 169.58 (C(O)CH$_3$) ppm; mass spectrum, FD (relative intensity) 275 (M$^+$+1, 73), 274 (100). M$_r$ (+CI) 274.119201 (calcd for C$_{12}$H$_{14}$N$_6$O$_2$: 274.117824.

EXAMPLE 118

Synthesis of α-Acetamido-N-benzyl-3-(1,2,4-triazole) acetamide.

An ethanolic solution (250 mL) of 2-acetamido-N-benzyl-2-cyanoacetamide (3.00 g, 13.0 mmol), formic hydrazide (1.60 g, 26.0 mmol) and K$_2$CO$_3$ (6.00 g, 2.90 mmol) was heated at reflux (20 h). The reaction mixture was allowed to cool, filtered, and the solvent was removed in vacuo. The residue was purified by flash column chromatography on SiO$_2$ gel using 13% MeOH/CHCl$_3$ as the eluant to give 1.40 g (40%) of the desired product. The compound X was purified by recrystallization from EtOH: mp 205°–207° C.; $R_f$ 0.35 (16% MeOH/CHCl$_3$); $^1$H NMR (DMSO-d$_6$) δ 1.92 (s, C(O)CH$_3$), 4.30 (d, J=5.7 Hz, CH$_2$), 5.62 (d, J=7.8 Hz, CH), 7.18–7.32 (m, 5 PhH), 8.53 (s, C$_5$H), 8.56 (d, J=7.8 Hz, NH), 8.71 (t, J=5.7 Hz, NH), 13.98 (s, NH); $^{13}$C NMR (DMSO-d$_6$) 22.48 (C(O)CH$_3$), 42.41 (CH$_2$), 51.30 (CH), 126.63 (C$_{4'}$), 127.08 (2C$_{2'}$ or 2C$_{3'}$), 128.11 (2C$_{2'}$ or 2C$_{3'}$), 139.05 (C$_{1'}$), 167.92 (C(O)NH), 169.32 (C(O)CH$_3$); ppm; mass spectrum, FD (relative intensity) 274 (M$^+$+1, 100), 273 (66).

Anal. Calcd for C$_{13}$H$_{15}$N$_5$O$_2$: C, 57.13; H, 5.53; N, 25.63. Found: C, 57.32; H, 5.57; N, 25.53.

EXAMPLE 119

Synthesis of α-Acetamido-N-benzyl-2-(carboxamide oxime)acetamide.

A suspension of NH$_2$OH.HCl (1.80 g, 25.9 mmol), K$_2$CO$_3$ (4.85 g, 35.0 mmol), 2-acetamido-N-benzyl-2-cyanoacetamide (2.00 g, 8.65 mmol) in absolute EtOH (150 mL) was heated at reflux (16 h). The reaction mixture was cooled, filtered, and concentrated under vacuum. The residue was purified by flash column chromatography on SiO$_2$ gel using 8% MeOH/CHCl$_3$ as the eluant to give 1.24 g (54%) of the desired product. The compound X was further purified by recrystallization from ethyl acetate/hexane: mp 172°–173° C.; $R_f$ 0.40 (10% MeOH/CHCl$_3$); $^1$H NMR (DMSO-d$_6$) δ 1.87 (s, C(O)CH$_3$), 4.27 (d, J=6.0 Hz, CH$_2$), 4.88 (d, J=8.4 Hz, CH), 5.37 (s, NH$_2$), 7.21–7.30 (m, 5 PhH), 8.21 (d, J=8.4 Hz, NH), 8.48 (t, J=6.0 Hz, NH), 9.28 (s, OH); $^{13}$C NMR (DMSO-d$_6$) 22.46 (C(O)CH$_3$), 42.15 (CH$_2$), 53.65 (CH), 126.60 (C$_{4'}$), 126.99 (2C$_{2'}$ or 2C$_{3'}$), 128.108 (2C$_{2'}$ or 2C$_{3'}$), 139.02 (C$_{1'}$), 149.63 (CNH$_2$), 167.88 (C(O)NH), 169.07 (C(O)CH$_3$) ppm; mass spectrum, FD (relative intensity) 265 (M$^+$+1, 36), 264 (100).

Anal. Calcd for C$_{12}$H$_{16}$N$_4$O$_3$: C, 54.54; H, 6.10; N, 21.20. Found: C, 54.81; H, 6.01; N, 21.41.

EXAMPLE 120

Synthesis of α-Acetamido-N-benzyl-2-(carboxamide oxime-(O-acetate))acetamide.

To a stirred solution of α-acetamido-N-benzyl-2-(carboxamide oxime)acetamide (0.72 g, 7.25 mmol) in pyridine (8 mL), acetyl chloride (0.25 mL, X mmol) was added dropwise. Upon addition of the acetyl chloride a small exotherm was detected (25° C. to 37° C.). The reaction mixture was stirred at room temperature (1 h). The solvent was then removed in vacuo, and the residue was dissolved in CH$_2$Cl$_2$ (100 mL). The solution was washed with an aqueous 0.5N HCl solution (20 mL). The organic phase was dried (Na$_2$SO$_4$), and the solvent was removed in vacuo to give 0.60 g (72%) of the desired product. The compound X was recrystallized from chloroform/hexane: mp 131°–133° C.; $R_f$ 0.35 (4% MeOH/CHCl$_3$); $^1$H NMR (DMSO-d$_6$) δ 1.90 (s, C(O)CH$_3$), 2.06 (s, OC(O)CH$_3$), 4.29 (t, J=5.3 Hz, CH$_2$), 5.00 (d, J=8.4 Hz, CH), 6.48 (br s, NH$_2$), 7.19–7.33 (m, 5 PhH), 8.29 (d, J=8.4 Hz, NH), 8.66 (t, J=5.3 Hz, NH); $^{13}$C NMR (DMSO-d$_6$) 19.86 (OC(O)CH$_3$), 22.77 (C(O)CH$_3$), 42.50 (CH$_2$), 53.45 (CH), 126.89 (C$_{4'}$), 127.28 (2C$_{2'}$ or 2C$_{3'}$), 128.38 (2C$_{2'}$ or 2C$_{3'}$), 139.00 (C$_{1'}$), 156.13 (CNH$_2$), 167.19 (C(O)NH), 168.49 (OC(O)CH$_3$), 169.55 (C(O)CH$_3$) ppm; mass spectrum, FD (relative intensity) 307 (M$^+$+1, 100), 306 (43).

Anal. Calcd for C$_{14}$H$_{18}$N$_4$O$_4$: C, 54.89; H, 5.92; N, 18.29. Found: C, 54.86; H, 5.84; N, 18.19.

EXAMPLE 121

Synthesis of α-Acetamido-N-benzyl-3-(1,2,4-oxadiazole)acetamide.

α-Acetamido-N-benzyl-2-(carboxamide oxime) acetamide (0.90 g, 3.4 mmol) was dissolved in trimethylorthoformate (10 mL) containing BF3.Et$_2$O (6 drops). The solution was warmed to 55° C. (20 min), and then evaporated under reduced pressure to give a white-blue solid. The material was dissolved in MeOH and treated with norit, filtered, and evaporated under reduced pressure to furnish crude product (0.79 g, 85%). The compound was purified by recrystallization from chloroform/hexane: mp 164°–166° C.; $R_f$ 0.37 (6% MeOH/CHCl$_3$); $^1$H NMR (DMSO-d$_6$) δ 1.92 (s, C(O)CH$_3$), 4.31 (d, J=6.0 Hz, CH$_2$), 5.82 (d, J=8.4 Hz, CH), 7.15–7.34 (m, 5 PhH), 8.88 (d, J=8.4 Hz, NH), 8.96 (t, J=6.0 Hz, NH), 9.62 (s, C$_5$H); $^{13}$C NMR (DMSO-d$_6$) 22.22 (C(O)CH$_3$), 42.35 (CH$_2$), 49.44 (CH), 126.77 (C$_{4'}$), 127.06 (2C$_{2'}$ or 2C$_{3'}$), 128.18 (2C$_{2'}$ or 2C$_{3'}$), 138.70 (C$_{1'}$), 166.25 (C(O)NH), 166.74 (C$_3$), 167.24 (C(O)CH$_3$), 169.52 (C$_5$, CH) ppm; mass spectrum, FD (relative intensity) 275 (M$^+$+1, 28), 274 (100).

Anal. Calcd for C$_{13}$H$_{14}$N$_4$O$_3$: C, 56.93; H, 5.14; N, 20.43. Found: C, 56.65; H, 5.01; N, 20.28.

EXAMPLE 122

Synthesis of α-Acetamido-N-benzyl-2-(thioamide) acetamide.

2-Acetamido-N-benzyl-2-cyanoacetamide (4.00 g, 34.64 mmol) and O,O-diethyldithiophosphoric acid (6.45 g, 34.64 mmol) were dissolved in a binary MeOH (80 mL)-EtOH (80 mL) solution containing H$_2$O (0.32 mL) and heated at 70° C. (6 h) and then allowed to remain at room temperature (13 h). The reaction mixture was filtered, and the solvent was removed in vacuo. The residue was triturated with EtOAc to give 2.00 g (44%) of the desired compound. The thioamide was recrystallized from ethyl acetate/hexane: mp 170°–171° C.; $R_f$ 0.51 (8% MeOH/CHCl$_3$); $^1$H NMR (DMSO-d$_6$) δ 1.93 (s, C(O)CH$_3$), 4.29 (d, J=5.0 Hz, CH$_2$), 5.21 (d, J=8.0 Hz, CH), 7.15–7.31 (m, 5 PhH), 8.03 (d, J=8.0 Hz, NH), 8.69 (t, J=5.0 Hz, NH), 9.27 (s, NHH'), 9.91 (s, NHH); $^{13}$C NMR (DMSO-d$_6$) 22.68 (C(O)CH$_3$), 42.24 (CH$_2$), 62.95 (CH), 126.63 (C$_{4'}$), 126.96 (2C$_{2'}$ or 2C$_{3'}$), 128.087 (2C$_{2'}$ or 2C$_{3'}$), 138.83 (C$_{1'}$), 166.42 (C(O)NH), 169.10 (C(O)CH$_3$), 200.28 (C(S)NH$_2$) ppm; mass spectrum, FD (relative intensity) 266 (M$^+$+1, 42), 265 (100).

Anal. Calcd for C$_{12}$H$_{15}$N$_3$O$_2$S: C, 54.32; H, 5.70; N, 15.84. Found: C, 54.44; H, 5.74; N, 15.54.

EXAMPLE 123

Synthesis of Ethyl 2-Acetamido-2-vinylacetate.

Vinyl magnesium bromide (10.9 mL, 1N, 10.9 mmol) was slowly added to a cooled (−78° C.) solution of ethyl 2-acetamido-2-bromoacetate (1.10 g, 4.91 mmol) in THF (50 mL). The reaction was stirred at −78° C. (2 h), and was then quenched with a 1N citric acid solution (7.0 mL). The mixture was allowed to warm to room temperature, and then the THF was removed in vacuo. The aqueous mixture was extracted with CHCl$_3$ (3×100 mL), and the combined CHCl$_3$ extracts were dried (Na$_2$SO$_4$) and concentrated to dryness. The residue was purified by flash chromatography using SiO$_2$ gel and 2% MeOH/CHCl$_3$ as the eluant to give 0.50 g (60%) of the desired product as a light yellow colored oil: $R_f$ 0.51 (4% MeOH/CHCl$_3$); $^1$H NMR (DMSO-d$_6$) δ 1.17 (t, J=7.1 Hz, OCH$_2$CH$_3$), 1.88 (s, C(O)CH$_3$), 4.09 (d, J=7.1 Hz, OCH$_2$CH$_3$), 4.80–4.86 (m, α-CH), 5.22–5.35 (m, CH=CH$_2$), 5.82–5.92 (m, CH=CH$_2$), 8.47 (d, J=7.4 Hz, NH); $^{13}$C NMR (DMSO-d$_6$) 13.96 (OCH$_2$CH$_3$), 22.12 (C(O)CH$_3$), 54.65 (α-CH), 60.71 (OCH$_2$CH$_3$), 117.89 (CH=CH$_2$), 132.48 (CH=CH$_2$), 169.16 (C(O)CH$_3$), 170.26 (C(O)NH) ppm.

EXAMPLE 124

Synthesis of Vinyl Glycine.

A mixture of ethyl 2-acetamido-2-vinyl acetate (5.20 g, 30.40 mmol) and aqueous 6N HCl (200 mL) was heated to reflux (2 h). The mixture was cooled to room temperature, and then extracted with $CHCl_3$ (3×100 mL). The aqueous solution which was dark brown in color was decolorized with norit (15 min) at. 60° C., and then the mixture was filtered, and the filtrate was concentrated to dryness to give aude vinyl glycine hydrochloride. The salt was dissolved in a minimum amount of $H_2O$ and acidified to pH 2.0 with aqueous 1N HCl. The solution was applied to an ion exchange resin (Dowex 50XW4, ammonium form) and eluted with $H_2O$ until the eluate was neutral. The ion exchange column was then eluted with an aqueous 1N $NH_4OH$ solution (~500 mL). Removal of volatile materials from the $NH_4OH$ eluate gave 1.80 g (60%) of vinyl glycine: mp 218°–220° C. (d); $^1H$ NMR ($D_2O$) δ 4.09 (d, J=7.2 Hz, α-CH), 5.28–5.35 (m, CH=$CH_2$), 5.80–5.87 (m, CH=$CH_2$).

EXAMPLE 125

Synthesis of 2-Acetamido-2-vinylacetic acid.

Acetic anhydride (2.50 g, 24.50 mmol) was added slowly into a cooled (–10° C.) solution of vinyl glycine (2.20 g, 21.78 mmol) in AcOH (100 mL). The mixture was stirred at this temperature (30 min) and then at room temperature (3 h). The solution was concentrated repeatedly from $H_2O$. The residue was dissolved in absolute EtOH (200 mL) and then decolorized (norit, 60° C.), and filtered. The filtrate was concentrated in vacuo, and the residue was triturated with $Et_2O$ to give 1.70 g (55%) of the desired product as a low melting yellow solid: $^1H$ NMR (DMSO-$d_6$) δ 1.87 (s, C(O)$CH_3$), 4.75 (dd, J=6.2, 7.5 Hz, α-CH), 5.13–5.27 (m, CH=$CH_2$), 5.84–5.96 (m, CH=$CH_2$), 8.24 (d, J=7.5 Hz, NH).

EXAMPLE 126

Synthesis of 2-Acetamido-N-benzyl-2-vinylacetamide.

4-Methylmorpholine (0.71 g, 6.99 mmol) was added to a suspension of 2-acetamido-2-vinylacetic acid (1.00 g, 6.99 mmol) in THF (325 mL), and the mixture was stirred at room temperature (30 min). The reaction was cooled to –10° to –15° C. and then isobutylchloroformate (1.24 g, 9.08 mmol) was then added dropwise. After stirring (10 min), a solution of benzylamine (0.75 g, 6.99 mmol) in THF (25 mL) was added (15 min). The reaction mixture was allowed to warm to 0° C. The insoluble material was filtered. The filtrate was concentrated in vacuo, and the residue was purified by flash column chromatography on $SiO_2$ gel using 3% MeOH/$CHCl_3$ as the eluant to give 1.00 g (62%) of the desired product: mp 136°–138° C. (recrystallized from EtOAc); $R_f$ 0.24 (3% MeOH/$CHCl_3$); $^1H$ NMR (DMSO-$d_6$) δ 1.88 (s, C(O)$CH_3$), 4.27 (d, J=5.6 Hz, $CH_2$), 4.89–4.94 (dd, J=6.4, 7.8 Hz, α-CH), 5.13–5.30 (m, —CH=$CH_2$), 5.81–5.93 (m, —CH=$CH_2$), 7.20–7.33 (m, 5 PhH), 8.27 (c, J=7.8 Hz, NH), 8.58 (t, J=5.6 Hz, NH); $^{13}C$ NMR (DMSO-$d_6$) 22.47 (C(O)$CH_3$), 42.05 ($CH_2$), 55.24 (α-CH), 116.44 (CH=$CH_2$), 126.74 ($C_{4'}$), 127.05 ($2C_{2'}$ or $2C_{3'}$), 128.24 ($2C_{2'}$ or $2C_{3'}$), 134.76 (CH=$CH_2$), 139.25 ($C_{1'}$), 168.78 (C(O)$CH_3$), 168.99 (C(O)NH) ppm.

EXAMPLE 127

Synthesis of 2-Acetamido-N-benzyl-2-epoxyacetamide.

A solution of 2-acetamido-N-benzyl-2-vinylacetamide (1.00 g, 4.31 mmol) and m-chloroperoxybenzoic acid (1.76 g, 55%, 5.60 mmol) in dichloromethane (100 mL) was stirred at room temperature (24 h), and then heated at reflux (3 h). The reaction solution was treated with a saturated aqueous $Na_2SO_3$ solution (20 mL) and then the organic layer was extracted with a saturated aqueous $NaHCO_3$ solution (3×50 mL). The organic layer was washed with a saturated aqueous NaCl solution and dried ($Na_2SO_4$). The $CH_2Cl_2$ was removed in vacuo, and the residue was then purified by flash column chromatography on $SiO_2$ gel using 4% MeOH/EtOAc as the eluant to give 0.35 g (33%) of the desired product: mp °C. (recrystallized from EtOAc); $R_f$ 0.48 (5% MeOH/$CHCl_3$); $^1H$ NMR (DMSO-$d_6$) δ 1.87 (s, C(O)$CH_3$), 2.66 (dd, J=2.5, 5.0 Hz, CH(O)CHH), 2.75 (dd, J=4.3, 5.0 Hz, CH(O)CHH), 3.20 (m, CH(O)CHH), 4.25–4.32 (m, α-CH, $CH_2$), 7.21–7.34 (m, 5 PhH), 8.30 (d, J=8.1 Hz, NH), 8.59 (t, J=5.8 Hz, NH); $^{13}C$ NMR (DMSO-$d_6$) 22.18 (C(O)$CH_3$), 41.99 ($CH_2$), 43.91 (CH(O)$CH_2$), 51.30 (CH(O)$CH_2$), 53.80 (α-CH), 126.49 ($C_{4'}$), 126.83 ($2C_{2'}$ or $2C_{3'}$), 127.98 ($2C_{2'}$ or $2C_{3'}$), 138.86 ($C_{1'}$), 168.52 (C(O)NH), 169.24 (C(O)$CH_3$) ppm.

EXAMPLE 128

Synthesis of Potassium 2-Acetamido-N-benzylacetamide-2-sulfonate.

A solution of 2-acetamido-N-benzyl-2-(trimethylammonium)acetamide tetrafluoroborate (0.30 g, 0.85 mmol) and $K_2SO_3$ (0.68 g, 4.26 mmol) in $H_2O$ (7.0 mL) was heated at 50°–55° C. (4 h). The solution was evaporated to dryness, and the residue was extracted with hot MeOH (3×10 mL). The MeOH was removed in vacuo to give a white solid (~30 mg): $^1H$ NMR ($D_2O$) δ 1.97 (s, C(O)$CH_3$), 4.33 ($CH_2$), 5.45 (CH), 7.19–7.28 (m, 5 PhH); $^{13}C$ NMR ($D_2O$) 22.00 (C(O)$CH_3$), 43.41 ($CH_2$), 67.77 (CH), 127.18 ($2C_{2'}$ or $2C_{3'}$), 127.53 ($C_{4'}$), 128.83 ($2C_{2'}$ or $2C_{3'}$), 137.58 ($C_{1'}$), 166.02 (C(O)NH), 173.65 (C(O)$CH_3$) ppm.

EXAMPLE 129

Synthesis of Ethyl 2-Acetamido-4-pentenoic acid ester.

Allyltrimethylsilane (4.09 g, 31.40 mmol) was added to a stirred solution of ethyl 2-acetamido-2-bromoacetate (1.76 g, 7.86 mmol) in dry THF (90 mL). After stirring (5 min), an ethereal solution of $ZnCl_2$ (1N, 12.2 mL, 12.2 mmol) was added and the stirring was continued (70 h). The THF was removed by distillation in vacuo and the residue that remained was treated with $H_2O$ (50 mL). The aqueous mixture was extracted with $CH_2Cl_2$ (3×75 mL), the combined extract was dried ($Na_2SO_4$) and concentrated to give 1.40 g (97%) of the desired product. The ester was purified by distillation in vacuo (65°–70° C., 0.3–0.8 torr) to give the desired product as a colorless oil: $R_f$ 0.35 (3% MeOH/$CHCl_3$); $^1H$ NMR ($CDCl_3$) δ 1.25 (t, J=6.8 Hz, O$CH_2CH_3$), 1.99 (s, C(O)$CH_3$), 2.44–2.60 (m, $CH_2$CH=$CH_2$), 4.17 (q, J=6.8 Hz, O$CH_2CH_3$), 4.60–4.66 (m, CH), 5.07–5.11 (m, $CH_2$CH=$CH_2$), 5.59–5.70 (m, $CH_2$CH=$CH_2$), 6.15 (br s, NH); $^{13}C$ NMR ($CDCl_3$) 14.09 (OCH$_2CH_3$), 23.00 (C(O)$CH_3$), 36.46 ($CH_2$CH=$CH_2$), 51.58 (CH), 61.39 (O$CH_2$$CH_3$), 118.95 ($CH_2$CH=$CH_2$), 132.15 ($CH_2$CH=$CH_2$), 169.64 (C(O)$CH_3$), 171.74 (C(O)O$CH_2CH_3$) ppm; mass spectrum, m/e (relative intensity) 186 ($M^+$+1, 2), 144 (19), 126 (7), 112 (31), 102 (73), 87 (18), 71 (100), 70 (89).

EXAMPLE 130

Synthesis of 2-Acetamido-4-pentenoic acid.

Ethyl 2-acetamido-4-pentenoic acid ester (1.20 g, 6.50 mmol) was dissolved in 90:5 EtOH:$H_2O$ (40 mL), and then KOH (1.50 g, 26.80 mmol) was added and the resulting solution stirred at room temperature (48 h). The reaction was concentrated in vacuo and the residue diluted with $H_2O$ (15 mL) and then washed with $Et_2O$ (2×30 mL). The aqueous layer was then made acidic with 8.5% $H_3PO_4$ and extracted with EtOAc (3×75 mL). The combined organic layers were dried ($Na_2SO_4$), and evaporated in vacuo to give 0.56 g (55%) of the desired product: mp 113°–115° C. (recrystallized from EtOAc); $^1H$ NMR (DMSO-$d_6$) δ 2.00 (C(O)CH$_3$), 2.43–2.65 (m, CH$_2$CH=CH$_2$), 4.36–4.43 (m, CH), 5.19–5.30 (m, CH$_2$CH=CH$_2$), 5.84–5.98 (m, CH$_2$CH=CH$_2$), 8.29 (d, J=7.7 Hz, NH), 12.78 (br s, OH); $^{13}C$ NMR (DMSO-$d_6$) 22.35 (C(O)CH$_3$), 35.44 (CH$_2$CH=CH$_3$), 51.68 (CH), 117.70 (CH$_2$CH=CH$_2$), 134.07 (CH$_2$CH=CH$_2$), 169.27 (C(O)CH$_3$), 173.11 (CO$_2$H) ppm; mass spectrum, m/e (relative intensity) 158 (M$^+$+1, 2), 139 (6), 116 (20), 112 (8), 74 (73), 70 (47), 42 (100).

Anal. Calcd for $C_7H_{11}NO_3$: C, 53.50; H, 7.06; N, 8.91. Found: C. 53.64; H, 7.15; N, 8.82.

EXAMPLE 131

Synthesis of 2-Acetamido-4-pentenoic acid-N-benzylamide.

4-Methylmorpholine (0.55 g, 5.40 mmol) was added to a cooled (−10° to −15° C.) THF solution (60 mL) of 2-acetamido-4-pentenoic acid (0.81 g, 5.18 mmol), and then isobutylchloroformate (0.75 g, 5.70 mmol) was added leading to the precipitation of a white solid. After 2 min, a solution of benzylamine (0.61 g, 5.70 mmol) in THF (10 mL) was slowly added at −10° to −15° C. The reaction was allowed to warm (5 min) at room temperature and the insoluble salts were removed by filteration, and the filtrate was evaporated to dryness. The residue was triturated with EtOAc (10 mL), and the remaining white solid was filtered to give 0.81 g (64%) of the desired product: mp 118°–120° C. (recrystallized from ethyl acetate/cyclohexane); $R_f$ 0.36 (4% MeOH/CHCl$_3$); IR (KBr) 3200 (br), 3040, 2900, 1650 (br), 1540 (br), 1350, 750, 700 cm$^{-1}$; $^1H$ NMR (DMSO-$d_6$) δ 1.83 (s, C(O)CH$_3$), 2.22–2.49 (m, CH$_2$CH=CH$_2$), 4.26 (d, J=5.3 Hz, CH$_2$Ph), 4.25–4.33 (m, CH), 4.99–5.09 (m, CH$_2$CH=CH$_2$), 5.65–5.77 (m, CH$_2$CH=CH$_2$), 7.21–7.29 (m, 5 PhH), 8.05 (d, J=7.6 Hz, NH), 8.46 (br s, NH); $^{13}C$ NMR (DMSO-$d_6$) 22.41 (C(O)CH$_3$), 36.24 (CH$_2$CH=CH$_2$), 41.91 (CH$_2$Ph), 52.20 (CH), 117.15 (CH$_2$CH=CH$_2$), 126.54 (C$_4$·), 126.99 (2C$_2$· or 2C$_3$·), 128.04 (2C$_2$· or 2C$_3$·), 139.25 (C$_1$·), 134.25 (CH$_2$CH=CH$_2$), 169.02 (C(O)CH$_3$), 170.96 (C(O)NH) ppm; mass spectrum, m/e (relative intensity) 246 (M$^+$, 4), 205 (4), 163 (15), 140 (8), 106 (33), 91 (77), 70 (100).

Anal. Calcd for $C_{14}H_{18}N_2O_2$: C, 68.27; H, 7.37; N, 11.37. Found: C, 68.55; H, 7.31; N, 11.48.

EXAMPLE 132

Using the procedures described herein, the following compounds can also be synthesized:

α-acetamido-N-benzyl-2-(2-oxazole)-acetamide
α-acetamido-N-benzyl-2-(2-thiazole)-acetamide.

Pharmacology.

Using male Carworth Farms #1 mice, compounds of the present invention were tested for anticonvulsant activity according to the following procedure: In the rotorod test, the animal was placed on a one-inch diameter knurled plastic rod rotating at 6 rpm after the administration of the drug. Normal mice can remain on a rod rotating at this speed indefinitely. Neurologic toxicity was defined as the failure of the animal to remain on the rod for one minute. In the horizontal screen test, previously trained mice were dosed with the compound and placed individually on top of a square (13 cm×13 cm) wire screen (no. 4 mesh) which was mounted on a metal rod. The rod was rotated 180°, and the number of mice that returned to the top of the screen was determined. Inability to climb to the top within one minute was defined as "neurological impairment". This procedure is described in *Pharmacol. Biochem. Behav.* 6, 351–353 (1977) and is incorporated herein by reference with the same force and effect as if fully set forth herein.

The dose effect behavior of the compounds was evaluated using the above-described procedures by the administration of varying dose levels, treating normally eight mice at each dose. Table I includes an evaluation of the Median Effective Dose (ED50) and the Median Toxic Dose (TD50) of representative compounds. Mice were tested with varying doses of the anticonvulsant to define the limits of complete protection (or toxicity) and no protection (or no toxicity), as well as three points in between these limits. The Median Effective Dose (ED50) was defined as the dose which produced the desired endpoint in 50% of the animals. The Median Toxicity Dose (TD50) was the dose which elicited evidence of minimal neurological toxicity in 50% of the animals.

More specifically, data tabulated in Table 1 were generated as follows:

The compound was given in various dose levels (i.e., 10, 30, 100, 300 mg) and subsequently compared with phenytoin, phenobarbital, mephenytoin and phenacemide (See Table I). N-Acetyl-D,L-alanine-N'-benzylamide was tested at 600 mg/mL as well. Seizures were then artifically induced by either electroschock or pentylenetetrazole. Maximal electroshock seizures (MES) were elicited with a 60 cycle alternating current of 50 mA intensity (5–7 times that necessary to elicit minimal electroshock seizures) delivered for 0.2 sec via corneal electrodes. A drop of 0.9% saline was instilled in the eye prior to application of the electrodes so as to prevent the death of the animal. Protection in this test was defined as the abolition of the hind limb tonic extension component of the seizure. The Subcutaneous Pentylenetetrazole (Metrazol™) Seizure Threshold Test (sc Met) entailed the administration of 85 mg/kg of pentylenetetrazole as a 0.5% solution subcutaneously in the posterior midline. This amount of pentylenetetrazole was expected to produce seizures in greater than 95% of mice. The animal was observed for 30 minutes. Protection was defined as a failure to observe even a threshold seizure (a single episode of clonic spasms of at least 5 sec duration). The results of these tests are tabulated in Table I.

TABLE I

| | Comparative Median Effective Dosage | | |
|---|---|---|---|
| Compound | Tox TD50 mg/kg | MES ED50 mg/kg | sc Met ED50 mg/kg |
| N-acetyl-D,L-alanine-N'-benzylamide | 454 (417–501)* | 77 (67–89)* | ≠ |
| N-acetyl-D-alanine-N'-benzylamide | 214 (148–262)* | 55 (50–60)* | 55 (43–67)* |
| N-acetyl-L-alanine-N'-benzylamide | 841 (691–594)* | 548 (463–741)* | ≠ |
| N-acetyl-D,L-phenylglycine-N'-benzylamide | >>40 | 32.1 | ≠ |
| N-acetyl-D-phenyl-glycine-N'-benzyl-amide | >>80 | 26.4 | ≠ |
| N-acetyl-L-phenyl-glycine-N'-benzyl- | 100–300 | >300 | ≠ |

TABLE I-continued

Comparative Median Effective Dosage

| Compound | Tox TD50 mg/kg | MES ED50 mg/kg | sc Met ED50 mg/kg |
|---|---|---|---|
| D,L-α-acetamido-N-benzyl-3-thiophene-acetamide | >100 | 87.80 | ≠ |
| D,L-α-acetamido-N-benzyl-2-thiophene-acetamide | 30–100 | 44.80 | ≠ |
| D,L-α-acetamido-N-benzyl-2-furan-acetamide | 40 | 10.33 | ≠ |
| D,L-α-acetamido-N-benzyl-2-pyrrole-acetamide | <100 | 16.10 | ≠ |
| D,L-2-acetamido-N-benzyl-2-ethoxy-acetamide | >112 | 62.01 | ≠ |
| D,L-2-acetamido-N-benzyl-2-methoxy-acetamide | <300 | 98.30 | ≠ |
| (D,L)-α-Acetamido-N-benzyl-2-(5-methylfuran)acetamide | 75.4[xx] | 19.2 (16.4–23.8)* | ≠ |
| (D,L)-α-Acetamido-N-benzyl-2-benzofuran-acetamide | >100<300[xx] | >100<300 | ≠ |
| (D,L)-α-Acetamido-N-benzyl-2-benzo[b]-thiopheneacetamide | >100<300[xx] | >100<300 | ≠ |
| (D,L)-α-Acetamido-N-benzyl-2-(5-methylpyrrole)acetamide | x | 36.5 (30.6–57.1)* | ≠ |
| (D,L)-α-Acetamido-N-(2-fluorobenzyl)-2-furan-acetamide | x | 40.0 | ≠ |
| (D,L)-α-Acetamido-N-(3-fluorobenzyl)-2-furan-acetamide | 135.6 (114.9–161.8)[xx] | 13.3 (11.5–15.3)* | ≠ |

| Compound | Tox TD 50 mg/kg | MES ED 50 mg/kg | scMet ED 50 mg/kg |
|---|---|---|---|
| 2-acetamido-N-benzyl-2-aminoacetamide | ≠ | 65.1 (56.2–75.3) | ≠ |
| 2-acetamido-N-benzyl-2-(1-Pyrrolyl) acetamide | ≠ | 80.2 | ≠ |
| 2-acetamido-N-benzyl-2-(1-imidazo γ1) acetamide | ≠ | >100 | ≠ |
| 2-acetamido-N-benzyl-2-(N,N-dimethylamino)acetamide | ≠ | 45.3 | ≠ |
| 2-acetamido-N-benzyl-2-(4-morpholine)acetamide | ≠ | >30, <100 | ≠ |
| 2-acetamido-N-benzyl-2-(N,N,N-trimethylammonium) acetamide tetrafluoroborate | ≠ | >100 | ≠ |
| 2-acetamido-N-benzyl-2-(N-anilino)acetamide | ≠ | >300 | ≠ |
| 2-acetamido-N-benzyl-2-(N-(3-pyrazolylamino))acetamide | ≠ | ~100 | ≠ |
| 2,2-diacetamido-N-benzyl-acetamide | ≠ | >100, <300 | ≠ |
| 2-acetamido-N-benzyl-2-trifluoroacetamidoacetamide | ≠ | >300 | ≠ |
| 2-acetamido-N-benzyl-2-(N-hydroxyamino)acetamide | ≠ | ~100 | ≠ |
| 2-acetamido-N-benzyl-2-(N-methoxyamino)acetamide | 46.0[xx] (38.0 . 56.0) | 6.2 (5.4–7.2) | ≠ |
| 2-acetamido-N-benzyl-2-(N,(N-methylhydroxyamino))acetamide | ≠ | ~30 | ≠ |
| 2-acetamido-N-benzyl-2-(N-(N,O-dimethylhydroxyamino)acetamide | 50.5[xx] (40.4–59.9) | 6.7 (5.7–7.7) | ≠ |
| 2-acetamido-N-benzyl-2-(N-isoxazolidino)acetamide | ≠ | 31.4 (26.7–37.8) | ≠ |
| 2-acetamido-N-benzyl-2-(N²-phenylhydrazino)acetamide | ≠ | ~100 | ≠ |
| 2-acetamido-N-benzyl-2-(N²-benzyloxycarbonyl-hydrazino)acetamide | ≠ | 55.6 (49.3–63.9) | ≠ |
| 2-acetamido-N-benzyl-2-hydroxyacetamide | ≠ | 80.1 (70.6–91.0) | ≠ |
| 2-acetamido-N-benzyl-2-(1-Pyrazolyl) acetamide | ≠ | 16.5 (14.1–22.5) | ≠ |
| 2-acetamido-N-benzyl-2-phenoxyacetamide | ≠ | >100 | ≠ |
| 2-acetamido-N-benzyl-2-(methylmercapto)acetamide | ≠ | >100 | ≠ |
| 2-acetamido-N-benzyl-2-(ethylmercapto)acetamide | ≠ | >30, <100 | ≠ |
| 2-acetamido-N-benzyl-2-(S-thiophenoxy)acetamide | ≠ | >300 | ≠ |
| 2-acetamido-N-benzyl-2-(ethylmercapto)acetamide-S-oxide (diastereomer A) | ≠ | >100 | ≠ |
| 2-acetamido-N-benzyl-2-(ethylmercapto)acetamide-S-oxide (diastereomers A + B) | ≠ | >100 | ≠ |
| 2-acetamido-N-benzyl-2-(ethylsulfonyl)acetamide | ≠ | >100 | ≠ |
| (D,L)-α-Acetamido-N-(4-fluorobenzyl)-2-furan-acetamide | 144.4 (122.5–170.9)[xx] | 12.7 (10.4–15.1)* | ≠ |
| (D,L)-α-Acetamido-N-(2,5-difluorobenzyl)-2-furan-acetamide | x | 23.8 (20.2–28.4)* | ≠ |
| (D,L)-α-Acetamido-N-(2,6-difluorobenzyl)-2-furan-acetamide | x | >25>100 | ≠ |
| (D)-(−)-α-Acetamido-N-benzyl-2-furanacetamide | 23.8[xx] | 3.3 (2.8–3.9)* | ≠ |
| (L)-(+)-α-Acetamido-N-benzyl-2-furanacetamide | >300 | >100<300 | ≠ |
| (D,L)-2-Acetamido-4-pentenoic acid-N-benzylamide | x | 33.6 | ≠ |
| 2-acetamido-N-benzyl-2-(2-Pyridyl) acetamide | ≠ | 8.5 | ≠ |
| (D,L)-2-Acetamido-N-benzyl-2-(methylamino)acetamide | 95.0 | 44.5 (37.0–52.4)* | ≠ |
| (D,L)-2-Acetamido-N-benzyl-2-(ethylamino)acetamide | x | 42.4 (37.2–47.8)* | ≠ |
| (D,L)-2-Acetamido-N-benzyl-3-indoleacetamide | x | xxx | ≠ |
| phenytion | 66 | 10 | not effective |
| phenobarbital | 69 | 22 | 13 |
| mephenytion | 154 | 61 | 31 |
| phenacemide | 421 (337–549)* | 87 (74–100)* | 116 (71–150)* |

*95% confidence intervals.
≠ or x The TD50 for this substrate was not computed.
[xx]The TD50 value was determined using the horizontal screen test.
xxx No activity was noted at ≦300 mg/kg Other results from the pharmacological protocols are summarized in Tables II, III and IV.

TABLE II

Selected Physical and Pharmacological Data in Mice for α-Acetamido-N-benzyl-2-furanacetamide (2)-Derivatives.[a]

$$CH_3\overset{\overset{X}{\|}}{C}NH-\overset{\overset{R_a}{|}}{\underset{\underset{R_b}{|}}{C}}-\overset{\overset{Y}{\|}}{C}-NHR_c$$

| CMP # | Ra | Rb | Rc | X | Y | mp[b] | MES[c] ED$_{50}$ mg/kg | Tox[d] TD$_{50}$ mg/kg | PI[e] |
|---|---|---|---|---|---|---|---|---|---|
| 3a | tetrahydrofuran-2-yl | H | CH$_2$CH$_6$H$_5$ | O | O | 159–161 | 51.7 (44.4–59.9) | f | — |
| 3b | tetrahydrofuran-2-yl | H | CH$_2$C$_6$H$_5$ | O | O | 130–132 | 89.8 (78.4–103.4) | f | — |
| 4 | furan-2-yl | CH$_3$ | CH$_2$C$_6$H$_5$ | O | O | —[h] | >300 | f | — |
| 5 | furan-2-yl | H | CH$_2$C$_6$H$_5$ | S | O | 78–80 | 18.4 (15.9–22.0) | f | — |
| 6 | furan-2-yl | H | CH$_2$C$_6$H$_5$ | S | S | 99–101 | >100 | f | — |
| 7 | furan-2-yl | H | CH$_2$-(3-pyridyl) | O | O | 172–174 | ~30 | f | — |
| 8 | furan-2-yl | H | CH$_2$-(4-pyridyl) | O | O | 168–170 | >100 | f | — |
| 9 | furan-2-yl | H | CH$_2$-(3-pyridyl N-oxide) | O | O | 159–161 | ~30 | f | — |
| 10 | furan-2-yl | H | CH$_2$-(4-pyridyl N-oxide) | O | O | 210–212 | >100 | f | — |
| 11 | furan-2-yl | H | NHNH-(pyrimidin-2-yl) | O | O | 226–228 | >100 | f | — |
| 12 | furan-2-yl | H | CH$_2$-C$_6$H$_4$-4-F | O | O | 188–190 | 12.7 (10.4–15.1) | 144 (123–171) | 11.3 |
| (R)-12 | furan-2-yl | H | CH$_2$-C$_6$H$_4$-4-F | O | O | 206–207 | 3.5 (2.9–4.4) | 14.4 (7.3–28.9) | 4.1 |

TABLE II-continued

Selected Physical and Pharmacological Data in Mice for α-Acetamido-N-benzyl-2-furanacetamide (2)-Derivatives.[a]

$$\underset{\underset{R_b}{|}}{\overset{\overset{X}{\|}}{CH_3CNH}} - \overset{R_a}{\underset{|}{C}} - \overset{\overset{Y}{\|}}{C} - NHR_c$$

| CMP # | Ra | Rb | Rc | X | Y | mp[b] | MES[c] ED$_{50}$ mg/kg | Tox[d] TD$_{50}$ mg/kg | PI[e] |
|---|---|---|---|---|---|---|---|---|---|
| (R)-13 | furan | H | CH$_2$-C$_6$H$_4$-CH$_3$ | O | O | 210–212 | <10 | f | — |
| (R)-14 | furan | H | CH$_2$-C$_6$H$_4$-CF$_3$ | O | O | 193–195 | >10, <30 | f | — |
| phenytoin | | | | | | | 9.5 (8.1–10.4) | 65.5[i] (52.5–72.1) | 6.9 |
| phenobarbital | | | | | | | 21.8 (15.0–22.5) | 69.0[i] (62.8–72.9) | 3.2 |
| valproate | | | | | | | 272 (247–338) | 426[i] (369–450) | 1.6 |

[a] The compounds were administered intraperitoneally. ED$_{50}$ and TD$_{50}$ values are in milligrams per kilogram. Numbers in parentheses are 95% confidence intervals. Time of peak effects in hours as determined in the Experimental Section is denoted in brackets.
[b] Melting points (°C.) are uncorrected.
[c] MES = maximal electroshock seizure test. Compound was suspended in 30% PEG.
[d] Tox = neurologic toxicity determined from horizontal screen unless otherwise noted.
[e] PI = protective index (TD$_{50}$ED$_{50}$).
f Not determined.
[h] Thick oil.

TABLE III

Selected Physical and Pharmacological Data in Mice for N-Substituted α,α-Diamino Acid Derivatives.[a]

$$\overset{\overset{O}{\|}}{CH_3CNH} - \overset{R^2}{\underset{|}{CH}} - \overset{\overset{O}{\|}}{C} NHCH_2Ph$$

| no | R² | mp[b] | MES[c] ED$_{50}$ | tox[d] TD$_{50}$ |
|---|---|---|---|---|
| 2e | NHC(O)CH$_3$ | 202–204 | >30, <100 | e |
| 2f | NHC(O)OPh | 201–203 | >100 | e |
| 2g | NHC(O)NHCH$_3$ | 229–230 | >100 | e |
| 2h | NHC(O)NHPh | 242–244 | >100 | e |
| 2i | NHC(O)NHS(O$_2$)Ph | 188–191 | >100 | e |
| 2j | NHC(S)NHCH$_3$ | 162–163 | >100 | e |
| 2k | NHC(S)NHPh | 196–197 | >100 | e |
| 2l | NHC(O)Ph(2'-CO$_2$H) | 186–188 | >100 | e |
| 2m | succinimide | 181–183 | >100 | e |
| 2n | NHC(O)CH$_2$NHC(O)OCH$_2$Ph | 177–179 | >10, <30 | e |
| 2o | NHCH$_2$C(O)OCH$_2$CH$_3$ | 125–127 | >100 | e |
| 2p | NHCH$_2$C(O)OCH$_2$Ph | 133–135 | 72 | 74 |
| 2q | $^+$NH$_2$CH$_2$CO$_2$$^-$ | 124–126 | | |
| phenytoin | | | 95 (8.1–10.4) | 65.5[f] (52.5–72.1) |
| phenobarbital | | | 21.8 (15.0–22.5) | 69.0[f] (62.8–72.9) |
| valproate | | | 272 (247–338) | 426[f] (369–450) |

[a] The compounds were administered intraperitoneally. ED$_{50}$ and TD$_{50}$ values are in milligrams per kilogram. Numbers in parentheses are 95% confidence intervals. Time of peak effects in hours as determined in the Experimental Section is denoted in brackets.
[b] Melting points (°C.) are uncorrected.
[c] MES = maximal electroshock seizure test. Compound was suspended in 30% PEG unless otherwise noted.
[d] Tox = neurologic toxicity determined from horizontal screen unless otherwise noted.
e Not determined.
[f] Neurologic toxicity determined using the rotorod test.

TABLE IV

Pharmacological Data in Mice for α-Acetamido-N-Benzyl-2-Heterocyclic Derivatives $$CH_3-\underset{O}{\overset{\|}{C}}-\underset{H}{\overset{|}{N}}-\underset{R_2}{\overset{|}{CH}}-\overset{O}{\overset{\|}{C}}-NHCH_2$$

| R$_2$ | MES$^a$ ED$_{50}$ | tox$^b$ TD$_{50}$ |
|---|---|---|
| 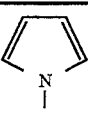 | 80.2 | — |
| 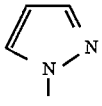 | 16.5 | 66.9 (55.6–81.1) |
| 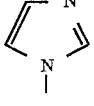 | >100 | — |
| 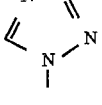 | >30, <100 | — |
| 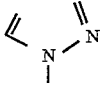 | >300 | — |
| 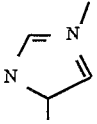 | >100 | — |
| 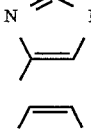 | >100 | >100 |
| 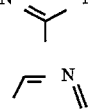 | >100 | — |
| 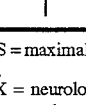 | >100 | — |

$^a$MES = maximal electroshock seizure test. Compound was suspended in 30% PEG.
$^b$TOX = neurologic toxicity determined from horizontal screen unless otherwise noted.

Thus, while the invention has been described with reference to certain preferred embodiments, those skilled in the art will realize that changes and modifications may be made thereto without departing from the full and intended scope of the appended claims.

What is claimed is:

1. A compound of the formula

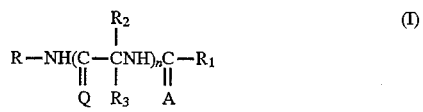

or the N-oxide thereof or pharmaceutically acceptable salts thereof wherein

R is aryl, aryl lower alkyl, heterocyclic or heterocyclic lower alkyl, cycloalkyl, lower cycloalkyl, lower alkyl, wherein R is unsubstituted or is substituted with at least one electron withdrawing group or an electron donating group;

R$_1$ is hydrogen or lower alkyl, lower alkenyl, lower alkynyl, aryl lower alkyl, aryl, heterocyclic lower alkyl, heterocyclic lower cycloalkyl, lower cylcoalkyl, lower alkyl, and R$_1$ is unsubstituted or substituted with at least one electron withdrawing substituent or at least one electron donating substituent;

R$_1$ and R$_3$ are independently hydrogen, lower alkyl lower alkenyl, lower alkynyl, heterocyclic, heterocyclic lower alkyl, lower alkyl heterocyclic, lower cycloalkyl, lower cycloalkyl lower alkyl, SO$_3{}^{31}$ or Z—Y wherein R$_2$ and R$_3$ may be unsubstituted or substituted with at least one electron withdrawing group or electron donating group;

Z is O, S(O)$_a$, NR$_4$, mercaptoalkyl, alkylthio; or a chemical bond;

Y is hydrogen, lower alkyl, aryl, aryl lower alkyl, lower alkenyl, lower alkynyl, halo, heterocyclic or heterocyclic lower alkyl, cycloalkyl, cycloalkyl lower alkyl and Y may be unsubstituted or substituted with an electron donating group or an electron withdrawing group provided that Z is a chemical bond only when Y is halo; or ZY taken together is NR$_4$NR$_5$R$_7$, NR$_4$OR$_5$, ONR$_4$R$_7$, SNR$_4$R$_7$, NR$_4$SR$_7$, SPR$_4$R$_5$,

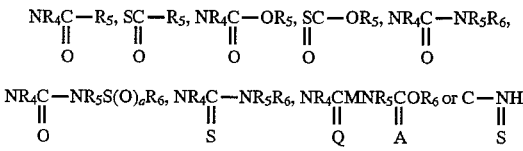

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group;

R$_7$ is R$_6$, COOR$_8$ or COR$_8$;

R$_8$ is hydrogen or lower alkyl or aryl lower alkyl;

n is 1–4 and a is 1–3

M is a lower alkylene chain, and A and Q are independently O or S with the provisio that at least one of A or Q is S.

2. The compound, according to claim 1 wherein A is S.

3. The compound according to claim 1 wherein A and Q are S.

4. The compound according to claim 1 wherein one of R$_2$ and R$_3$ is H.

5. The compound according to claim 4 wherein one of R$_2$ and R$_3$ is H and the other is heterocyclic.

6. The compound according to claim 5 wherein heterocyclic is furyl, pyrrolyl, pyrazoyl, epoxy, oxazolyl, imidazolyl, tetraxolyl, triazolyl, or oxadiaxoyl.

7. The compound according to claim 6 wherein heterocyclic is furyl, pyrrolyl, pyrozolyl, or pyridyl.

8. The compound according to claim 1 wherein one of $R_2$ and $R_3$ is H and the other is Z—Y.

9. The compound according to claim 8 wherein Z—Y is N,O-dimethylhydroxyamino, N-methylhydroxyamino N-methoxyamino, ethylamino or methylamino or hydrazino.

10. A compound of the formula

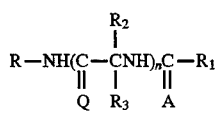

or the N-Oxide thereof or pharmaceutically acceptable salts thereof wherein

R is aryl, aryl lower alkyl, heterocyclic or heterocyclic lower alkyl, cycloalkyl, lower cycloalkyl lower alkyl, wherein R is unsubstituted or is substituted with at least one electron withdrawing group or an electron donating group;

$R_1$ is hydrogen or lower alkyl and $R_1$ is unsubstituted or substituted with at least one electron withdrawing substituent or at least one electron donating substituent;

one of $R_2$ and $R_3$ is hydrogen, and the other is $SO_3$—, A and O are independently O or S and n is 1–4.

11. The compound according to claim 10 wherein Q and A are both O.

12. A compound of formula

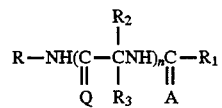

or the N-Oxide thereof or pharmaceutically acceptable salts thereof wherein

R is aryl, aryl lower alkyl, heterocyclic or heterocyclic lower alkyl, cycloalkyl, lower cycloalkyl, lower alkyl, wherein R is unsubstituted or is substituted with at least one electron withdrawing group or an electron donating group;

$R_1$ is hydrogen or lower alkyl and $R_1$ is unsubstituted or substituted with at least one electron withdrawing substituent or at least one electron donating substituent;

$R_2$ and $R_3$ are independently hydrogen, alkyl, or Z—Y wherein $R_2$ and $R_3$ may be unsubstituted or substituted with at least one electron withdrawing group or electron donating group;

Z is $S(O)_a$, mercaptoalkyl, or alkylthio

Y is hydrogen, lower alkyl, aryl, aryl lower alkyl, lower alkenyl, lower alkynyl, heterocyclic or heterocyclic lower alkyl, cycloalkyl, cycloalkyl lower alkyl and Y may be unsubstituted or substituted with an electron donating group or an electron withdrawing group provided that when Y is halo, Z is a chemical bond; or ZY taken together is $NR_4$

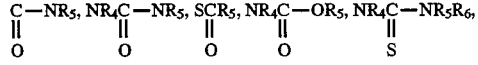

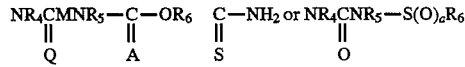

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group;

n is 1–4 and a is 1–3

M is lower alkylene, and A and Q are independently O or S with the provisio that at least one of $R_2$ and $R_3$ is Z—Y.

13. The compound of claim 12 wherein A and Q are both oxygen.

14. A compound of the formula

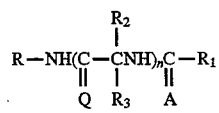

or the N-Oxide thereof or pharmaceutically acceptable salts thereof wherein

R is aryl, aryl lower alkyl, heterocyclic or heterocyclic lower alkyl, cycloalkyl, lower cycloalkyl, lower alkyl, wherein R is unsubstituted or is substituted with at least one electron withdrawing group or an electron donating group;

$R_1$ is hydrogen or lower alkyl and $R_1$ is unsubstituted or substituted with at least one electron withdrawing substituent or at least one electron donating substituent;

$R_1$ and $R_3$ are independently hydrogen, amino, pyrrolyl, N,N-dimethylamino, morpholinyl, pyrazinyl, —NH $OCH_3$, methylhydroxyamino, (N,O—) dimethylhydroxyamino

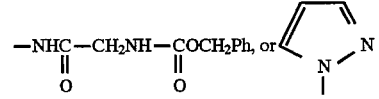

or epoxy, and n is 1–4, provided that at least one of $R_2$ and $R_3$ is other than hydrogen.

15. The compound according to claim 14 wherein Q and A are both O.

16. The compound according to any one of claims 1–15 wherein n is 1.

17. The compound according to any one of claims 1–15 wherein R is lower arylalkyl which is unsubstituted or substituted with an electron donating group or electron withdrawing group.

18. The compound according to claim 17 wherein R is benzyl which is unsubstituted or substituted with an electron withdrawing group or electron donating group.

19. The compound according to claim 18 wherein R is unsubstituted benzyl or

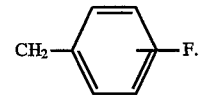

20. The compound according to any of claims 1–15 wherein $R_1$ is lower alkyl.

21. The compound according to claim 20 wherein $R_1$ is methyl.

22. A compound selected from the group consisting of ethyl 2-acetamido-2-aminoacetate, ethyl 2-acetamido-2-(methylamino)acetate, ethyl 2-acetamido-2-(N,N-dimethylamino)acetate, ethyl 2-acetamido-2-(4- morpholine)acetate, ethyl 2-acetamido-2-(N-anilino)acetate, ethyl 2-acetamido-2-(N-(3-pyrazolylamino))acetate, ethyl 2-acetamido-2-(N-hydroxyamino)acetate, ethyl 2-acetamido-2-(N-(N-methylhydroxyamino))acetate, ethyl 2-acetamido-2-(N-(N,O-dimethylhydroxyamino))acetate, 2-acetamido-N-benzyl-2-aminoacetamide, 2-acetamido-N-benzyl-2-(methylamino)acetamide, 2-acetamido-N-benzyl-2-(ethylamino)acetamide, 2-acetamido-N-benzyl-2-(N-anilino)acetamide, 2-acetamido-N-benzyl-2(N-(3-pyrazolylamino))acetamide, 2-acetamido-N-benzyl-2-(N,N-dimethylamino)acetamide, 2-acetamido-N-benzyl-2-(N-hydroxyamino)acetamide, 2-acetamido-N-benzyl-2-(N-hydroxyamino)acetamide, 2-acetamido-N-benzyl-2-($N^2$-phenylhydrazino)acetamide, 2-acetamido-N-benzyl-2-($N^2$-benzyloxycarbonylhydrazino)acetamide, 2-acetamido-N-benzyl-2-phenoxyacetamide, 2-acetamido-N-benzyl-2-(methylmercapto)acetamide, 2-acetamido-N-benzyl-2-(ethylmercapto)acetamide, 2-acetamido-N-benzyl-2-(N-methoxyamino)acetamide, 2-acetamido-N-benzyl-2-(N-(N-methylhydroxyamino))acetamide, 2-acetamido-N-benzyl-2-(N-(N,O-dimethylhydroxyamino))acetamide, 2-acetamido-N-benzyl-2-(N-isoxazolidino)acetamide, 2-acetamido-N-benzyl-2-hydroxyacetamide, 2-acetamido-N-benzyl-2-(ethylmercapto)acetamide, 2,2-diacetamido-N-benzylacetamide, 2-acetamido-N-benzyl-2-trifluoracetamidoacetamide, 2-acetamido-N-benzyl-2-(N,N,N-trimethylammonium)acetamide tetrafluoroborate, 2-acetamido-N-benzyl-2-(ethylmercapto)acetamide-S-oxide, 2-acetamido-N-benzyl-2-(S-ethylmercapto)acetamide-S-oxide, 2-acetamido-N-benzyl-2-(ethanesulfonyl)acetamide, 2-acetamido-N-benzyl-2-(N,N,N-trimethylammonium)acetamide tetrafluoroborate, 2-acetamido-N-benzyl-2-(1-pyrrole)acetamide, 2-acetamido-N-benzyl-2-(1-imidazole)acetamide, 2-acetamido-N-benzyl-2-(1-pyrazole)acetamide, 2-acetamido-N-benzyl-2(1-(1,2,4-triazole))acetamide, 2-acetamido-N-benzyl-2(1-tetrazole))acetamide, α-acetamido-N-benzyl-2-pyridylacetamide, α-acetamido-N-benzyl-2-pyridyl acetamide N-oxide, α-acetamido-N-benzyl-2-(S-thiophenoxy)-acetamide, α-acetamido-N-benzyl-2-(tetrahydrofuran)acetamide, methyl α-acetamido-2-methyl-2-furanacetate, α-acetamido-2-methyl-2-furanacetic acid, α-acetamido-N-benzyl-2-methyl-2-furanacetamide, α-thioacetamido-N-benzyl-2-furanacetamide, α-thioacetamido-N-benzyl-2-furanthioacetamide, α-acetamido-N-(3-pyridinylmethyl)-2-furanacetamide, α-acetamido-N-(4-pyridinylmethyl)-2-furanacetamide, α-acetamido-N-(1-oxo-3-pyridinylmethyl)-2-furanacetamide, α-acetamido-N-(1-oxo-4-pyridinylmethyl)-2-furanacetamide, R(−)α-acetamido-N-(4-fluorobenzyl)-2-furanacetamide, R(−)α-acetamido-N-(4-trifluoromethylbenzyl)-2-furanacetamide, methyl [acetamido(benzylcarbamoyl)methyl]carbomate, phenyl [acetamido(benzylcarbamoyl)methyl]carbomate, 1-[acetamido(benzylcarbamoyl)methyl]-3-methylurea), 1-[acetamido(benzylcarbamoyl)methyl]-3-phenylurea), 1-[acetamido(benzylcarbamoyl)methyl]-3-benzenesulfonylurea), 1-[acetamido(benzylcarbamoyl)methyl]-3-methylthiourea), 1-[acetamido(benzylcarbamoyl)methyl]-3-phenylthiourea), N-[acetamido(benzylcarbamoyl)methyl]phthalamic acid), 2-acetamido-N-benzyl-2-(N-succinimidyl)acetamide), benzyl N-[acetamido(benzylcarbamoyl)methyl]malonamate, ethyl N-[acetamido(benzylcarbamoyl)methyl]glycinate, benzyl N-[acetamido(benzylcarbamoyl)methyl]glycinate, N-[acetamido(benzylcarbomoyl)methyl]glycine, 2-acetamide-N-benzyl-2-(1-pyrrole)acetamide, 2-acetamido-N-benzyl-2-(1-pyrazole)acetamide, 2-acetamido-N-benzyl-2-(1-imidazole)acetamide, 2-acetamido-N-benzyl-2-(1-(1,2,4-triazole))acetamide, 2-acetamido-N-benzyl-2-(1-tetrazole))acetamide, α-acetamido-N-benzyl-1-(dimethylsulfamoyl)imidazole-4-acetamide, α-acetamido-N-benzyl-4-imidazole acetamide, α-acetamido-N-benzyl-2-imidazole acetamide, α-acetamido-N-benzyl-5-(tetrazole)acetamide, α-acetamido-N-benzyl-3-(1,2,4-triazole)acetamide, α-acetamido-N-benzyl-2-(carboxamide oxime)acetamide, α-acetamido-N-benzyl-2-(carboxamide oxime-(O-acetate))-acetamide, α-acetamido-N-benzyl-3-(1,2,4-oxadiazole)acetamide, α-acetamido-N-benzyl-2-(thioamide)acetamide), 2-acetamido-N-benzyl-2-vinylacetamide, 2-acetamido-N-benzyl-2-epoxyacetamide, potassium 2-acetamido-N-benzylacetamide-2-sulfonate, 2-acetamido-4-pentenic acid-N-benzylamide, α-acetamido-N-benzyl-2-(2-oxazole)-acetamide, and α-acetamido-N-benzyl-2-(2-thiazole)-acetamide.

23. An anti-convulsant composition comprising an anti-convulsant effective amount of a compound from any one of claims 1–15 and 22 and a pharmaceutical carrier therefor.

24. An anti-convulsant composition comprising an anti-convulsant effective amount of a compound from claim 16 and a pharmaceutical carrier therefor.

25. An anti-convulsant composition comprising an anti-convulsant effective amount of a compound from claim 17 and a pharmaceutical carrier therefor.

26. An anti-convulsant composition comprising an anti-convulsant effective amount of a compound from claim 18 and a pharmaceutical carrier therefor.

27. An anti-convulsant composition comprising an anti-convulsant effective amount of a compound of claim 19 and a pharmaceutical carrier therefor.

28. An anti-convulsant composition comprising an anti-convulsant effective amount of a compound of claim 20 and a pharmaceutical carrier therefor.

29. An anti-convulsant composition comprising an anti-convulsant effective amount of a compound of claim 21 and a pharmaceutical carrier therefor.

30. A method of treating CNS disorders in an animal comprising administering to said animal an anti-convulsant effective amount of a compound according to any one of claims 1–15 and 22.

31. A method of treating CNS disorders in an animal comprising administering to said animal an anti-convulsant effective amount of a compound of claim 16.

32. A method of treating CNS disorders in an animal comprising administering to said animal an anti-convulsant effective amount of a compound of claim 17.

33. A method of treating CNS disorders in an animal comprising administering to said animal an anti-convulsant effective amount of a compound of claim 18.

34. A method of treating CNS disorders in an animal comprising administering to said animal an anti-convulsant effective amount of a compound of claim 19.

35. A method of treating CNS disorders in an animal comprising administering to said animal an anti-convulsant effective amount of a compound of claim 20.

36. A method of treating CNS disorders in an animal comprising administering to said animal an anti-convulsant effective amount of a compound of claim 21.

37. The compound according to any one of claims 1, 10, 12 or 14 wherein n is 1 and R is lower alkyl which is unsubstituted or substituted with an electron donating group or electron withdrawing group.

38. The compound according to any one of claims 1, 10, 12 or 14 wherein n is 1; $R_1$ is methyl and R is lower arylalkyl which is unsubstituted or substituted with an electron withdrawing group or electron donating group.

39. A compound of the formula

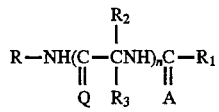 (I)

or the pharmaceutically acceptable salts thereof wherein

R is aryl, aryl lower alkyl, heterocyclic, heterocyclic lower alkyl, cycloalkyl or lower cycloalkyl lower alkyl, wherein R is unsubstituted or is substituted with at least one electron withdrawing group or an electron donating group;

$R_1$ is hydrogen or lower alkyl and $R_1$ is unsubstituted or substituted with at least one electron withdrawing group or at least one electron donating group;

A and Q are both O;

one of $R_2$ and $R_3$ is hydrogen and the other is lower alkyl which is substituted with an electron donating group or a electron withdrawing group and n is 1–4.

40. The compound according to claim 39 wherein one of $R_2$ and $R_3$ is hydrogen and the other is lower alkyl substituted with an electron donating group.

41. The compound according to claim 40 wherein one of $R_2$ and $R_3$ is alkyl substituted with an electron donating group wherein alkyl is methyl, ethyl, propyl, isopropyl, butyl, isobutyl, t-butyl, amyl or hexyl.

42. The compound according to claim 41 wherein one of $R_2$ and $R_3$ is methyl substituted with an electron donating group.

43. The compound according to claim 42 wherein the electron donating group is lower alkoxy.

44. The compound according to claim 43 wherein lower alkoxy is methoxy.

45. The compound according to any one of claims 39–44 wherein n is 1.

46. An anti-convulsant composition comprising an anti-convulsant effective amount of a compound from any one of claim 37–42 and a pharmaceutical carrier therefor.

47. A method of treating CNS disorders in an animal comprising administering to said animal an anti-convulsant effective amount of a compound of any one of claims 39–44.

* * * * *

UNITED STATES PATENT AND TRADEMARK OFFICE
CERTIFICATE OF CORRECTION

PATENT NO. : 5,654,301
DATED : August 5, 1997
INVENTOR(S) : Harold Kohn, et al.

It is certified that error appears in the above-identified patent and that said Letters Patent is hereby corrected as shown below:

Column 34,
Line 59: "Ch $_3$ H)" should read -- $C_3$ H) --
Line 59: "8.62 Hz" should read -- 8.62 (d,J=7.7 --
Line 60: "H," should read -- Hz, --

Column 35,
Line 15: "form" should read -- formed --
Line 35: "8.89" should read -- 8.99 --

Column 37,
Line 53: "α" should read -- 2 --
Line 60: "or" should read -- of --

Column 38,
Line 65: "13$_c$" should read -- 13 $_c$ --

Column 40,
Line 25: "2.33" should read -- 2.23 --
Line 25: "425" should read -- 4.25 --
Line 67: "($M^{30}$=1)" should read -- ($M^+$= 1) --

Column 41,
Line 25: "2-hydroxyamino" should read -- 2-(N-hydroxyamino) --

Column 42,
Line 55: "($M^+$ + 100)" should read -- ($M^+$ + 1,100) --

Column 19,
Line 30: "intraperitoncally" should read -- intraperitoneally --

Column 27,
Line 45: "16 °" should read -- 169 ° --

Column 28,
Line 56: "7.1.7" should read -- 7.17 --

Column 30,
Line 37: "63" should read -- 6.3 --
Line 64: "785" should read -- 735 --

UNITED STATES PATENT AND TRADEMARK OFFICE
CERTIFICATE OF CORRECTION

PATENT NO. : 5,654.301
DATED : August 5, 1997
INVENTOR(S) : Harold Kohn, et al.

It is certified that error appears in the above-identified patent and that said Letters Patent is hereby corrected as shown below:

Column 31,
Line 21: "cbloroform" should read -- chloroform --
Line 49: "2.78" should read -- 2.75 --

Column 33,
Line 16: "(D,L" should read -- (D,L) --
Line 38: "94:4" should read -- 96:4 --
Lines 41 & 42: "80" should read -- 8.0 --
Line 48: "$C_3'$" should read -- $C_6'$ --

Column 34,
Line 15: "130" should read --139 --
Line 41: "M + 1" should read -- $M^+ + 1$ --

Column 43,
Lines 21 & 49: "acetamido" should read -- acetamide --
Line 59: "1.84'" should read -- 1.84 --

Column 44,
Line 46, "n" should read -- a --
Line 46: "ethoxyacetamido" should read -- ethoxyacetamide --
Line 65: "acetamido" should read -- acetamide --

Column 45,
Line 18: after "spectrum" insert -- (FD) --
Line 39: "7.5" should read -- 7.52 --
Line 56: "73.3" should read -- 7.33 --

Column 46,
Line 25: "$CH_3Cl_2$," should read -- $CH_2Cl_2$ --

Column 49,
Lines 57-58: "O-methylhydroxyamino" should read -- O-dimethylhydroxyamino --

Column 50,
Line 40: "149" should read -- 14.9 --

UNITED STATES PATENT AND TRADEMARK OFFICE
CERTIFICATE OF CORRECTION

PATENT NO.  : 5,654.301
DATED       : August 5, 1997
INVENTOR(S) : Harold Kohn, et al.

It is certified that error appears in the above-identified patent and that said Letters Patent is hereby corrected as shown below:

Column 51,
Line 24: "accetamido" should read -- acetamide --
Line 38: "Dicacetamido" should read -- Diacetamide --
Line 46: "and-was" should read -- and was --

Column 52,
Line 16: "166.3.9" should read -- 166.39 --

Column 54,
Line 16: "Time" should read -- The --

Column 55,
Line 7: "H" should read -- It --

Column 56,
Line 55: "$C_1$" should read -- $C_{12}$ --
Line 66: "while" should read -- white --
Line 66: "alter" should read -- after --

Column 58,
Line 30: "dr" should read -- dt --

Column 59,
Line 62: after "1.89" insert -- (s, --
Line 63: Delete -- (s, --

Column 60,
Line 4: "1" should read -- 91 --

Column 61,
Line 30: "($C_2$), H" should read -- $CH_2$ ), --

Column 63,
Line 38: "add" should read -- acid --

Column 65,
Line 10: "8.62" should read -- 8.61 --
Line 21: "arthydride" should read -- anhydride --

UNITED STATES PATENT AND TRADEMARK OFFICE
CERTIFICATE OF CORRECTION

PATENT NO. : 5,654.301
DATED : August 5, 1997
INVENTOR(S) : Harold Kohn, et al.

It is certified that error appears in the above-identified patent and that said Letters Patent is hereby corrected as shown below:

Column 66,
Line 34: "600" should read -- 670 --

Column 67,
Line 22: "63.72" should read -- 63.22 --
Line 63: "170.30" should read -- 170.03 --
Line 66: "$N_{402}$" should read -- $N_4 O_2 S$ --

Column 68,
Line 9: "while" should read -- white --
Line 67, "1.80" should read -- 181 --

Column 69,
Line 8: "176.5" should read -- 176.33 --
Lines 45-46: "Found: C,60.90: C, 61.16; H, 587; N, 1358.H, 5.77; N, 13.35." should read -- C, 61.16;H, 5.87; N, 13.58. Found: C, 60.90; H,5.77;N, 13.35. --
Line 57: "29o" should read -- 2o --

Column 70,
Line 41: "2g" should read 2q --

Column 76,
Line 3: "BF3" should read -- $BF_3$ --
Line 37, "NHH" should read -- NHH' --

Column 81,
Line 47: "imidazo" should read -- imidazoyl --

Column 82,
Line 6: "38.0 . 56.0" should read -- 38.0-56.0 --

Column 83,
Line 15: "$CH_2 CH_6 H_5$" should read -- $CH_2 C_6 H_5$ --

Column 84,
Line 63: "206" should read -- 205 --

Column 86,
Line 47: "95" should read -- 9.5 --

UNITED STATES PATENT AND TRADEMARK OFFICE
CERTIFICATE OF CORRECTION

PATENT NO. : 5,654.301
DATED : August 5, 1997
INVENTOR(S) : Harold Kohn, et al.

It is certified that error appears in the above-identified patent and that said Letters Patent is hereby corrected as shown below:

Column 88, claim 1:
Line 24, "$SO_3^{31}$" should read -- $SO_3$ --

Column 89, claim 10:
Line 26, "O" should read -- A and Q --

Column 90, claim 14:
Line 28, "$R_1$" should read -- $R_2$ --

Column 90, claim 17:
Line 46, "1-15wherein" should read -- 1-16 wherein --

Column 90, claim 20:
Line 60, "1-15" should read -- 1-19 --

Signed and Sealed this

Twenty-seventh Day of November, 2001

Attest:

NICHOLAS P. GODICI
Attesting Officer   Acting Director of the United States Patent and Trademark Office